US007326541B2

(12) United States Patent
Pelletier et al.

(10) Patent No.: US 7,326,541 B2
(45) Date of Patent: Feb. 5, 2008

(54) **FRAGMENTS AND VARIANTS OF *STAPHYLOCOCCUS AUREUS* DNAG PRIMASE, AND USES THEREOF**

(75) Inventors: Jerry Pelletier, Baie-D'Urfe (CA);
Philippe Gros, St. Lambert (CA);
Michael DuBow, Antony (CA);
Dominique Bergeron, Montreal (CA)

(73) Assignee: Targanta Therapeutics, Inc., St. Laurent, Quebec (CA)

( * ) Notice: Subject to any disclaimer, the term of this patent is extended or adjusted under 35 U.S.C. 154(b) by 186 days.

(21) Appl. No.: 10/025,222

(22) Filed: Dec. 19, 2001

(65) Prior Publication Data

US 2003/0003444 A1 Jan. 2, 2003

Related U.S. Application Data

(60) Provisional application No. 60/256,349, filed on Dec. 19, 2000.

(51) Int. Cl.
*C12Q 1/48* (2006.01)
*C12N 9/12* (2006.01)
*C07K 1/00* (2006.01)

(52) U.S. Cl. .......................... 435/15; 435/194; 530/350
(58) Field of Classification Search ................ 530/350, 530/324–328; 435/194; 514/2; 424/94.21, 424/94.5
See application file for complete search history.

(56) References Cited

U.S. PATENT DOCUMENTS

| | | | |
|---|---|---|---|
| 4,946,968 A | 8/1990 | Krimmer et al. | |
| 5,766,904 A | 6/1998 | Mollet et al. | |
| 6,037,123 A | 3/2000 | Benton et al. | |
| 6,043,038 A | 3/2000 | Sivaraja et al. | |
| 6,162,617 A * | 12/2000 | Burgett et al. | 435/69.1 |
| 6,187,541 B1 | 2/2001 | Benton et al. | |
| 6,228,588 B1 | 5/2001 | Benton et al. | |
| 6,380,370 B1 * | 4/2002 | Doucette-Stamm et al. | 536/23.1 |

FOREIGN PATENT DOCUMENTS

| | | |
|---|---|---|
| EP | 0 072 925 A2 | 3/1983 |
| EP | 0 748 871 A1 | 12/1996 |
| EP | 0 786 519 | 7/1997 |
| WO | WO89/00199 A1 | 1/1989 |
| WO | WO95/27043 A1 | 10/1995 |
| WO | WO98/26072 | 6/1998 |
| WO | WO99/37661 | 7/1999 |
| WO | WO 00/32825 | 6/2000 |
| WO | WO 01/09164 | 2/2001 |
| WO | WO 02/094868 | 11/2002 |

OTHER PUBLICATIONS

Branden et al. "Introduction to Protein Structure", Garland Publishing Inc., New York, 1991.*
Witkowski et al. (1999) Biochemistry 38:11643-11650.*
Abaza et al. (1992) J Protein Chem 11:433-444.*
Colman et al. (1996) Res Immun 145:33-36.*
Scott et al. (1999) Nat Genet 21:440-443.*
Brenner (1999) Trends Genet 15:132-133.*
"Encyclopedia of Molecular Biology" Creighton, T., John Wiley and Sons, Inc. New York, 1999, pp. 1994-1995, 2020-2021, and 2027-2033.*
Buckingham, 4th Horizon Symposium, Picking the Pockets of Protein-Protein Interactions, Apr. 2004, pp. 1-4.*
Charkrabarti et al. (2002) Proteins 47:334-343.*
Bogan et al. (1998) J. Mol Biol 280:1-9.*
Alonso et al., "Functional analysis of the *dna* (ts) mutants of *Bacillus Subtilis*: Plasmid pUB110 replication as a model system," Mol. Gen. Genet, 214:482-489, 1988.
Benkovic et al., "Replisome-Mediated DNA Replication," Ann. Rev. Biochem., 70:181-208, 2001.
Benvenisty et al., "Direct introduction of genes into rats and expression of the genes," Proc. Natl. Acad. Sci. USA, 83:9551-9555, 1986.
Bird et al., "Mapping Protein-Protein Interactions within a Stable Complex of DNA Primase and DnaB Helicase from *Bacillus stearothermophilus*," Biochemistry, 39:171-182, 2000.
Chee et al., "Assessing Genetic Information with High-Density DNA Arrays," Science, 274:610-614, 1996.
Clackson et al., "Making antibody fragments using phage display libraries," Nature, 352:624-628, 1991.
Cole et al., "The EBV-Hybridoma Technique and Its Application to Human Lung Cancer," *Monoclonal Antibodies and Cancer Therapy*, Proceedings of the Roche-UCLA Symposium held in Park City, Utah, 77-96, 1985.
Cotton et al., "Reactivity of cytosine and thymine in single-base-pair mismatches with hydroxylamine and osmium tetroxide and its application to the study of mutations," Proc. Nat. Acad. Sci. USA, 85:4397-4401, 1955.
Creighton, *Proteins: Structures and Molecular Properties*, New York: Freeman and Company, 1993, p. 78-99.
*Current Protocols in Immunology*, edited by John Coligan, vol. 1, Chapter 5, New York: John Wiley & Sone, 1991.
Drews et al., "Drug Discovery: A Historical Perspective," Science, 287:1960-1964, 2000.

(Continued)

*Primary Examiner*—David J. Steadman

(57) ABSTRACT

The invention relates to bacterial genes and proteins that are implicated in the process of DNA replication and also to bacteriophage genes and their protein products that interact with bacterial proteins involved in DNA replication. More particularly, the invention relates to compositions and methods involving an essential *Staphylococcus aureus* gene and its encoded protein STAAU_R9. In addition, the invention relates to screening assays to identify compounds which modulate the level and/or activity of STAAU_R9 and to such compounds.

13 Claims, 20 Drawing Sheets

OTHER PUBLICATIONS

Eisenbraun et al., "Examination of Parameter: Affecting the Elicitation of Humoral Immune Responses by Particle Bombardment-Mediated Genetic Immunization," DNA and Cell Biology, 12:791-797, 1993.

Frohman et al., "Rapid production of full-length cDNAs from rare transcripts: Amplification using a single gene-specific oligonucleotide primer," Proc. Nat. Acad. Sci. USA, 85:8998-9002, 1988.

Gentz et al., "Bioassay for trans-activation using purified human immunodeficiency virus tat-encoded protein: Trans-activation requires mRNA synthesis," Proc. Nat. Acad. Sci. USA, 86:821-824, 1989.

Haard et al., "A Large Non-immunized human fab fragment phage library that permits rapid isolation and kinetic analysis of high affinity antibodies," Journal Biological Chemistry, 274: 18218-18230, 1999.

Harbarth et al., "Impact of Methicillin Resistance on the Outcome of Patients with Bacteremia Caused by *Staphylococcus aureus*," Arch, Intern. Med., 158:182-189, 1998.

Henikoff et al., "Amino acid substitution matrices from protein blocks," Proc. Nat. Acad. Sci. USA, 89:10915-10919, 1992.

Higgs et al., "Fluorometric Assay for DNA Polymerases and Reverse Transcriptase," BioTechniques, 21:644-672, 1996.

Jones et al., "Replacing the complementarity-determining regions in a human antibody with those from a mouse," Nature, 321: 522-525, 1986.

Kaelin et al., "Expression Cloning of a cDNA Encoding A Retinoblastoma-Binding Protein with E2F-like Properties," Cell, 70:351-364, 1992.

Kaneda et al., "Increased expression of DNA cointroduced with nuclear protein in adult rat liver," Science, 243:375-378, 1989.

Kohler et al., "Continuous cultures of fused cells secreting antibody of predefined specificity," Nature, 256: 495-497, 1975.

Kornberg et al., Prokaryotic DNA Polymerases Other Than *E.coli* Pol 1, Chapter 5, *DNA Replication*, 2nd edition, New York: Freeman and Company, 1992.

Kozbor et al., "The production of monoclonal antibodies from human lymphocytes," Immunology Today, vol. 4, No. 3, 72-79, 1983.

Kreiswirth et al., "The toxic shock syndrome exotoxin structural gene is not detectably transmitted by a prophage," Nature, 305: 709-712, 1983.

Ladner, "Display and Selection of Proteins on Genetic Packages," Chapter 10, *Phage Display of Peptides and Proteins*, 151-193, 1996.

Laemmli, "Cleavage of Structural Proteins during the assembly of the head of bacteriophage T4," Nature, 227: 680-685, 1970.

Lu et al., "Direct physical interaction between DnaG primase and DnaB helicase of *Escherichia coli* is necessary for optimal synthesis of primer RNA," Proc. Nat. Acad. Sci. USA, 93:12902-12907, 1996.

Maeji et al., "Systematic screening for bioactive peptides," Peptide Research, vol. 4, No. 3, 142-146, 1991.

Manthorpe et al., "Gene therapy by intramuscular injection of plasmid DNA: Studies on firefly luciferase gene expression in mice," Human Gene Therapy, vol. 4, 419-431, 1993.

Marks et al., "By-passing immunization: Building high affinity human antibodies by chain shuffling," Bio technology, 10:777-783, 1992.

McCafferty et al., "Phage antibodies: filamentous phage displaying antibody variable domains," Nature 348; 552-554 (1990).

Myers et al., Detection of single base substitutions by Ribonuclease cleavage at mismatches in RNAAA:DNA duplexes, Science, 230:1242-1246, 1985.

Needleman et al., "A General method applicable to the search for similarities in the amino acid sequence of two proteins," J. Mol. Biol., 48:433-453, 1970.

Okano et al., "Myelin base protein gene and the function of antisense RNA in its repression in myelin-deficient mutant mouse," Journal of Neurochemistry, 56: 560-567, 1991.

Oskouian et al., "Repression and catabolite repression of the lactose operon of *Staphylococcus aureus*," Journal of Bacteriology, 172: 3804-3812, 1990.

Qin et al., "A Strategy for rapid, high-confidence protein identification," Annal. Chem., 69:3995-4001, 1997.

Rattan et al., "Protein synthesis, posttranslation modifications, and aging," An. N.Y. Acad. Of Sci., 663: 48-62, 1992.

Roder et al., "Clinical features of *Staphylococcus aureus* endocarditis," Arch, Int. Med., 159:462-469, 1999.

Rowen et al., "Primase, the dnaG Protein of *Escherichiaa coli*," Journal of Biological Chemistry, 253: 758-764, 1978.

Seeger et al., "The cloned genome of ground squirrel hepatitis virus is infectious in the animal," Proc. Natl. Acad. Sci. USA, 81: 5849-5852, 1984.

Seifter et al., "Analysis for protein modifications and nonprotein cofactors," Meth. Enzymol., 182: 626-646, 1990.

Sittampalam et al., "high-throughput screening: advances in assay technologies," Current Opin. Chem. Biol., 3:384-391, 1997.

Smith et al., "Identification of common molecular subsequences," J. Mol. Biol., 147: 195-197, 1981.

Swanstrom et al., "Agar layer method for production of high titer phage stocks," Proc. Soc. Expt. Biol. Med., 372-375, 1951.

Tang et al., "Genetic immunization in a simple method for eliciting an immune response," Nature, 356: 152-154, 1992.

Tauriainen et al., "Recombinant luminescent bacteria for measuring bioavailable arsenite and antimonite," Appl. Environ. Microbiol., 63: 4456-4461, 1997.

Tempest et al., "Reshaping a human monoclonal antibody to inhibit human respiratory syncytial virus infection in vivo," Biotechnology, 9: 266-273, 1991.

Tougu et al., "Identification of a domain of *Escherichia coli* primase required for functional interaction with the DnaB helicase at the replication fork," J. Biol. Chem., 269:4675-4682, 1994.

Tougu et al., "The Interaction between Helicase and Primase sets the replication fork clock," J. Biol. Chem., 271: 21398-21405, 1996.

Wilson et al., "The structure of an antigenic determinant in a protein," Cell, 37:767-778, 1984.

Wold, "Posttranslational protein modifications: perspectives and prospectives," *Posttranslational Covalent Modification of Proteins*, New York: Academic Press, 1983.

Wolff et al., "Long-term persistence of plasmid DNA and foreign gene expression in mouse muscle," Human Mol. Genet., 1:363-369, 1992.

Wu et al., "Coordinated leading- and lagging-strand synthesis at the *Escherichia coli* DNA replication fork," J. Biol. Chem., 267: 4074-4083, 1992.

Wu et al., "Targeting genes: Delivery and persistent expression of a foreign gene driven by mammalian regulatory elements *in Vivo*," J. Biol. Chem., 264: 16985-16987, 1989.

Yuzhakov et al., "Trading Places on DNA—A Three-Point Switch Underlies Primer Handoff from Primase to the Replicative DNA Polymerase," Cell, 96: 153-163, 1999.

The National Center for Biotechnology Information (NCBI), Accession No. AB001896, XP-002236249, Feb. 1999.

Sheehan et al., The lytic enzyme of the pneumococcal phage Dp-1: a chimeric lysin of intergeneric origin. *Molecular Microbiology* 25(4):717-725 (1997).

Kaneko et al., Complete nucleotide sequence and molecular characterization of the temperate staphylococcal bacteriophage φPVL carrying Panton-Valentine leukocidin genes. *Gene* 215:57-67 (1998).

Ohnishi, K. (*Nucleic Acids Symp. Ser.*(1985), 16:253-256.

Sun et al. (*P.N.A.S. USA* (1994) 91:11462-11466.

Sun and Godson (*J. Mol. Biol.* (1998) 276(4):689-703).

Aravind L. et al. (*Nucleic Acid Research* (1998), 26(18):4205-4213).

Pan H. et al. (*Biochim. Biophys. Acta* (1999), 1444(3):429-433).

Sun et al. (*J. Bacteriol.* (1999) 181(12):3761-3767).

Keck et al. (*Science* (2000) 287(5462):2482-2486).

Podobnik (*J. Mol. Biol.* (2000) 300(2):353-362).

Frick and Richardson (*Annu. Rev. Biochem.* (2001) 70:39-80).

\* cited by examiner

FIGURE 1

SEQ ID NO: 1

>STAAU_R009 nucleotide sequence: 1800
TTGCGAATAGATCAATCGATCATTAATGAAATAAAAGATAAAACCGACATTTTAGACTTGGTAAGTGA
ATATGTAAAATTAGAAAAGAGAGGACGCAATTATATAGGTTTGTGTCCTTTTCATGATGAAAAGACAC
CTTCATTTACAGTTTCTGAAGATAAACAAATTTGTCATTGTTTTGGTTGTAAAAAAGGTGGCAATGTT
TTTCAATTTACTCAAGAAATTAAAGACATATCATTTGTTGAAGCGGTTAAAGAATTAGGTGATAGAGT
TAATGTTGCTGTAGATATTGAGGCAACACAATCTAACTCAAATGTTCAAATTGCTTCTGATGATTTAC
AAATGATTGAAATGCATGAGTTAATACAAGAATTTTATTATTACGCTTTAACAAAGACAGTCGAAGGC
GAACAAGCATTAACGTACTTACAAGAACGTGGTTTTACAGATGCGCTTATTAAAGAGCGAGGCATTGG
CTTTGCACCCGATAGCTCACATTTTTGTCATGATTTTCTTCAAAAAAAGGGTTACGATATTGAATTAG
CATATGAAGCCGGATTATTATCACGTAACGAAGAAAATTTCAGTTATTACGATAGATTTCGAAATCGT
ATTATGTTTCCTTTGAAAAATGCGCAAGGAAGAATTGTTGGATATTCAGGTCGAACATATACCGGTCA
AGAACCAAAATACTTAAATAGTCCTGAAACACCTATCTTTCAAAAAAGAAAGTTGTTATACAACTTAG
ATAAAGCGCGTAAATCAATTAGAAAATTAGATGAAATCGTATTACTAGAAGGTTTTATGGATGTTATA
AAATCTGATACTGCTGGCTTGAAAAACGTTGTTGCAACAATGGGTACACAGTTGTCAGATGAACATAT
TACTTTTATACGAAAGTTAACATCAAATATAACATTAATGTTTGATGGGGATTTTGCGGGTAGTGAAG
CAACACTTAAAACAGGTCAAAATTTGTTACAGCAAGGGCTAAATGTATTTGTTATACAATTGCCATCA
GGCATGGATCCGGATGAATACATTGGTAAGTATGGCAACGATGCATTTACTGCTTTTGTAAAAAATGA
CAAAAAGTCATTTGCACATTATAAAGTGAGTATATTAAAAGATGAAATTGCACATAATGACCTTTCAT
ATGAACGTTATTTGAAAGAACTAAGTCATGATATTTCGCTTATGAAATCATCGATTTTGCAACAAAAG
GCTTTAAATGATGTTGCACCATTTTTTCAATGTTAGTCCTGAGCAATTAGCTAACGAAATACAATTCAA
TCAAGCACCAGCCAATTATTATCCAGAAGATGAGTATGGCGGTTACATTGAACCTGAGCCAATTGGTA
TGGCACAATTTGACAATTTGAGCCGTCAAGAAAAAGCGGAGCGAGCATTTTTAAAACATTTAATGAGA
GATAAAGATACATTTTTAAATTATTATGAAAGTGTTGATAAGGATAACTTCACAAATCAGCATTTTAA
ATATGTATTCGAAGTCTTACATGATTTTTATGCGGAAAATGATCAATATAATATCAGTGATGCTGTGC
AGTATGTTAATTCAAATGAGTTGAGAGAAACACTAATTAGCTTAGAACAATATAATTTGAATGACGAA
CCATATGAAAATGAAATTGATGATTATGTCAATGTTATTAATGAAAAAGGACAAGAAACAATTGAGTC
ATTGAATCATAAATTAAGGGAAGCTACAAGGATTGGCGATGTAGAATTACAAAAATACTATTTACAGC
AAATTGTTGCTAAGAATAAAGAACGCATGTAG

SEQ ID NO: 2

>STAAU_R009 amino acid sequence : 599
LRIDQSIINEIKDKTDILDLVSEYVKLEKRGRNYIGLCPFHDEKTPSFTVSEDKQICHCFGCKKGGNV
FQFTQEIKDISFVEAVKELGDRVNVAVDIEATQSNSNVQIASDDLQMIEMHELIQEFYYYALTKTVEG
EQALTYLQERGFTDALIKERGIGFAPDSSHFCHDFLQKKGYDIELAYEAGLLSRNEENFSYYDRFRNR
IMFPLKNAQGRIVGYSGRTYTGQEPKYLNSPETPIFQKRKLLYNLDKARKSIRKLDEIVLLEGFMDVI
KSDTAGLKNVVATMGTQLSDEHITFIRKLTSNITLMFDGDFAGSEATLKTGQNLLQQGLNVFVIQLPS
GMDPDEYIGKYGNDAFTAFVKNDKKSFAHYKVSILKDEIAHNDLSYERYLKELSHDISLMKSSILQQK
ALNDVAPFFNVSPEQLANEIQFNQAPANYYPEDEYGGYIEPEPIGMAQFDNLSRQEKAERAFLKHLMR
DKDTFLNYYESVDKDNFTNQHFKYVFEVLHDFYAENDQYNISDAVQYVNSNELRETLISLEQYNLNDE
PYENEIDDYVNVINEKGQETIESLNHKLREATRIGDVELQKYYLQQIVAKNKERM

FIGURE 2

SEQ ID NO: 3

>96ORF078 nucleotide sequence
ATGAATATAATGCAATTCAAAAGCTTATTGAAATCGATGTATGAAGAGACAAAGCAAAGC
GACCCGATTGTAGCAAATGTATATATCGAGACTGGTTGGGCGGTCAATAGATTGTTGGAC
AATAACGAGTTATCGCCTTTCGATGATTACGACAGAGTTGAAAAGAAAATCATGAATGAA
ATCAACTGGAAGAAAACACACATTAAGGAGTGTTAA

SEQ ID NO: 4

>96ORF078 amino acid sequence 96_NT|10148-10363|
MNIMQFKSLLKSMYEETKQSDPIVANVYIETGWAVNRLLDNNELSPFDDYDRVEKKIMNE
INWKKTHIKEC

A.

FIGURE 5  96ORF78 (GST removed)

FIGURE 7A

A. Pfam HMM search results

| Model | Seq-from | Seq-to | HMM-from | HMM-to | Score | E-value |
|---|---|---|---|---|---|---|
| zf-CHC2 | 3 | 100 | 1 | 98 | 198.4 | 1.1e-55 |
| Toprim | 260 | 339 | 1 | 151 | 71.9 | 1.3e-17 |

Alignments of top-scoring domains:

```
zf-CHC2:
domain 1 of 1, from 3 to 100: score 198.4, E = 1.1e-55
                   *->ipeesIdeLknriDIVdviseYVkLkKkGrnYkgLCPFHdEKTPSFs
                      i++++I+e+k+++DI d++seYVkL+K+GrnY+gLCPFHdEKTPSF+
     gi|133988    3   IDQSIINEIKDKTDILDLVSEYVKLEKRGRNYIGLCPFHDEKTPSFT 49

VspeKqfYhCFGCGagGdaIkFlmkyeklsFvEAvekLAdragidlpyek
                   Vs +Kq+ hCFGC++gG+++ F ++++++sFvEAv++L dr+++ +++e
     gi|133988   50  VSEDKQICHCFGCKKGGNVFQFTQEIKDISFVEAVKELGDRVNVAVDIEA 99 g<-*
                   +
     gi|133988  100  T     100

Toprim: domain 1 of 1, from 260 to 339: score 71.9, E = 1.3e-17
                   *->kvliiVEgpsdakalakalgkpskrkivyelpggkdgnvvaslGhlv
                      +++++ Eg++d+++   a+              +nvva++G+
     gi|133988  260  DEIVLLEGFMDVIKSDTAGL----------------KNVVATMGTQ- 289 dLptpegyddkykwlwlpivdvkkgfepyqiefdqlckcskkidlkkeql
                                                                l++e++
     gi|133988  290  ----------------------------------------LSDEHI 295 kllkklakkadevilatDpDreGeaiawkllellkpygpveleddkkvrr
                   ++kl+++   + l++D+D +G ++++k  + l+ +g         +v++
     gi|133988  296  TFIRKLTSN---ITLMFDGDFAGSEATLKTGQNLLQQGL-------NVFV 335 iflp<-*
                   i+lp
     gi|133988  336  IQLP     339
```

FIGURE 7B/1

B.  Optimal global alignment of amino acid sequences

Sequence 1 sp|O05338|PRIM_STAAU DNA PRIMASE (EC 2.7.7.-) - S. aureus.(572 letters)
Sequence 2 STAAU_R009 STAAU_R009_NT|1-1800|(599 letters)

Identical: 560/605 (92%), similar: 564/605 (93%), Gap: 39/605 (6%)

```
seq1    1 M--------------------------- IGLCPFHDEKTPSFTVSEDKQICHCF         27
                                      ||||||||||||||||||||||||||
seq2    1 LRIDQSIINEIKDKTDILDLVSEYVKLEKRGRNYIGLCPFHDEKTPSFTVSEDKQICHCF    60 seq1   28 GCKKGGNVFQFTQEIKDISFVEAVKELGDRVNVAVDIEATQSNSNVQIASDDLQMIEMHE    87
          ||||||||||||||||||||||||||||||||||||||||||||||||||||||||||||
seq2   61 GCKKKGGNVFQFTQEIKDISFVEAVKELGDRVNVAVDIEATQSNSNVQIASDDLQMIEMHE  120 seq1   88 LIQEFYYALTKTVEGEQALTYLQERGFTDALIKERGIGFAPDSSHFCHDFLQKKGYDIE    147
          ||||||||||||||||||||||||||||||||||||||||||||||||||||||||||
seq2  121 LIQEFYYALTKTVEGEQALTYLQERGFTDALIKERGIGFAPDSSHFCHDFLQKKGYDIE    180 seq1  148 LAYEAGLLSRNEENFSYYDRFRNRIMFPLKNAQGRIVGYSGRTYTGQEPKYLNSPETPIF  207
          ||||||||||||||||||||||||||||||||||||||||||||||||||||||||||||
seq2  181 LAYEAGLLSRNEENFSYYDRFRNRIMFPLKNAQGRIVGYSGRTYTGQEPKYLNSPETPIF  240 seq1  208 QKRKLLYNLDKARKSIRKLDEIVLLEGFMDVIKSDTAGLKNVVATMGTQLSDEHITFIRK  267
          ||||||||||||||||||||||||||||||||||||||||||||||||||||||||||||
seq2  241 QKRKLLYNLDKARKSIRKLDEIVLLEGFMDVIKSDTAGLKNVVATMGTQLSDEHITFIRK  300 seq1  268 LTSNITLMFDGDFAGSEATLKTGQHLLQQGLNVFVIQLPSGMDPDEYIGKYGNDAFTTFV  327
          ||||||||||||||||||||||||||||||||||||||||||||||||||||||||||||
seq2  301 LTSNITLMFDGDFAGSEATLKTGQNLLQQGLNVFVIQLPSGMDPDEYIGKYGNDAFTAFV  360 seq1  328 KNDKKSFAHYKVSILKDEIAHNDLSYERYLKELSHDISLMKSSILQQKAINDVAPFFNVS  387
          ||||||||||||||||||||||||||||||||||||||||||||||||||||||||||||
seq2  361 KNDKKSFAHYKVSILKDEIAHNDLSYERYLKELSHDISLMKSSILQQKALNDVAPFFNVS  420 seq1  388 PEQLANEIQFNQAPANYYPEDEYGGYIEPEPIGMAQFDNLSRREKAERAFLKHL        447
          |||||||||||||||||||                            ||||||||||||
seq2  421 PEQLANEIQFNQAPANYYPE-----DEYGGYIEPEPIGMAQFDNLSRQEKAERAFLKHL   474
```

FIGURE 7B/2

```
seq1    448  MRDKDTFLNYYESVDKDNFTNQHFKYVFEVLHDFYAENDQYNISDAVQYVNSNELRETLI  507
             ||||||||||||||||||||||||||||||||||||||||||||||||||||||||||||
seq2    475  MRDKDTFLNYYESVDKDNFTNQHFKYVFEVLHDFYAENDQYNISDAVQYVNSNELRETLI  534 seq1    508  SLEQYNLNGEPYENEIDDYVNVINEKGQETIESLNHKLREATRIGDVELQKYYLQQIVAK  567
             |||||||| |||||||||||||||||||||||||||||||||||||||||||||||||||
seq2    535  SLEQYNLNDEPYENEIDDYVNVINEKGQETIESLNHKLREATRIGDVELQKYYLQQIVAK  594 seq1    568  NKERM  572
             |||||
seq2    595  NKERM  599

Sequence 1  STAAU_R009       (599 letters)
Sequence 2  gi|9910841|sp|Q9X4D0|PRIM_BACST DNA PRIMASE(597 letters)

Identical: 209/609 (34%), Similar: 315/609 (51%), Gap: 22/609 (3%)
seq1      1  L--RIDQSIINEIKDKTDILDLVSEYVKLEKRGRNYIGLCPFHDEKTPSFTVSEDKQICH   58
             :  ||     |||  ||: |||:|::  |||||||||||||||||:|| ::|| |
seq2      1  MGHRIPEETIEAIRRGVDIVDVIGEYVQLKRQGRNYFGLCPFHGEKTPSFSVSPEKQIFH   60 seq1     59  CFGCKKGGNVFQFTQEIKDISFVEAVKELGDRVNVAVDIEATQSNSNVQIASDDLQ-MIE  117
             ||||  |  |  ||  | ||| || :||||  | : :  ::|  |   ||  ||   |
seq2     61  CFGCGAGGNAFTFLMDIEGIPFVEAAKRLAAKAGVDLSVYELDVRGRDDGQTDEAKAMTE  120 seq1    118  MHELIQEFYYYALTKTVEGEQALTYLQERGFTDALIKERGIGFAPDSSHFCHDFLQKKGY  177
              |: || || | |||| |  ||||:|| ||||:|| |||| |   :|||
seq2    121  AHALLKRFYHHLLVHTKEGQAALDYLQARGWTKETIDRFEIGYAPDAPDAAAKLLESHSF  180 seq1    178  DIELAYEAGLLSRNEENFSYYDRFRNRIMFPLKNAQGRIVGYSGRTYTGQEPKYLNSPET  237
             : : |||:||:||  ::    |:||||||||| ||:|||:|||: ||||| ||:|||||
seq2    181  SLPVMEKAGLLTKKKEDG-RYVGRFRNRIMFPIHDHRGETVGFSGRLLGEGHPKYVNSPET  239
```

FIGURE 7B/3

```
seq1  238  PIFQKRKLLYNLDKARKSIRKLDEIVLLEGFMDVIKSDTAGLKNVVATMGTQLSDEHITF  297
           |:|| :||:  ||   ||   ||||   ::|:|| |||  :|||:  :|||||:::|
seq2  240  PVFRKGAILYHFHAARVPIRKRQEALLVEGFADVISAAQAGIDYAIATMGTSLTEEQARI  299 seq1  298  IRKLTSNITLMFDGDFAGSEATLKTGQNLLQQGLNVFVIQLPSGMDPDEYIGKYGNDAFT  357
           ||::|    ||:||||  | ::  ||:|||||||||||| |:|||||||    |||
seq2  300  LRP-CDTTICYDGDRAGIEAAWAAAEQLSALGCRVKVASLPNGLDPDEYIRVYGGERF-  357 seq1  358  AFVKNDKKSFAHYKVSILKDEIAHNDLSYE---RYLKELSHDISLMKSSILQQKALNDV  413
            :| ::  : |  |||:  :|:     :     |  |: ||: :|:||:|||:
seq2  358  AGEAGCRRPLVAFKMAYLR---RGKNLQHEGERLRYIDEALREIGKLSSPVEQDYYLRQL  414 seq1  414  APFFNVSPEQLANEIQFNQAPANYYPEDEYGGYIEPEPIGMAQFDNLSRQEKAERAFLKH  473
           | |: :: :  :|:|:   ::  : ||:|  : || ||  |||||  :||:
seq2  415  AEEFSLSLSALHEQLSRSQRERTKPREAPDGETARP----MLAKKLLPAFQNAERLLLAH  470 seq1  474  LMRDKDTFLNYYESVDKDNFTNQHFKYVFEVLHDFYAENDQYNISDAVQYVNSNELRETL  533
           ::  ::||:  ::  :   :|:: :::: ::  ::       ::|  |::: ::|
seq2  471  MMRSRDVALVVQERIG-GRFNIEEHRALAAYIYAFYEEGHEADPGALISRI-PGELQPLA  528 seq1  534  ISLEQYNLNDEPYENEIDDYV-NVINEKGQETIESLNHKLREATRIGDVELQKYYLQQIV  592
              : ||:|::   |:|:|    ::::  :| | |:||:  | ||:|::|::: :::
seq2  529  SDVSLLLIADDVSEQELEDYIRHVLNRPKWLMLKVKEQEKTEAERRKDFLTAARIAKEMI  588 seq1  593  AKNK--ERM  599 seq2  589  EMKKMLSSS  597
```

FIGURE 7B/4

```
Sequence 1    STAAU_R009 599 letters)
Sequence 2    gi|130904|sp|P05096|PRIM_BACSU DNA PRIMASE(603 letters)

Identical:  221/610 (36%),  Similar:  334/610 (54%),  Gap:  18/610 (2%)

seq1     1  L--RIDQSIINEIKDKTDILDLVSEYVKLEKRGRNYIGLCPFHDEKTPSFTVSEDKQICH       58
            :  ||||:.. :||:|: .| ::::. :||||  ||:|||:||  |||:||:|||||:|
seq2     1  MGNRIPDEIVDQVQKSADIVEVIGDYVQLKKQGRNYFGLCPFHGESTPSFSVSPDKQIFH       60 seq1    59  CFGCKKGGNVFQFTQEIKDISFVEAVKELGDRVNVAVDIEATQSNSNVQIASDDLQMIEM      118
            ||||  ||||| | :::  ..| ||:.|| |:  :.||  .|     ..:|: ::|  :
seq2    61  CFGCGAGGNVFSFLRQMEGYSFAESVSHLADKYQIDFPDDITVHSGARPESSGEQKMAEA      120 seq1   119  HELIQEFYYALTKTVEGEQALTYLQERGFTDALIKERGIGFAPDSSHFCHDFLQKKGYD       178
            ||| :||  : :.|.|.|:||| |:|  |..| :|.||  :|.| ..| ||| :|:|
seq2   121  HELLKKFYHHLLINTKEGQEALDYLLSRGFTKELINEFQIGYALDSWDFITKFLVKRGFS      180 seq1   179  IELAYEAGLLSRNEENFSYYDRFRNRIMFPLKNAQGRIVGYSGRTYTGQEPKYLNSPETP      238
            .::|   ||:.|  ::||| ||||| ||| :.  | :|:  .| | |||||:.||||
seq2   181  EAQMEKAGLLIRREDGSYFDRFRNRVMFPIHDHHGAVVAFSGRALGSQQPKYMNSPETP      240 seq1   239  IFQKRKLLYNLDKARKSIRKLDEIVLLEGFMDVIKSDTAGLKNVVATMGTQLSDEHITFI      298
             |::|||||| :|  :   .::     ||:|::: ::  :|:||| :.|||||:::| :
seq2   241  LFHKSKLLYNFYYKARLHIRKQERAVLFEGFADVYTAVSSDVKESIATMGTSLTDDHVKIL      300 seq1   299  RKLTSNITLMFPDGDFAGSEATLKTGQNLLQQGLNVFVIQLPSGMDPDEYIGKYGNDAFTA      358
             | :.   ||: |.|:| :|:  ||.|:| |.|. |: :|| | ||.||:||: : .
seq2   301  RRNVEEIILCYDSDKAGYEATLKASELLQKKGCKVRVAMIPDGLDPDDYIKKFGGEKFKN      360 seq1   359  FVKNDKKSFAHYKVSIL-KDEIAHNDLSYERYLKELSHDISLMKSSILQQKALNDVAPFF      417
            :: |::||   |:   | |||   ||.|.::. ::::...| |   | .:     :|
seq2   361  DIIDASVTVMAFKMQYFRKGKNLSDEGDRLAYIKDVLKEISTLSGSLEQEVYVKQLASEF      420 seq1   418  NVSPEQLANEIQFNQAPANYYPEDEYGGYIEPEPIGMAQFDNLSRQ------EKAERAF      470
            .::    :|:  |         :  |                 ||        ::|
seq2   421  SLSQESLTE--QLSVFSKQNKPADNSG----ETKTRRAHLTTKARQKRLRPAYENAERLL      474
```

FIGURE 7B/5

```
seq1  471  LKHLMRDKDTFLNYYESVDKDNFTNQHFKYVFEVLHDFYAENDQYNISDAVQYVNSNELR   530
           |  |:::|:  :      :    :  |:  ||  :  :||
seq2  475  LAHMLRDRSVIKKVIDRVGQFNIDEH-RALAAVLYAFYEBGAELTPQHLMARVTDDHIS   533 seq1  531  ETLISLEQYNLNDEPYENEIDDYV-NVINEKGQETIESLNHKLREATRIGDVELQKYYLQ   589
           :  :||||| :  | :  |::  |||  :   ::     |||
seq2  534  QLLSDILMLQVNQELSEAELSDYVKKVLNQRNWSMIKEKEAEAERQKDFLRAASLAQ---  593 seq1  590  QIVAKNKERM   599
           :|:  :
seq2  594  EIVTLNRSLK   603

Sequence 1 STAAU_R009 (599 letters)
Sequence 2 gi|130908|sp|P02923|PRIM_ECOLI DNA PRIMASE (581 letters)

Identical: 170/619 (27%), Similar: 294/619 (47%), Gap: 58/619 (9%)

seq1    1  L--RIDQSIINEIKDKTDILDLVSEYVKLEKRGRNYIGLCPFHDEKTPSFTVSEDKQICH   58
           :  ||:::  |||::||  :||||:||  :|::|  ||::|||||||||
seq2    1  MAGRIPRVFINDLLARTDIVDLIDARVKLKKQGKNFHACCPFHNEKTPSFTVNGEKQFYH   60 seq1   59  CFGCKKGGNVFQFTQEIKDISFVEAVKELGDRVNVAVDIEATQSNSNVQIASDDLQMIEM   118
           ||||  | ||  :    :  |:  |   ||   :: ||  :   ::
seq2   61  CFGCGAHGNAIDFLMNYDKLEFVETVEELAAMHNLEVPFEAGSGPSQIE-RHQRQTLYQL   119 seq1  119  HELIQEFYYYALTKTVEGEQALTYLQERGFTDALIKERGIGFAPDSSHFCHDFLQKKGYD   178
           |:| :||  :  | |:||  :  :||:|||  :||:||  :|||
seq2  120  MDGLNTFYQQSLQQPV-ATSARQYLEKRGLSHEVIARFAIGFAPPG--WDNVLKRFGGN   175 seq1  179  IE--LAYEAGLLSRNEENFSYYDRFRNRIMFPLKNAQGRIVGYSGRTYTGQEPKYLNSP   235
           ||  |    :   |  :||||  :|| :||||  ||  ::||  ||  |||||||||
seq2  176  PENRQSLIDAGMLVTNDQGRS-YDRFRERVMFPIRDKRGRVIGFGGRVLGNDTPKYLNSP   234 seq1  236  ETPIFQKRKLLYNLDKARKSIRKLDEIVLLEGFMDVIKSDTAGLKNVVATMGTQLSDEHI   295
           |||||  |:|||  ||:   | :  :::||:||| | :|  :|| | |
seq2  235  ETDIFHKGRQLYGLYEAQQDNAEPNRLLVVEGYMDVVALAQYGINYAVASLGTSTTADHI   294
```

FIGURE 7B/6

```
seq1  296  TFIRKLTSNITLMFDGDFAGSEA---TLKTGQNLLQQGLNVFVIQLPSGMDPDEYIGKYG  352
              :   : |    ||||||  ::|      ||:||||||||||||||  ||||||||
seq2  295  QLLFRATNNVICCYDGDRAGRDAAWRALETALPYMTDGRQLRFMFLPDGEDPDTLVRKEG  354 seq1  353  NDAFTAFVKNDKKSFAHYKVSILKDEIAHNDLSYERYLKELSHDISLMKSSILQQKALND  412
             ||                      ||   :|     ::    ||  ::
seq2  355  KEAFEARMEQAMPLSAFLFNSLMPQV----DLS----TPDGRARLSTLALPLISQVPGET  406 seq1  413  VAPFFNVSPEQLANEIQF--NQAPANYYPEDEYGGYIEPEPIGMAQFDNLSRQEKAERAF  470
            :    :          |:|  :                                 |
seq2  407  LRIYLR---QELGNKLGILDDSQLERLMPKAAESGVSRPVP-----------QLKRTTMRIL  454 seq1  471  LKHLMRDKD--TFLNYYESVDKDNFTNQHFKYVFEVLHDFYAENDQYNISDAVQYVNSNE  528
              : ::          :|:|                  ::
seq2  455  IGLLVQNPELATLVPPLENLDENKLPGLG--LFRELVNTCLSQPGLTTGQLLEHYRGTN  511 seq1  529  LRETLISLEQY------NLNDEPYENEIDDYVNVINEKGQETIESLNHKLREATR--IGD  580
             |:  :: |:  |::                       ::::
seq2  512  NAATLEKLSMWDDIADKNIAEQTFTDSLNHMFDSLLELRQEELIA-----RERTHGLSNE  566 seq1  581  VELQKYYLQQIVAKNKERM  599
             ::|: :   ||:|
seq2  567  ERLELWTLNQELAKK----  581
```

FIGURE 9
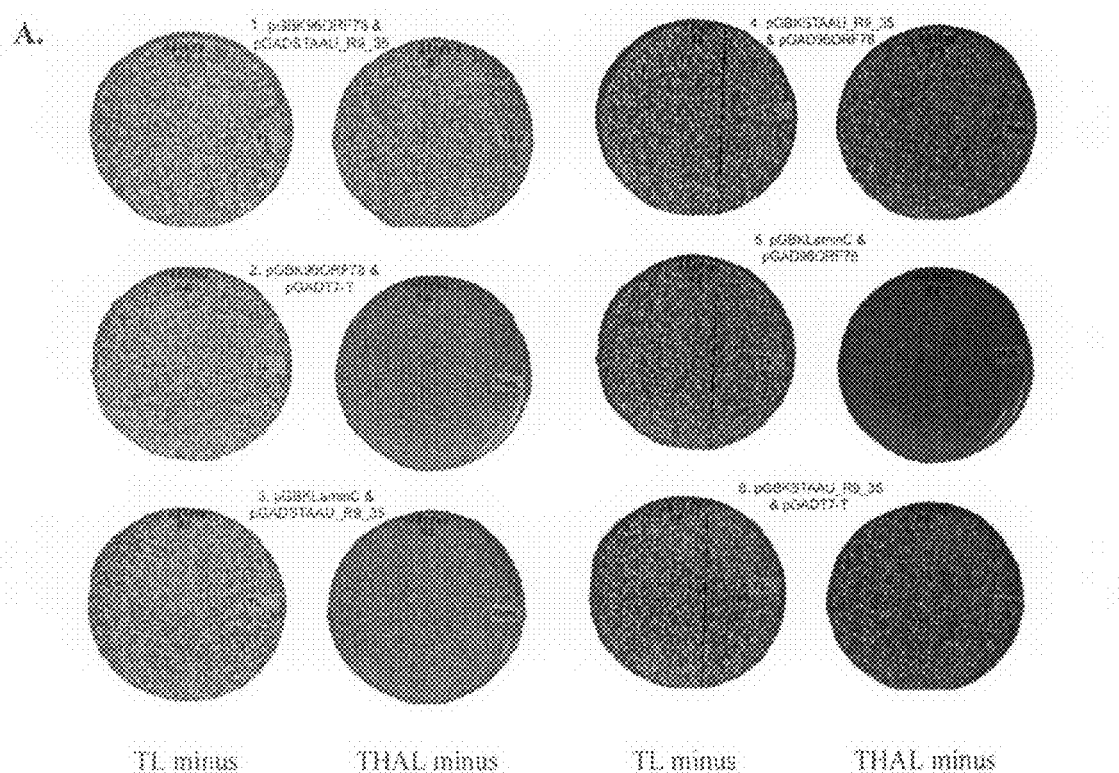
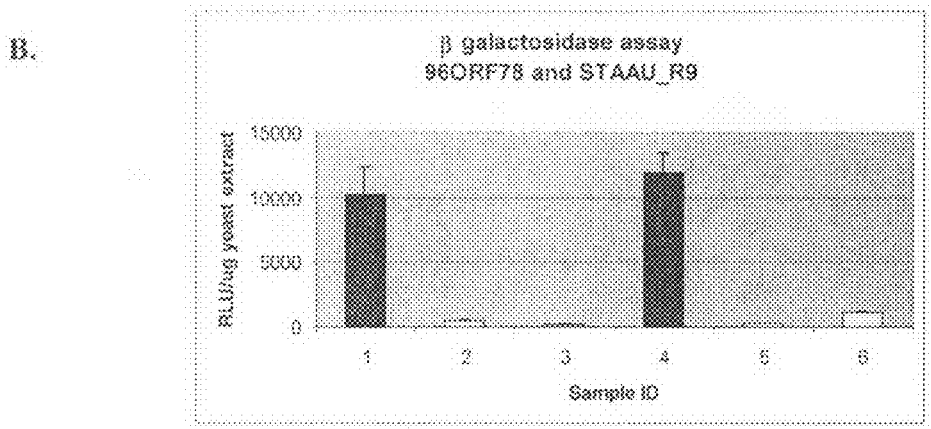
| Sample | Yeast co-transformants | | RLU (avg) | SD |
|---|---|---|---|---|
| | Plasmid 1 | Plasmid 2 | | |
| 1 | pGBK 96ORF78 | pGADSTAAU_R9_35 | 10,250 | 2,080 |
| 2 | pGBK 96ORF78 | pGADT7-T | 475 | 38 |
| 3 | pGBK Lamin C | pGADSTAAU_R9_35 | 224 | 10 |
| 4 | pGBKSTAAU_R9_35 | pGAD 96ORF78 | 11,935 | 1,477 |
| 5 | pGBK Lamin C | pGAD 96ORF78 | 243 | 12 |
| 6 | pGBKSTAAU_R9_35 | pGADT7-T | 1,121 | 37 |

Figure 11 A.

|  | Primer name | Primer sequence | Restriction site |
|---|---|---|---|
| SEQ ID NO: 8 | R9_5E3 | 5'-ccggaattcTTGCGAATAGATCAATCG-3' | EcoRI |
| SEQ ID NO: 9 | R9_3BG | 5'-ggaagatctCTACATGCGTTCTTTATTC-3' | BglII |
| SEQ ID NO: 10 | R9_5E | 5'-ccggaattcATGATAGGTTTGTGTCCT-3' | EcoRI |
| SEQ ID NO: 11 | R9_5E1 | 5'-ccggaattcCCAAAATACCTAAATAGTCC-3' | EcoRI |
| SEQ ID NO: 12 | R9_5E2 | 5'-ccggaattcGCACATAATGACCTTTCA-3' | EcoRI |
| SEQ ID NO: 13 | R9_342R | 5'-cgcggatccATGCCTGATGGCAATTG-3' | BamHI |
| SEQ ID NO: 14 | R9_402R | 5'-ccatcgatGATTTCATAAGCGAAATATC-3' | ClaI |
| SEQ ID NO: 15 | R9_449F | 5'-ccggaattcCCTGAGCCAATTGGTATGGC-3' | EcoRI |
| SEQ ID NO: 16 | R9_449R | 5'-cgcggatccctaAGGTTCAATGTAACCGCC-3' | BamHI |
| SEQ ID NO: 17 | R9_490F | 5'-ccggaattcAAGGATAACTTCACAAATCAG-3' | EcoRI |
| SEQ ID NO: 18 | R9_490R | 5'-cgcggatccctaCTTATCAACACTTTCATAATA-3' | BamHI |
| SEQ ID NO: 19 | R9_530F | 5'-ccggaattcAGAGAAACACTAATTAGCTTA-3' | EcoRI |
| SEQ ID NO: 20 | R9_530R | 5'-cgcggatccctaTCTCAACTCATTTGAATTAAC-3' | BamHI |
| SEQ ID NO: 21 | R9_561F | 5'-ccggaattcGGACAAGAAACAATTGAGTC-3' | EcoRI |
| SEQ ID NO: 7 | R9_561R | 5'-cgcggatccctaTCCTTTTTCATTAATAACATTG-3' | BamHI |

Figure 11 B.

| Cloning of SEQ ID NO: 2 amino acid fragments | Sense primer | Antisense primer |
|---|---|---|
| 1-599 | R9_5E3 | R9_3BG |
| 35-599 | R9_5E | R9_3BG |
| 35-342 | R9_5E | R9_342R |
| 229-402 | R9_5E1 | R9_402R |
| 229-599 | R9_5E1 | R9_3BG |
| 380-599 | R9_5E2 | R9_3BG |
| 380-449 | R9_5E2 | R9_449R |
| 380-490 | R9_5E2 | R9_490R |
| 380-530 | R9_5E2 | R9_530R |
| 380-561 | R9_5E2 | R9_561R |
| 449-599 | R9_449F | R9_3BG |
| 490-599 | R9_490F | R9_3BG |
| 530-599 | R9_530F | R9_3BG |
| 561-599 | R9_561F | R9_3BG |

SEQUENCE LISTING

```
<160> NUMBER OF SEQ ID NOS: 41

<210> SEQ ID NO 1
<211> LENGTH: 1800
<212> TYPE: DNA
<213> ORGANISM: Staphylococcus aureus

<400> SEQUENCE: 1
ttgcgaatag atcaatcgat cattaatgaa ataaaagata aaaccgacat tttagacttg      60
gtaagtgaat atgtaaaatt agaaaagaga ggacgcaatt atataggttt gtgtcctttt     120
catgatgaaa agacaccttc atttacagtt tctgaagata aacaaatttg tcattgtttt     180
ggttgtaaaa aaggtggcaa tgtttttcaa tttactcaag aaattaaaga catatcattt     240
gttgaagcgg ttaaagaatt aggtgataga gttaatgttg ctgtagatat tgaggcaaca     300
caatctaact caaatgttca aattgcttct gatgatttac aaatgattga aatgcatgag     360
ttaatacaag aattttatta ttacgcttta acaaagacag tcgaaggcga acaagcatta     420
acgtacttac aagaacgtgg ttttacagat gcgcttatta aagagcgagg cattggcttt     480
gcacccgata gctcacattt ttgtcatgat tttcttcaaa aaaagggtta cgatattgaa     540
ttagcatatg aagccggatt attatcacgt aacgaagaaa atttcagtta ttacgataga     600
```

-continued

```
tttcgaaatc gtattatgtt tcctttgaaa aatgcgcaag gaagaattgt tggatattca    660
ggtcgaacat ataccggtca agaaccaaaa tacttaaata gtcctgaaac acctatcttt    720
caaaaaagaa agttgttata caacttagat aaagcgcgta atcaattag aaaattagat    780
gaaatcgtat tactagaagg ttttatggat gttataaaat ctgatactgc tggcttgaaa    840
aacgttgttg caacaatggg tacacagttt tcagatgaac atattacttt tatacgaaag    900
ttaacatcaa atataacatt aatgtttgat ggggattttg cgggtagtga agcaacactt    960
aaaacaggtc aaaatttgtt acagcaaggg ctaaatgtat tgttatacaa attgccatca   1020
ggcatggatc cggatgaata cattggtaag tatggcaacg atgcatttac tgcttttgta   1080
aaaaatgaca aaagtcatt tgcacattat aaagtgagta tattaaaaga tgaaattgca   1140
cataatgacc tttcatatga acgttatttg aaagaactaa gtcatgatat ttcgcttatg   1200
aaatcatcga ttttgcaaca aaaggcttta aatgatgttg caccatttt caatgttagt   1260
cctgagcaat tagctaacga aatacaattc aatcaagcac cagccaatta ttatccagaa   1320
gatgagtatg gcggttacat tgaacctgag ccaattggta tggcacaatt tgacaatttg   1380
agccgtcaag aaaagcgga gcgagcattt taaaacatt aatgagaga taagataca    1440
tttttaaatt attatgaaag tgttgataag gataacttca caaatcagca ttttaaatat   1500
gtattcgaag tcttcatga tttttatgcg gaaaatgatc aatataatat cagtgatgct   1560
gtgcagtatg ttaattcaaa tgagttgaga gaaacactaa ttagcttaga acaatataat   1620
ttgaatgacg aaccatatga aaatgaaatt gatgattatg tcaatgttat taatgaaaaa   1680
ggacaagaaa caattgagtc attgaatcat aaattaaggg aagctacaag gattggcgat   1740
gtagaattac aaaaatacta tttacagcaa attgttgcta agaataaaga acgcatgtag   1800
```

<210> SEQ ID NO 2
<211> LENGTH: 599
<212> TYPE: PRT
<213> ORGANISM: Staphylococcus aureus

<400> SEQUENCE: 2

```
Leu Arg Ile Asp Gln Ser Ile Ile Asn Glu Ile Lys Asp Lys Thr Asp
  1               5                  10                  15

Ile Leu Asp Leu Val Ser Glu Tyr Val Lys Leu Glu Lys Arg Gly Arg
             20                  25                  30

Asn Tyr Ile Gly Leu Cys Pro Phe His Asp Glu Lys Thr Pro Ser Phe
         35                  40                  45

Thr Val Ser Glu Asp Lys Gln Ile Cys His Cys Phe Gly Cys Lys Lys
     50                  55                  60

Gly Gly Asn Val Phe Gln Phe Thr Gln Glu Ile Lys Asp Ile Ser Phe
 65                  70                  75                  80

Val Glu Ala Val Lys Glu Leu Gly Asp Arg Val Asn Val Ala Val Asp
                 85                  90                  95

Ile Glu Ala Thr Gln Ser Asn Ser Asn Val Gln Ile Ala Ser Asp Asp
            100                 105                 110

Leu Gln Met Ile Glu Met His Glu Leu Ile Gln Glu Phe Tyr Tyr Tyr
        115                 120                 125

Ala Leu Thr Lys Thr Val Glu Gly Glu Gln Ala Leu Thr Tyr Leu Gln
    130                 135                 140

Glu Arg Gly Phe Thr Asp Ala Leu Ile Lys Glu Arg Gly Ile Gly Phe
145                 150                 155                 160

Ala Pro Asp Ser Ser His Phe Cys His Asp Phe Leu Gln Lys Lys Gly
```

```
                    165                 170                 175
Tyr Asp Ile Glu Leu Ala Tyr Glu Ala Gly Leu Leu Ser Arg Asn Glu
                180                 185                 190

Glu Asn Phe Ser Tyr Tyr Asp Arg Phe Arg Asn Arg Ile Met Phe Pro
            195                 200                 205

Leu Lys Asn Ala Gln Gly Arg Ile Val Gly Tyr Ser Gly Arg Thr Tyr
        210                 215                 220

Thr Gly Gln Glu Pro Lys Tyr Leu Asn Ser Pro Glu Thr Pro Ile Phe
225                 230                 235                 240

Gln Lys Arg Lys Leu Leu Tyr Asn Leu Asp Lys Ala Arg Lys Ser Ile
                245                 250                 255

Arg Lys Leu Asp Glu Ile Val Leu Leu Glu Gly Phe Met Asp Val Ile
            260                 265                 270

Lys Ser Asp Thr Ala Gly Leu Lys Asn Val Val Ala Thr Met Gly Thr
        275                 280                 285

Gln Leu Ser Asp Glu His Ile Thr Phe Ile Arg Lys Leu Thr Ser Asn
290                 295                 300

Ile Thr Leu Met Phe Asp Gly Asp Phe Ala Gly Ser Glu Ala Thr Leu
305                 310                 315                 320

Lys Thr Gly Gln Asn Leu Leu Gln Gln Gly Leu Asn Val Phe Val Ile
                325                 330                 335

Gln Leu Pro Ser Gly Met Asp Pro Asp Glu Tyr Ile Gly Lys Tyr Gly
            340                 345                 350

Asn Asp Ala Phe Thr Ala Phe Val Lys Asn Asp Lys Lys Ser Phe Ala
        355                 360                 365

His Tyr Lys Val Ser Ile Leu Lys Asp Glu Ile Ala His Asn Asp Leu
    370                 375                 380

Ser Tyr Glu Arg Tyr Leu Lys Glu Leu Ser His Asp Ile Ser Leu Met
385                 390                 395                 400

Lys Ser Ser Ile Leu Gln Gln Lys Ala Leu Asn Asp Val Ala Pro Phe
                405                 410                 415

Phe Asn Val Ser Pro Glu Gln Leu Ala Asn Glu Ile Gln Phe Asn Gln
            420                 425                 430

Ala Pro Ala Asn Tyr Tyr Pro Glu Asp Glu Tyr Gly Gly Tyr Ile Glu
        435                 440                 445

Pro Glu Pro Ile Gly Met Ala Gln Phe Asp Asn Leu Ser Arg Gln Glu
    450                 455                 460

Lys Ala Glu Arg Ala Phe Leu Lys His Leu Met Arg Asp Lys Asp Thr
465                 470                 475                 480

Phe Leu Asn Tyr Tyr Glu Ser Val Asp Lys Asp Asn Phe Thr Asn Gln
                485                 490                 495

His Phe Lys Tyr Val Phe Glu Val Leu His Asp Phe Tyr Ala Glu Asn
            500                 505                 510

Asp Gln Tyr Asn Ile Ser Asp Ala Val Gln Tyr Val Asn Ser Asn Glu
        515                 520                 525

Leu Arg Glu Thr Leu Ile Ser Leu Glu Gln Tyr Asn Leu Asn Asp Glu
    530                 535                 540

Pro Tyr Glu Asn Glu Ile Asp Asp Tyr Val Asn Val Ile Asn Glu Lys
545                 550                 555                 560

Gly Gln Glu Thr Ile Glu Ser Leu Asn His Lys Leu Arg Glu Ala Thr
                565                 570                 575

Arg Ile Gly Asp Val Glu Leu Gln Lys Tyr Tyr Leu Gln Gln Ile Val
            580                 585                 590
```

Ala Lys Asn Lys Glu Arg Met
       595

<210> SEQ ID NO 3
<211> LENGTH: 216
<212> TYPE: DNA
<213> ORGANISM: Staphylococcus aureus

<400> SEQUENCE: 3
atgaatataa tgcaattcaa aagcttattg aaatcgatgt atgaagagac aaagcaaagc     60
gacccgattg tagcaaatgt atatatcgag actggttggg cggtcaatag attgttggac    120
aataacgagt tatcgccttt cgatgattac gacagagttg aaaagaaaat catgaatgaa    180
atcaactgga agaaaacaca cattaaggag tgttaa                              216

<210> SEQ ID NO 4
<211> LENGTH: 71
<212> TYPE: PRT
<213> ORGANISM: Staphylococcus aureus

<400> SEQUENCE: 4

Met Asn Ile Met Gln Phe Lys Ser Leu Leu Lys Ser Met Tyr Glu Glu
 1               5                  10                  15

Thr Lys Gln Ser Asp Pro Ile Val Ala Asn Val Tyr Ile Glu Thr Gly
            20                  25                  30

Trp Ala Val Asn Arg Leu Leu Asp Asn Asn Glu Leu Ser Pro Phe Asp
        35                  40                  45

Asp Tyr Asp Arg Val Glu Lys Lys Ile Met Asn Glu Ile Asn Trp Lys
    50                  55                  60

Lys Thr His Ile Lys Glu Cys
65                  70

<210> SEQ ID NO 5
<211> LENGTH: 120
<212> TYPE: DNA
<213> ORGANISM: Staphylococcus aureus

<400> SEQUENCE: 5
ggacaagaaa caattgagtc attgaatcat aaattaaggg aagctacaag gattggcgat     60
gtagaattac aaaaatacta tttacagcaa attgttgcta agaataaaga acgcatgtag    120

<210> SEQ ID NO 6
<211> LENGTH: 39
<212> TYPE: PRT
<213> ORGANISM: Staphylococcus aureus

<400> SEQUENCE: 6

Gly Gln Glu Thr Ile Glu Ser Leu Asn His Lys Leu Arg Glu Ala Thr
 1               5                  10                  15

Arg Ile Gly Asp Val Glu Leu Gln Lys Tyr Tyr Leu Gln Gln Ile Val
            20                  25                  30

Ala Lys Asn Lys Glu Arg Met
        35

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Primer

```
<400> SEQUENCE: 7
cgcggatccc tatccttttt cattaataac attg                          34

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 8
ccggaattct tgcgaataga tcaatcg                                  27

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 9
ggaagatctc tacatgcgtt ctttattc                                 28

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 10
ccggaattca tgataggttt gtgtcct                                  27

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 11
ccggaattcc caaaatacct aaatagtcc                                29

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 12
ccggaattcg cacataatga cctttca                                  27

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 13
cgcggatcca tgcctgatgg caattg                                   26

<210> SEQ ID NO 14
```

```
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 14
ccatcgatga tttcataagc gaaatatc                                         28

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 15
ccggaattcc ctgagccaat tggtatggc                                        29

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 16
cgcggatccc taaggttcaa tgtaaccgcc                                       30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 17
ccggaattca aggataactt cacaaatcag                                       30

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 18
cgcggatccc tacttatcaa cactttcata ata                                   33

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 19
ccggaattca gagaaacact aattagctta                                       30

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 20
```

```
cgcggatccc tatctcaact catttgaatt aac                                  33
```

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 21

```
ccggaattcg gacaagaaac aattgagtc                                       29
```

<210> SEQ ID NO 22
<211> LENGTH: 581
<212> TYPE: PRT
<213> ORGANISM: Escherichia coli

<400> SEQUENCE: 22

```
Met Ala Gly Arg Ile Pro Arg Val Phe Ile Asn Asp Leu Leu Ala Arg
  1               5                  10                  15

Thr Asp Ile Val Asp Leu Ile Asp Ala Arg Val Lys Leu Lys Lys Gln
             20                  25                  30

Gly Lys Asn Phe His Ala Cys Cys Pro Phe His Asn Glu Lys Thr Pro
         35                  40                  45

Ser Phe Thr Val Asn Gly Glu Lys Gln Phe Tyr His Cys Phe Gly Cys
     50                  55                  60

Gly Ala His Gly Asn Ala Ile Asp Phe Leu Met Asn Tyr Asp Lys Leu
 65                  70                  75                  80

Glu Phe Val Glu Thr Val Glu Glu Leu Ala Ala Met His Asn Leu Glu
                 85                  90                  95

Val Pro Phe Glu Ala Gly Ser Gly Pro Ser Gln Ile Glu Arg His Gln
            100                 105                 110

Arg Gln Thr Leu Tyr Gln Leu Met Asp Gly Leu Asn Thr Phe Tyr Gln
        115                 120                 125

Gln Ser Leu Gln Gln Pro Val Ala Thr Ser Ala Arg Gln Tyr Leu Glu
    130                 135                 140

Lys Arg Gly Leu Ser His Glu Val Ile Ala Arg Phe Ala Ile Gly Phe
145                 150                 155                 160

Ala Pro Pro Gly Trp Asp Asn Val Leu Lys Arg Phe Gly Gly Asn Pro
                165                 170                 175

Glu Asn Arg Gln Ser Leu Ile Asp Ala Gly Met Leu Val Thr Asn Asp
            180                 185                 190

Gln Gly Arg Ser Tyr Asp Arg Phe Arg Glu Arg Val Met Phe Pro Ile
        195                 200                 205

Arg Asp Lys Arg Gly Arg Val Ile Gly Phe Gly Gly Arg Val Leu Gly
    210                 215                 220

Asn Asp Thr Pro Lys Tyr Leu Asn Ser Pro Glu Thr Asp Ile Phe His
225                 230                 235                 240

Lys Gly Arg Gln Leu Tyr Gly Leu Tyr Glu Ala Gln Gln Asp Asn Ala
                245                 250                 255

Glu Pro Asn Arg Leu Leu Val Val Glu Gly Tyr Met Asp Val Val Ala
            260                 265                 270

Leu Ala Gln Tyr Gly Ile Asn Tyr Ala Val Ala Ser Leu Gly Thr Ser
        275                 280                 285

Thr Thr Ala Asp His Ile Gln Leu Leu Phe Arg Ala Thr Asn Asn Val
    290                 295                 300
```

```
Ile Cys Cys Tyr Asp Gly Asp Arg Ala Gly Arg Asp Ala Ala Trp Arg
305                 310                 315                 320

Ala Leu Glu Thr Ala Leu Pro Tyr Met Thr Asp Gly Arg Gln Leu Arg
            325                 330                 335

Phe Met Phe Leu Pro Asp Gly Glu Asp Pro Asp Thr Leu Val Arg Lys
        340                 345                 350

Glu Gly Lys Glu Ala Phe Glu Ala Arg Met Glu Gln Ala Met Pro Leu
    355                 360                 365

Ser Ala Phe Leu Phe Asn Ser Leu Met Pro Gln Val Asp Leu Ser Thr
370                 375                 380

Pro Asp Gly Arg Ala Arg Leu Ser Thr Leu Ala Leu Pro Leu Ile Ser
385                 390                 395                 400

Gln Val Pro Gly Glu Thr Leu Arg Ile Tyr Leu Arg Gln Glu Leu Gly
                405                 410                 415

Asn Lys Leu Gly Ile Leu Asp Asp Ser Gln Leu Glu Arg Leu Met Pro
            420                 425                 430

Lys Ala Ala Glu Ser Gly Val Ser Arg Pro Val Pro Gln Leu Lys Arg
        435                 440                 445

Thr Thr Met Arg Ile Leu Ile Gly Leu Leu Val Gln Asn Pro Glu Leu
    450                 455                 460

Ala Thr Leu Val Pro Pro Leu Glu Asn Leu Asp Glu Asn Lys Leu Pro
465                 470                 475                 480

Gly Leu Gly Leu Phe Arg Glu Leu Val Asn Thr Cys Leu Ser Gln Pro
                485                 490                 495

Gly Leu Thr Thr Gly Gln Leu Leu Glu His Tyr Arg Gly Thr Asn Asn
            500                 505                 510

Ala Ala Thr Leu Glu Lys Leu Ser Met Trp Asp Asp Ile Ala Asp Lys
        515                 520                 525

Asn Ile Ala Glu Gln Thr Phe Thr Asp Ser Leu Asn His Met Phe Asp
530                 535                 540

Ser Leu Leu Glu Leu Arg Gln Glu Glu Leu Ile Ala Arg Glu Arg Thr
545                 550                 555                 560

His Gly Leu Ser Asn Glu Glu Arg Leu Glu Leu Trp Thr Leu Asn Gln
                565                 570                 575

Glu Leu Ala Lys Lys
            580

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 23
ccgctcgagc tccaaattcc aaaacag                                         27

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 24
cgggatccaa taagactcct ttttac                                          26
```

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 25
gcgcatctgt aaaaccacg                                              19

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 26
gcacgaattc aagaagaatt g                                           21

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gatctcgtcg tgcatctgtt ggatccccgg aattcccggg                       40

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tcgacccggg aattccgggg atccaacaga tgcacgacga                       40

<210> SEQ ID NO 29
<211> LENGTH: 9
<212> TYPE: PRT
<213> ORGANISM: Staphylococcus aureus

<400> SEQUENCE: 29

Tyr Tyr Leu Gln Gln Ile Val Ala Lys
 1               5

<210> SEQ ID NO 30
<211> LENGTH: 10
<212> TYPE: PRT
<213> ORGANISM: Staphylococcus aureus

<400> SEQUENCE: 30

Glu Leu Ser His Asp Ile Ser Leu Met Lys
 1               5                  10

<210> SEQ ID NO 31
<211> LENGTH: 10
<212> TYPE: PRT
<213> ORGANISM: Staphylococcus aureus

<400> SEQUENCE: 31

```
Ile Asp Gln Ser Ile Ile Asn Glu Ile Lys
 1               5                  10

<210> SEQ ID NO 32
<211> LENGTH: 11
<212> TYPE: PRT
<213> ORGANISM: Staphylococcus aureus

<400> SEQUENCE: 32

Gly Gln Glu Thr Ile Glu Ser Leu Asn His Lys
 1               5                  10

<210> SEQ ID NO 33
<211> LENGTH: 10
<212> TYPE: PRT
<213> ORGANISM: Staphylococcus aureus

<400> SEQUENCE: 33

Asn Glu Glu Asn Phe Ser Tyr Tyr Asp Arg
 1               5                  10

<210> SEQ ID NO 34
<211> LENGTH: 12
<212> TYPE: PRT
<213> ORGANISM: Staphylococcus aureus

<400> SEQUENCE: 34

Tyr Leu Asn Ser Pro Glu Thr Pro Ile Phe Gln Lys
 1               5                  10

<210> SEQ ID NO 35
<211> LENGTH: 16
<212> TYPE: PRT
<213> ORGANISM: Staphylococcus aureus

<400> SEQUENCE: 35

Lys Gly Tyr Asp Ile Glu Leu Ala Tyr Glu Ala Gly Leu Leu Ser Arg
 1               5                  10                  15

<210> SEQ ID NO 36
<211> LENGTH: 17
<212> TYPE: PRT
<213> ORGANISM: Staphylococcus aureus

<400> SEQUENCE: 36

Val Ser Ile Leu Lys Asp Glu Ile Ala His Asn Asp Leu Ser Tyr Glu
 1               5                  10                  15

Arg

<210> SEQ ID NO 37
<211> LENGTH: 98
<212> TYPE: PRT
<213> ORGANISM: Unknown Organism
<220> FEATURE:
<223> OTHER INFORMATION: Description of Unknown Organism: Illustrative
      zf-CHC2 comparison peptide

<400> SEQUENCE: 37

Ile Pro Glu Glu Ser Ile Asp Glu Leu Lys Asn Arg Ile Asp Ile Val
 1               5                  10                  15

Asp Val Ile Ser Glu Tyr Val Lys Leu Lys Lys Gly Arg Asn Tyr
                20                  25                  30

Lys Gly Leu Cys Pro Phe His Asp Glu Lys Thr Pro Ser Phe Ser Val
```

```
                35                  40                  45
Ser Pro Glu Lys Gln Phe Tyr His Cys Phe Gly Cys Gly Ala Gly Gly
 50                  55                  60

Asp Ala Ile Lys Phe Leu Met Lys Tyr Glu Lys Leu Ser Phe Val Glu
 65                  70                  75                  80

Ala Val Glu Lys Leu Ala Asp Arg Ala Gly Ile Asp Leu Pro Tyr Glu
                 85                  90                  95

Lys Gly

<210> SEQ ID NO 38
<211> LENGTH: 151
<212> TYPE: PRT
<213> ORGANISM: Unknown Organism
<220> FEATURE:
<223> OTHER INFORMATION: Description of Unknown Organism: Illustrative
      toprim comparison peptide

<400> SEQUENCE: 38

Lys Val Leu Ile Ile Val Glu Gly Pro Ser Asp Ala Lys Ala Leu Ala
 1               5                  10                  15

Lys Ala Leu Gly Lys Pro Ser Lys Arg Lys Ile Val Tyr Glu Leu Pro
                 20                  25                  30

Gly Gly Lys Asp Gly Asn Val Val Ala Ser Leu Gly His Leu Val Asp
                 35                  40                  45

Leu Pro Thr Pro Glu Gly Tyr Asp Asp Lys Tyr Lys Trp Leu Trp Leu
 50                  55                  60

Pro Ile Val Asp Val Lys Lys Gly Phe Glu Pro Tyr Gln Ile Glu Phe
 65                  70                  75                  80

Asp Gln Leu Cys Lys Cys Ser Lys Lys Ile Asp Leu Lys Lys Glu Gln
                 85                  90                  95

Leu Lys Leu Leu Lys Lys Leu Ala Lys Lys Ala Asp Glu Val Ile Leu
                100                 105                 110

Ala Thr Asp Pro Asp Arg Glu Gly Glu Ala Ile Ala Trp Lys Leu Leu
            115                 120                 125

Glu Leu Leu Lys Pro Tyr Gly Pro Val Glu Leu Glu Asp Asp Lys Lys
        130                 135                 140

Val Arg Arg Ile Phe Leu Pro
145                 150

<210> SEQ ID NO 39
<211> LENGTH: 572
<212> TYPE: PRT
<213> ORGANISM: Staphylococcus aureus

<400> SEQUENCE: 39

Met Ile Gly Leu Cys Pro Phe His Asp Glu Lys Thr Pro Ser Phe Thr
 1               5                  10                  15

Val Ser Glu Asp Lys Gln Ile Cys His Cys Phe Gly Cys Lys Lys Gly
                 20                  25                  30

Gly Asn Val Phe Gln Phe Thr Gln Glu Ile Lys Asp Ile Ser Phe Val
                 35                  40                  45

Glu Ala Val Lys Glu Leu Gly Asp Arg Val Asn Val Ala Val Asp Ile
 50                  55                  60

Glu Ala Thr Gln Ser Asn Ser Asn Val Gln Ile Ala Ser Asp Asp Leu
 65                  70                  75                  80

Gln Met Ile Glu Met His Glu Leu Ile Gln Glu Phe Tyr Tyr Tyr Ala
                 85                  90                  95
```

```
Leu Thr Lys Thr Val Glu Gly Glu Gln Ala Leu Thr Tyr Leu Gln Glu
                100                 105                 110

Arg Gly Phe Thr Asp Ala Leu Ile Lys Glu Arg Gly Ile Gly Phe Ala
            115                 120                 125

Pro Asp Ser Ser His Phe Cys His Asp Phe Leu Gln Lys Lys Gly Tyr
        130                 135                 140

Asp Ile Glu Leu Ala Tyr Glu Ala Gly Leu Leu Ser Arg Asn Glu Glu
145                 150                 155                 160

Asn Phe Ser Tyr Tyr Asp Arg Phe Arg Asn Arg Ile Met Phe Pro Leu
                165                 170                 175

Lys Asn Ala Gln Gly Arg Ile Val Gly Tyr Ser Gly Arg Thr Tyr Thr
            180                 185                 190

Gly Gln Glu Pro Lys Tyr Leu Asn Ser Pro Glu Thr Pro Ile Phe Gln
        195                 200                 205

Lys Arg Lys Leu Leu Tyr Asn Leu Asp Lys Ala Arg Lys Ser Ile Arg
210                 215                 220

Lys Leu Asp Glu Ile Val Leu Leu Glu Gly Phe Met Asp Val Ile Lys
225                 230                 235                 240

Ser Asp Thr Ala Gly Leu Lys Asn Val Val Ala Thr Met Gly Thr Gln
                245                 250                 255

Leu Ser Asp Glu His Ile Thr Phe Ile Arg Lys Leu Thr Ser Asn Ile
            260                 265                 270

Thr Leu Met Phe Asp Gly Asp Phe Ala Gly Ser Glu Ala Thr Leu Lys
        275                 280                 285

Thr Gly Gln His Leu Leu Gln Gln Gly Leu Asn Val Phe Val Ile Gln
        290                 295                 300

Leu Pro Ser Gly Met Asp Pro Asp Glu Tyr Ile Gly Lys Tyr Gly Asn
305                 310                 315                 320

Asp Ala Phe Thr Thr Phe Val Lys Asn Asp Lys Lys Ser Phe Ala His
                325                 330                 335

Tyr Lys Val Ser Ile Leu Lys Asp Glu Ile Ala His Asn Asp Leu Ser
            340                 345                 350

Tyr Glu Arg Tyr Leu Lys Glu Leu Ser His Asp Ile Ser Leu Met Lys
        355                 360                 365

Ser Ser Ile Leu Gln Gln Lys Ala Ile Asn Asp Val Ala Pro Phe Phe
370                 375                 380

Asn Val Ser Pro Glu Gln Leu Ala Asn Glu Ile Gln Phe Asn Gln Ala
385                 390                 395                 400

Pro Ala Asn Tyr Tyr Pro Glu Asp Glu Tyr Gly Gly Tyr Asp Glu Tyr
                405                 410                 415

Gly Gly Tyr Ile Glu Pro Glu Pro Ile Gly Met Ala Gln Phe Asp Asn
            420                 425                 430

Leu Ser Arg Arg Glu Lys Ala Glu Arg Ala Phe Leu Lys His Leu Met
        435                 440                 445

Arg Asp Lys Asp Thr Phe Leu Asn Tyr Tyr Glu Ser Val Asp Lys Asp
450                 455                 460

Asn Phe Thr Asn Gln His Phe Lys Tyr Val Phe Glu Val Leu His Asp
465                 470                 475                 480

Phe Tyr Ala Glu Asn Asp Gln Tyr Asn Ile Ser Asp Ala Val Gln Tyr
                485                 490                 495

Val Asn Ser Asn Glu Leu Arg Glu Thr Leu Ile Ser Leu Glu Gln Tyr
            500                 505                 510
```

```
Asn Leu Asn Gly Glu Pro Tyr Glu Asn Glu Ile Asp Asp Tyr Val Asn
            515                 520                 525

Val Ile Asn Glu Lys Gly Gln Glu Thr Ile Glu Ser Leu Asn His Lys
        530                 535                 540

Leu Arg Glu Ala Thr Arg Ile Gly Asp Val Glu Leu Gln Lys Tyr Tyr
545                 550                 555                 560

Leu Gln Gln Ile Val Ala Lys Asn Lys Glu Arg Met
            565                 570

<210> SEQ ID NO 40
<211> LENGTH: 597
<212> TYPE: PRT
<213> ORGANISM: Geobacillus stearothermophilus

<400> SEQUENCE: 40

Met Gly His Arg Ile Pro Glu Thr Ile Glu Ala Ile Arg Arg Gly
1               5                   10                  15

Val Asp Ile Val Asp Val Ile Gly Glu Tyr Val Gln Leu Lys Arg Gln
            20                  25                  30

Gly Arg Asn Tyr Phe Gly Leu Cys Pro Phe His Gly Glu Lys Thr Pro
        35                  40                  45

Ser Phe Ser Val Ser Pro Glu Lys Gln Ile Phe His Cys Phe Gly Cys
    50                  55                  60

Gly Ala Gly Gly Asn Ala Phe Thr Phe Leu Met Asp Ile Glu Gly Ile
65                  70                  75                  80

Pro Phe Val Glu Ala Ala Lys Arg Leu Ala Ala Lys Ala Gly Val Asp
                85                  90                  95

Leu Ser Val Tyr Glu Leu Asp Val Arg Gly Arg Asp Asp Gly Gln Thr
            100                 105                 110

Asp Glu Ala Lys Ala Met Thr Glu Ala His Ala Leu Leu Lys Arg Phe
        115                 120                 125

Tyr His His Leu Leu Val His Thr Lys Glu Gly Gln Ala Ala Leu Asp
    130                 135                 140

Tyr Leu Gln Ala Arg Gly Trp Thr Lys Glu Thr Ile Asp Arg Phe Glu
145                 150                 155                 160

Ile Gly Tyr Ala Pro Asp Ala Pro Asp Ala Ala Lys Leu Leu Glu
                165                 170                 175

Ser His Ser Phe Ser Leu Pro Val Met Glu Lys Ala Gly Leu Leu Thr
            180                 185                 190

Lys Lys Glu Asp Gly Arg Tyr Val Gly Arg Phe Arg Asn Arg Ile Met
        195                 200                 205

Phe Pro Ile His Asp His Arg Gly Glu Thr Val Gly Phe Ser Gly Arg
    210                 215                 220

Leu Leu Gly Glu Gly His Pro Lys Tyr Val Asn Ser Pro Glu Thr Pro
225                 230                 235                 240

Val Phe Arg Lys Gly Ala Ile Leu Tyr His Phe His Ala Ala Arg Val
                245                 250                 255

Pro Ile Arg Lys Arg Gln Glu Ala Leu Leu Val Glu Gly Phe Ala Asp
            260                 265                 270

Val Ile Ser Ala Ala Gln Ala Gly Ile Asp Tyr Ala Ile Ala Thr Met
        275                 280                 285

Gly Thr Ser Leu Thr Glu Glu Gln Ala Arg Ile Leu Arg Pro Cys Asp
    290                 295                 300

Thr Ile Thr Ile Cys Tyr Asp Gly Asp Arg Ala Gly Ile Glu Ala Ala
305                 310                 315                 320
```

-continued

Trp Ala Ala Ala Glu Gln Leu Ser Ala Leu Gly Cys Arg Val Lys Val
                325                 330                 335

Ala Ser Leu Pro Asn Gly Leu Asp Pro Asp Glu Tyr Ile Arg Val Tyr
            340                 345                 350

Gly Gly Glu Arg Phe Ala Gly Glu Ala Gly Cys Arg Arg Pro Leu Val
        355                 360                 365

Ala Phe Lys Met Ala Tyr Leu Arg Arg Gly Lys Asn Leu Gln His Glu
    370                 375                 380

Gly Glu Arg Leu Arg Tyr Ile Asp Glu Ala Leu Arg Glu Ile Gly Lys
385                 390                 395                 400

Leu Ser Ser Pro Val Glu Gln Asp Tyr Tyr Leu Arg Gln Leu Ala Glu
                405                 410                 415

Glu Phe Ser Leu Ser Leu Ser Ala Leu His Glu Gln Leu Ser Arg Ser
            420                 425                 430

Gln Arg Glu Arg Thr Lys Pro Arg Glu Ala Pro Asp Gly Glu Thr Ala
        435                 440                 445

Arg Pro Met Leu Ala Lys Lys Leu Leu Pro Ala Phe Gln Asn Ala Glu
    450                 455                 460

Arg Leu Leu Leu Ala His Met Met Arg Ser Arg Asp Val Ala Leu Val
465                 470                 475                 480

Val Gln Glu Arg Ile Gly Gly Arg Phe Asn Ile Glu Glu His Arg Ala
                485                 490                 495

Leu Ala Ala Tyr Ile Tyr Ala Phe Tyr Glu Glu Gly His Glu Ala Asp
            500                 505                 510

Pro Gly Ala Leu Ile Ser Arg Ile Pro Gly Glu Leu Gln Pro Leu Ala
        515                 520                 525

Ser Asp Val Ser Leu Leu Ile Ala Asp Val Ser Glu Gln Glu
    530                 535                 540

Leu Glu Asp Tyr Ile Arg His Val Leu Asn Arg Pro Lys Trp Leu Met
545                 550                 555                 560

Leu Lys Val Lys Glu Gln Glu Lys Thr Glu Ala Glu Arg Arg Lys Asp
                565                 570                 575

Phe Leu Thr Ala Ala Arg Ile Ala Lys Glu Met Ile Glu Met Lys Lys
            580                 585                 590

Met Leu Ser Ser Ser
        595

<210> SEQ ID NO 41
<211> LENGTH: 603
<212> TYPE: PRT
<213> ORGANISM: Bacillus subtilis

<400> SEQUENCE: 41

Met Gly Asn Arg Ile Pro Asp Glu Ile Val Asp Gln Val Gln Lys Ser
1               5                   10                  15

Ala Asp Ile Val Glu Val Ile Gly Asp Tyr Val Gln Leu Lys Lys Gln
            20                  25                  30

Gly Arg Asn Tyr Phe Gly Leu Cys Pro Phe His Gly Glu Ser Thr Pro
        35                  40                  45

Ser Phe Ser Val Ser Pro Asp Lys Gln Ile Phe His Cys Phe Gly Cys
    50                  55                  60

Gly Ala Gly Gly Asn Val Phe Ser Phe Leu Arg Gln Met Glu Gly Tyr
65                  70                  75                  80

Ser Phe Ala Glu Ser Val Ser His Leu Ala Asp Lys Tyr Gln Ile Asp

```
                     85                  90                  95
Phe Pro Asp Asp Ile Thr Val His Ser Gly Ala Arg Pro Glu Ser Ser
                    100                 105                 110
Gly Glu Gln Lys Met Ala Glu Ala His Glu Leu Leu Lys Lys Phe Tyr
                115                 120                 125
His His Leu Leu Ile Asn Thr Lys Glu Gly Gln Glu Ala Leu Asp Tyr
            130                 135                 140
Leu Leu Ser Arg Gly Phe Thr Lys Glu Leu Ile Asn Glu Phe Gln Ile
145                 150                 155                 160
Gly Tyr Ala Leu Asp Ser Trp Asp Phe Ile Thr Lys Phe Leu Val Lys
                165                 170                 175
Arg Gly Phe Ser Glu Ala Gln Met Glu Lys Ala Gly Leu Leu Ile Arg
                180                 185                 190
Arg Glu Asp Gly Ser Gly Tyr Phe Asp Arg Phe Arg Asn Arg Val Met
                195                 200                 205
Phe Pro Ile His Asp His His Gly Ala Val Val Ala Phe Ser Gly Arg
            210                 215                 220
Ala Leu Gly Ser Gln Gln Pro Lys Tyr Met Asn Ser Pro Glu Thr Pro
225                 230                 235                 240
Leu Phe His Lys Ser Lys Leu Leu Tyr Asn Phe Tyr Lys Ala Arg Leu
                245                 250                 255
His Ile Arg Lys Gln Glu Arg Ala Val Leu Phe Glu Gly Phe Ala Asp
                260                 265                 270
Val Tyr Thr Ala Val Ser Ser Asp Val Lys Glu Ser Ile Ala Thr Met
                275                 280                 285
Gly Thr Ser Leu Thr Asp Asp His Val Lys Ile Leu Arg Arg Asn Val
            290                 295                 300
Glu Glu Ile Ile Leu Cys Tyr Asp Ser Asp Lys Ala Gly Tyr Glu Ala
305                 310                 315                 320
Thr Leu Lys Ala Ser Glu Leu Leu Gln Lys Lys Gly Cys Lys Val Arg
                325                 330                 335
Val Ala Met Ile Pro Asp Gly Leu Asp Pro Asp Asp Tyr Ile Lys Lys
                340                 345                 350
Phe Gly Gly Glu Lys Phe Lys Asn Asp Ile Ile Asp Ala Ser Val Thr
                355                 360                 365
Val Met Ala Phe Lys Met Gln Tyr Phe Arg Lys Gly Lys Asn Leu Ser
            370                 375                 380
Asp Glu Gly Asp Arg Leu Ala Tyr Ile Lys Asp Val Leu Lys Glu Ile
385                 390                 395                 400
Ser Thr Leu Ser Gly Ser Leu Glu Gln Glu Val Tyr Val Lys Gln Leu
                405                 410                 415
Ala Ser Glu Phe Ser Leu Ser Gln Glu Ser Leu Thr Glu Gln Leu Ser
                420                 425                 430
Val Phe Ser Lys Gln Asn Lys Pro Ala Asp Asn Ser Gly Glu Thr Lys
            435                 440                 445
Thr Arg Arg Ala His Leu Thr Thr Lys Ala Arg Gln Lys Arg Leu Arg
        450                 455                 460
Pro Ala Tyr Glu Asn Ala Glu Arg Leu Leu Ala His Met Leu Arg
465                 470                 475                 480
Asp Arg Ser Val Ile Lys Lys Val Ile Asp Arg Val Gly Phe Gln Phe
                485                 490                 495
Asn Ile Asp Glu His Arg Ala Leu Ala Ala Tyr Leu Tyr Ala Phe Tyr
            500                 505                 510
```

-continued

```
Glu Glu Gly Ala Glu Leu Thr Pro Gln His Leu Met Ala Arg Val Thr
        515                 520                 525

Asp Asp His Ile Ser Gln Leu Leu Ser Asp Ile Leu Met Leu Gln Val
    530                 535                 540

Asn Gln Glu Leu Ser Glu Ala Glu Leu Ser Asp Tyr Val Lys Lys Val
545                 550                 555                 560

Leu Asn Gln Arg Asn Trp Ser Met Ile Lys Glu Lys Glu Ala Glu Arg
                565                 570                 575

Ala Glu Ala Glu Arg Gln Lys Asp Phe Leu Arg Ala Ala Ser Leu Ala
            580                 585                 590

Gln Glu Ile Val Thr Leu Asn Arg Ser Leu Lys
        595                 600
```

FRAGMENTS AND VARIANTS OF *STAPHYLOCOCCUS AUREUS* DNAG PRIMASE, AND USES THEREOF

RELATED APPLICATION

This application claims the benefit of U.S. Provisional application 60/256,349, filed Dec. 19, 2000, which is incorporated herein by reference in its entirety, including drawings.

FIELD OF THE INVENTION

The invention relates to bacterial genes and proteins that are implicated in the process of DNA replication and also to bacteriophage genes and their protein products that interact with bacterial proteins involved in DNA replication. More particularly, the invention relates to compositions and methods involving an essential *Staphylococcus aureus* gene and its encoded protein STAAU_R9. In addition, the invention relates to screening assays to identify compounds which modulate the level and/or activity of STAAU_R9 and to such compounds.

BACKGROUND OF THE INVENTION

The Staphylococci make up a medically important genera of microbes known to cause several types of diseases in humans. *S. aureus* is a Gram positive organism which can be found on the skin of healthy human hosts and it is responsible for a large number of bacteremias.

*S. aureus* has been successfully treated with the penicillin derivative Methicillin in the past, but is now becoming increasingly resistant (MRSA—Methicillin Resistant *S. aureus*) to this antibiotic [Harbath et al., (1998) Arch. Intern. Med. 158:182-189]. For example, *S. aureus* endocarditis mortality can range from 26-45%, and combined β-lactam/aminoglycoside therapy is proving increasingly ineffective in disease eradication [Røder et al., (1999) Arch. Intern. Med. 159:462-469].

It is no longer uncommon to isolate *S. aureus* strains which are resistant to most of the standard antibiotics, and thus there is an unmet medical need and demand for new anti-microbial agents, vaccines, drug screening methods, and diagnostic tests for this organism. Antibiotics can be grouped into broad classes of activities against surprisingly few targets within the cell. Generally, the target molecule is a cellular protein that provides an essential function. The inhibition of activity of the essential protein leads either to death of the bacterial cell or to its inability to proliferate. Critical cellular functions against which antibiotics are currently in use include cell wall synthesis, folate and fatty acid metabolism, protein synthesis, and nucleic acid synthesis.

A proven approach in the discovery of a new drug, referred to as target-based drug discovery to distinguish it from cell-based drug discovery, is to obtain a target protein and to develop in vitro assays to interfere with the biological function of the protein. Nucleic acid metabolism is essential for all cells. The DNA synthesis machinery includes a number of proteins that act in concert to achieve rapid and highly processive replication of the chromosome in bacteria [reviewed in Kornberg, A., and Baker, T. A. 1992, DNA Replication, Second edition, New York: W.H. Freeman and Company, pp. 165-194; Benkovic, S. J. et al., 2001, Ann. Rev. Biochem. 70: 181-208]. As described below for DNA polymerase III, biological machines are often comprised of multiprotein complexes. Coordinated interactions among proteins of the bacterial primosome and replisome are essential to their efficiency. Thus, any members of essential multiprotein complexes are hypothetical targets for drug development. However, the fact that a protein can be associated with a certain biological function does not necessarily imply that it represents a suitable target for the development of new drugs [Drews J. 2000, Science 287:1960-1964]. For instance, although DNA replication is a well-known and essential process for bacterial growth, only a relatively small number of DNA replication proteins are targeted by currently-available antibiotics. Importantly, screening of compounds for those that inhibit the function of a target must be preferably rapid and selective.

There thus remains a need to identify new bacterial targets and new target domains, and more particularly *S. aureus* bacterial targets which could be used to screen for and identify antibacterial and more particularly anti-*S. aureus* agents. There also remains a need to identify new antimicrobial agents, vaccines, drug screening methods and diagnosis and therapeutic methods.

The present invention seeks to meet these and other needs.

The present description refers to a number of documents, the content of which is herein incorporated by reference in their entirety.

SUMMARY OF THE INVENTION

The present invention relates to new antimicrobial agents, vaccines, drug screening methods and diagnosis and therapeutic methods.

More particularly, the invention relates to proteins which interact with STAAU_R9 and in particular to bacterial growth-inhibitory (or inhibitor) bacteriophage gene products that interacts with the *S. aureus* STAAU_R9 polypeptide.

The invention also relates to a pair of interaction proteins and parts or fragments thereof. More specifically, the invention relates to the interacting domains of the *S. aureus* STAAU_R9 related protein and to proteins which interact with same and block or inhibit a STAAU_R9 biological activity. In a particular embodiment, the invention relates to a pair of interacting domains comprised of that of STAAU_R9 and a polypeptide encoded by a bacteriophage ORF which specifically interacts therewith, such as the *S. aureus* bacteriophage 96 ORF 78. In a particularly preferred embodiment of the present invention, the interaction of these domains and a modulation thereof forms the basis for screening assays to identify modulators of STAAU_R9 biological function and more particularly of antimicrobials.

The present invention also relates to polynucleotides and polypeptides of a multiprotein complex believed to be involved in DNA replication containing STAAU_R9 as a subunit, as well as variants and portions thereof.

In another aspect, the invention relates to methods for using such polypeptides and polynucleotides, including treatment and diagnosis of microbial diseases, amongst others.

In a further aspect, the invention relates to methods for identifying agonists and antagonists using the materials provided by the invention. In a related aspect, the invention relates to methods for treating microbial infections and conditions associated with such infections with the identified agonist or antagonist.

In a still further aspect, the invention relates to diagnostic assays for detecting diseases associated with microbial infections and conditions associated with such infections. In one embodiment, the diagnostic assay detects STAAU_R9 expression and/or activity.

In one particular embodiment of the invention, there is provided a method of identifying a compound that is active on a polypeptide comprising the amino acid sequence of SEQ ID NO: 2 or a biologically active fragment, or variant thereof, wherein SEQ ID NO:2 or a biologically active fragment or variant thereof is capable of binding specifically with a polypeptide comprising the sequence selected from SEQ ID NO: 4, a biologically active fragment thereof, and variant thereof, wherein the fragments or variants retain their capability of binding to SEQ ID NO:2, fragment (e.g. SEQ ID NO: 6), or variant thereof. In a preferred embodiment, the biologically active fragment or variant thereof of SEQ ID NO:2 is SEQ ID NO:6.

In one preferred embodiment of the invention, the identification of a compound active on a STAAU_R9 polypeptide is provided by a method comprising: contacting a first and a second polypeptide in the presence or absence of a candidate compound, wherein the first polypeptide comprises the amino acid sequence of SEQ ID NO: 2, a fragment or variant thereof which specifically bind to a second polypeptide derived from a bacteriophage ORF which is capable of binding specifically with one of SEQ ID NO: 2, a fragment, or variant thereof. In one particular embodiment, the second polypeptide is a phage ORF, a fragment thereof or variant thereof, wherein this second polypeptide maintains its biological activity; and detecting a biological activity of the first and/or second polypeptide, wherein a decrease in the biological activity in the presence thereof relative to the biological activity in the absence of the candidate compound identifies the candidate compound as a compound that is active on a polypeptide comprising the amino acid sequence of SEQ ID NO:2, fragment or variant thereof. In yet another particular embodiment of the present invention, the first polypeptide is SEQ ID NO:6 and the second polypeptide is SEQ ID NO:4.

In one particular embodiment, the biological activity is the binding of the first and second polypeptides to each other, the method comprising: contacting an assay mixture comprising a) a first polypeptide which comprises the amino acid sequence of SEQ ID NO:2 or a biologically active fragment, or variant thereof (e.g. SEQ ID NO: 6), and b) a second polypeptide selected from the group consisting of SEQ ID NO: 4, a fragment thereof, and a variant thereof; with a test compound; measuring the binding of the first and the second polypeptides in the presence of the candidate compound relative to the binding in the absence thereof and; determining the ability of the candidate compound to interact with a STAAU_R9 polypeptide, fragment or variant thereof (e.g. SEQ ID NO: 6), wherein a decrease in the binding of the first and the second polypeptides in the presence of the candidate compound that interacts with the first polypeptyde, relative to the binding in the absence of the candidate compound, identifies the candidate compound as a compound that is active on a STAAU_R9 polypeptide, fragment or variant thereof (e.g. SEQ ID NO: 6).

In one embodiment, the step of detecting comprises the step of measuring the binding of the first and second proteins, wherein the first or the second protein is directly or indirectly detectably labeled.

In different embodiments, the step of detecting comprises, but is no limited to, measurement by the method selected from the group consisting of time-resolved fluorescence resonance energy transfer, fluorescence polarization changes, measurement by surface plasmon resonance, a scintillation proximity assay, a biosensor assay, and phage display.

In one embodiment, a library of compounds is used. Non-limiting examples of candidate compounds include a small molecule, a peptidomimetic compound, a peptide, and a fragment or derivative of a bacteriophage inhibitor protein.

In one embodiment, the candidate compound is a peptide synthesized by expression systems and purified, or artificially synthesized.

The invention also encompasses a method of identifying an antimicrobial agent comprising determining whether a test compound is active on a S. aureus polypeptide, namely STAAU_R9 as set forth in SEQ ID NO: 2, or parts thereof.

In a further embodiment, identifying a compound active on a STAAU_R9 polypeptide is provided by a method which comprises: contacting a candidate compound with a polypeptide comprising the amino acid sequence of SEQ ID NO: 2; a fragment thereof, or a variant thereof (e.g. SEQ ID NO: 6), the fragment or variant retaining its biological activity (e.g. it specifically binds to SEQ ID NO: 4), and detecting binding of the candidate compound thereto, wherein detection of binding is indicative that the compound is active on the polypeptide.

In different embodiments, the step of detecting includes measuring the binding of a candidate compound to the polypeptide, wherein the compound is directly or indirectly detectably labeled, by a method comprising, but not limited to, time-resolved fluorescence resonance energy transfer, fluorescence polarization changes, measurement by surface plasmon resonance, scintillation proximity assay, biosensor assay, and phage display.

In one embodiment, a library of compounds is used. Non-limiting examples of candidate compound include a small molecule, a peptidomimetic compound, a peptide, and a fragment or derivative of a bacteriophage inhibitor protein.

In one embodiment, the candidate compound is a peptide synthesized by expression systems and purified, or artificially synthesized.

The invention further encompasses a method of identifying a compound that is active on a STAAU_R9 polypeptide, a fragment or a variant thereof (e.g. SEQ ID NO: 6), comprising the steps of contacting a candidate compound (or library thereof) with cells expressing a polypeptide comprising SEQ ID NO: 2; and detecting STAAU_R9 activity in the cells, wherein a decrease in activity relative to STAAU_R9 activity in cells not contacted with a candidate compound is indicative of inhibition of STAAU_R9 activity. The invention also encompasses such a method but using a fragment or variant of SEQ ID NO:2.

Of course, the invention further encompasses methods of identifying a compound that modulates the activity of a STAAU_R9 polypeptide, wherein a compound increasing the activity relative to STAAU_R9 activity in cells not contacted with the candidate compound, is selected as a compound which is a stimulator of STAAU_R9 activity.

In a preferred embodiment, the step of detecting comprises a method of measuring the ability of a candidate, test compounds, or agents to stimulate or preferably to inhibit a STAAU_R9 molecule's ability to modulate DNA synthesis (such assays are described in more detail hereinbelow).

The invention further encompasses a method of identifying a compound that is active on a STAAU_R9 polypeptide, a fragment or a variant thereof, comprising the steps of contacting a candidate compound (or library thereof) in a cell-free assay, with a STAAU_R9 protein or biologically active portion thereof, either naturally occurring or recombinant in origin; and detecting STAAU_R9 activity, wherein a decrease in activity relative to STAAU_R9 activity in cell-free assay not contacted with a candidate compound is indicative of inhibition of STAAU_R9 activity. In one particular embodiment of this aspect of the present invention, the fragment or the variant thereof is SEQ ID NO:6.

In one preferred embodiment, the step of detecting comprises a method of measuring the ability of a candidate compound, test compounds, or agent to stimulate, or preferably to inhibit a STAAU_R9 molecule's ability to modulate DNA synthesis (such assays are described in more detail hereinbelow).

The invention further encompasses an agonist or an antagonist of the activity of a STAAU_R9 polypeptide or a nucleic acid or gene encoding the polypeptide.

The assays described herein may be used as initial or primary screens to detect promising lead compounds for further development. The same assays may also be used in a secondary screening assay to measure the activity of candidate compounds on a STAAU_R9 polypeptide. Often, lead compounds will be further assessed in additional, different screens. This invention also includes secondary STAAU_R9 screens which may involve biological assays utilizing S. aureus strains or other suitable bacteria.

Tertiary screens may involve the study of the effect of the agent in an animal. Accordingly, it is within the scope of this invention to further use an agent identified as described herein in an appropriate animal model. For example, a test compound identified as described herein (e.g., a STAAU_R9 inhibiting agent, an antisense STAAU_R9 nucleic acid molecule, a STAAU_R9-specific antibody, or a STAAU_R9-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatment (e.g. bacterial infections), as described herein.

The invention further encompasses a method of making an antibacterial compound, comprising the steps of: a) determining whether a candidate compound is active on a polypeptide comprising the amino acid sequence of SEQ ID NO: 2, fragment or variant thereof (e.g. SEQ ID NO: 6), or a gene encoding the polypeptide; and b) synthesizing or purifying the candidate compound in an amount sufficient to provide a therapeutic effect when administered to an organism infected by a bacterium naturally producing a polypeptide comprising the amino acid sequence of SEQ ID NO: 2, fragment or variant thereof (e.g. SEQ ID NO: 6).

The invention further encompasses a method for inhibiting a bacterium, comprising contacting the bacterium with a compound active on a polypeptide comprising the amino acid sequence of SEQ ID NO: 2, fragment or variant thereof, or a nucleic acid encoding the polypeptide.

In one embodiment, the step of contacting is performed in vitro.

In another embodiment, the step of contacting is performed in vivo in an animal.

In another embodiment, bacterium is contacted with the active compound in combination with existing antimicrobial agents. Thus, the invention also relates to antimicrobial compositions comprising a compound of the present invention in combination with an existing antimicrobial agent. Of course, more than one active compound of the present invention could be combined with or without existing antimicrobial agent(s).

The invention further encompasses a method for treating or preventing a bacterial infection in an animal suffering from an infection or susceptible of suffering from same, comprising administering thereto a therapeutically effective amount of a compound active on a polypeptide comprising the amino acid sequence of SEQ ID NO: 2, variant or fragment thereof (e.g. SEQ ID NO: 6), or nucleic acid sequence encoding same. The animal is preferably, but not necessarily a mammal, and more preferably a human. In one embodiment, the active compound is administred to the animal in combination with existing antimicrobial agents. Thus, the invention also relates to antimicrobial compositions comprising a compound of the present invention in combination with an existing antimicrobial agent.

The invention further encompasses a method of prophylactic treatment to prevent bacterial infection comprising contacting an indwelling device with a compound active on a polypeptide comprising the amino acid sequence of SEQ ID NO: 2, variant or fragment thereof (e.g. SEQ ID NO: 6) before its implantation into a mammal, such contacting being sufficient to prevent S. aureus infection at the site of implantation.

The invention further encompasses a method of prophylactic treatment to prevent infection of an animal by a bacterium comprising administering to the animal a prophylactically effective amount of a compound that is active on a polypeptide comprising the amino acid sequence of SEQ ID NO: 2, variant or fragment thereof (e.g. SEQ ID NO: 6) or a gene encoding the polypeptide in an amount sufficient to prevent infection of the animal. In a particular embodiment, the prophylactically effective amount reduces adhesion of the bacterium to a tissue surface of the mammal.

The invention further encompasses a method of diagnosing in an animal an infection with S. aureus, comprising: determining the presence in the animal of a polypeptide comprising the amino acid sequence of SEQ ID NO: 2, part thereof, variant thereof, fragment thereof (e.g. SEQ ID NO: 6), epitope thereof or nucleic acid encoding same. Preferably the polypeptide is capable of specifically interacting with 96 ORF 78. Preferably, the animal is a human.

In one embodiment, the determining step comprises contacting a biological sample of the animal or individual with an antibody specific for an epitope present on a polypeptide comprising the amino acid sequence of SEQ ID NO: 2, variant or fragment thereof (e.g. SEQ ID NO: 6).

The invention further encompasses a method of diagnosing in an animal or individual an infection with S. aureus, comprising determining the presence in the animal or individual of a nucleic acid sequence encoding a polypeptide comprising the amino acid sequence of SEQ ID NO: 2, variant or fragment thereof (e.g. SEQ ID NO: 6), wherein the polypeptide is capable of specifically interaction with 96 ORF 78.

In one embodiment, the determining step comprises contacting a nucleic acid sample of the animal or individual with an isolated, purified or enriched nucleic acid probe of at least 15 nucleotides in length that hybridizes under stringent hybridization conditions with the sequence of SEQ ID NO: 1, or the complement thereof.

The invention further encompasses an isolated, purified or enriched polynucleotide comprising a nucleotide sequence encoding a polypeptide, which can interact with a bacterial growth-inhibitory (or inhibitor) bacteriophage 96 ORF 78 gene product or part thereof.

In one particular embodiment, the isolated, purified or enriched polynucleotide comprises a nucleotide sequence encoding a polypeptide corresponding to SEQ ID NO: 2, a complement thereof, a fragment, or a variant thereof wherein the encoded polypeptide is capable of binding specifically with the 96 ORF 78 polypeptide.

In one preferred embodiment, the isolated, purified or enriched polynucleotide fragment comprises nucleotides 1683-1800 of SEQ ID NO:1, herein referred to as SEQ ID NO: 5 comprising a nucleotide sequence encoding the polypeptide of SEQ ID NO: 6 or the complement of such nucleotide sequence. In another preferred embodiment, the isolated, purified or enriched polynucleotide fragment consists in SEQ ID NO:5.

In another particular embodiment of the present invention, the isolated, purified or enriched polynucleotide comprises a nucleotide sequence having at least 60%, at least 70%, at least 80%, and more preferably at least 90% identity to the sequence of SEQ ID NO: 5, or to the complement thereof.

The invention further encompasses an isolated, purified or enriched polypeptide comprising the amino acid sequence of SEQ ID NO: 2, a variant or fragment thereof capable of binding specifically with a polypeptide comprising the bacteriophage 96 ORF 78 gene product, or part thereof.

The invention further encompasses an isolated, purified or enriched polypeptide comprising the amino acid sequence of SEQ ID NO: 6, or variant thereof, wherein SEQ ID NO:6 or variant thereof retains its biological activity in binding to the bacteriophage 96 ORF 78 gene product. In a particular embodiment, the amino acid sequence enabling the binding of the polypeptide to the bacteriophage polypeptide consists in the amino acid sequence of SEQ ID NO:6. In another embodiment, the sequence of SEQ ID NO:6 is part of a chimeric protein.

In one particular embodiment, the isolated, purified or enriched polypeptide comprises or consists of an amino acid sequence having at least 35%, at least 40%, at least 50%, at least 60%, at least 70%, and more preferably at least 80%, at least 90%, at least 95% or at least 99% identity to the amino acid sequence of SEQ ID NO: 6, wherein the polypeptide directly interacts with the bacteriophage 96 ORF 78 polypeptide.

In one particular embodiment, the isolated, purified or enriched polypeptide of the present invention comprises or consists of an amino acid sequence having at least 60%, at least 70%, at least 80%, more preferably at least 90%, and more preferably at least 95% or at least 99% similarity to the amino acid sequence of SEQ ID NO: 6, wherein the polypeptide directly interacts with the bacteriophage 96 ORF 78 polypeptide.

In one particular embodiment, the isolated, purified or enriched polypeptide comprises the amino acid sequence of SEQ ID NO:6. In another embodiment, the sequence of SEQ ID NO:6 is part of a chimeric protein.

The invention further encompasses an isolated, purified or enriched antibody specific for an epitope encoded by the amino acid sequence set forth in SEQ ID NO: 6.

The invention further encompasses a composition comprising two polypeptides, a bacteriophage-encoded polypeptide and a *S. aureus* STAAU_R9 polypeptide corresponding to SEQ ID NO: 2 or a fragment thereof (e.g. SEQ ID NO: 6). In another embodiment, the invention encompasses a composition comprising two interacting polypeptides derived from a bacteriophage encoded polypeptide and a *S. aureus* STAAU_R9 polypeptide. As such, the invention encompasses a composition comprising two nucleic acid sequences encoding these directly interacting polypeptides.

The invention in addition encompasses a composition comprising two interacting polypeptides, a bacteriophage 96 ORF 78-encoded polypeptide, fragment or variant thereof, and a *S. aureus* STAAU_R9 polypeptide comprising the sequence as set forth in SEQ ID NO:2, fragment, or variant thereof (e.g. SEQ ID NO:6) In another embodiment, the invention encompasses a composition comprising a pair of specifically interacting domains, the pair comprising: a STAAU_R9 polypeptide and a polypeptide encoded by a bacteriophage ORF which specifically interacts with the STAAU_R9 polypeptide.

Further, the invention encompasses a process for producing a pharmaceutical composition comprising: a) carrying out a screening assay of the present invention aimed at identifying a compound that is active on a STAAU_R9 polypeptide or biologically active fragment or variant thereof, wherein the STAAU_R9 polypeptide is capable of binding specifically with a second polypeptide derived from a bacteriophage ORF, and wherein the screening assay enables the identification of a candidate compound as a compound that is active on a STAAU_R9 polypeptide; and b) mixing the compound identified in a) with a suitable pharmaceutical carrier. In one embodiment, the STAAU_R9 polypeptide comprises the amino acid sequence as set forth in SEQ ID NO:6 or biologically active fragment or variant thereof.

In a further embodiment of this process of producing a pharmaceutical composition, the process further includes a scaling-up of the preparation for isolating of the identified compound active on the STAAU_R9 polypeptide. In yet another embodiment of this process of producing a pharmaceutical composition, the pharmaceutical composition prepared comprises a derivative or homolog of the compound identified in a).

Also, the invention encompasses the use of one of: a) a STAAU_R9 polypeptide comprising the amino acid sequence of SEQ ID NO:2, a biologically active fragment thereof or variant thereof (e.g. SEQ ID NO: 6), wherein the STAAU_R9 polypeptide is capable of binding specifically to a polypeptide derived from a bacteriophage ORF, b) a composition comprising a pair of specifically interacting domains comprised of a polypeptide of STAAU_R9, biologically active fragment thereof or variant thereof (e.g. SEQ ID NO: 6) and a polypeptide encoded by a bacteriophage ORF which specifically interacts with STAAU_R9; or c) an assay mixture comprising a first polypeptide which comprises the amino acid sequence of SEQ ID NO:2, biologically active fragment thereof or variant thereof (e.g. SEQ ID NO: 6) and a second polypeptide encoded by a bacteriophage ORF which specifically interact with each other; for the identification of a compound that is active on a polypeptide comprising the amino acid sequence of SEQ ID NO:2, biologically active fragment thereof or variant thereof (e.g. SEQ ID NO: 6).

Further features and advantages of the invention will become more fully apparent in the following description of the embodiments and drawings thereof, and from the claims.

BRIEF DESCRIPTION OF THE DRAWINGS

Having thus generally described the invention, reference will now be made to the accompanying drawings, showing by way of illustration a preferred embodiment thereof, and in which:

FIG. 1 shows the nucleotide (SEQ ID NO: 1) and amino acid (SEQ ID NO: 2) sequences of *S. aureus* STAAU_R9.

FIG. 2 shows the nucleotide (SEQ ID NO: 3) and the amino acid (SEQ ID NO: 4) sequences of *S. aureus* bacteriophage 96 ORF 78.

FIG. 7 shows the results of amino acid sequence analysis of STAAU_R9. A) Results of the STAAU_R9 Hidden Markov Model (HMM) searching analysis of the publically available Pfam database identifying two conserved Pfam motifs: Zf-CHC2 (SEQ ID NO: 37) compared with STAAU_R9 (residues 3-100 of SEQ ID NO: 2) and Toprim (SEQ ID NO: 38) compared with STAAU_R9 (residues 260-339 of SEQ ID NO: 2). B) Results of the global optimal alignment of the amino acid sequences of different STAAU_R9-related sequences. STAAU_R9 (SEQ ID NO: 2) is highly similar to *S. aureus* DNA primase (SEQ ID NO: 39) (92% identity to gi|2494147|sp|O05338|PRIM_STAAU DNA PRIMASE, DnaG). Note the discrepancies between the sequences of DNA primase from *S. aureus* as reported in Swissprot and as predicted from the University of Oklahoma *S. aureus* genome sequencing project database. STAAU_R9 (SEQ ID NO: 2) is also moderately similar to a variety of bacterial DNA primase proteins including *B. stearothermophilus* DnaG (SEQ ID NO: 40) (34% identity to gi|9910841|sp|Q9X4D0|PRIM_BACST DNA PRIMASE) *B. subtilis* DnaG (SEQ ID NO: 41) (36% identity to gi|130904|sp|PO5096|PRIM_BACSU DNA PRIMASE) and *E. coli* DnaG (SEQ ID NO: 22) (27% identity to gi|1309081|sp|P02923|PRIM_ECOLI DNA PRIMASE).

FIG. 9 shows the results of yeast two hybrid analyses designed to test the interaction of *S. aureus* STAAU_R9_35 comprising the amino acid 35 to 599 of SEQ ID NO: 2 and 96 ORF 78. A) Yeasts were co-transformed with pairs of vectors as indicated above each pair of photographs of Petri plates. Co-transformants were plated in parallel on yeast synthetic medium (SD) supplemented with amino acid drop-out lacking tryptophan and leucine (TL minus) and on SD supplemented with amino acid drop-out lacking tryptophan, histidine, adenine and leucine (THAL minus). Co-transformants harboring the 96 ORF 78 polypeptide only grew on selective THAL minus media in the presence of STAAU_R9_35 (top pairs of petri plates). Co-transformation of these polypeptides with control vectors harboring non-interacting proteins (pGBKLaminC or pGADT7T) does not result in growth on THAL minus medium. The cloning of STAAU_R9 in the pGBK vector results in growth on THAL minus medium in the presence of the negative control. B) Results of the luminescent β-galactosidase enzymatic assays with protein extracts from the same co-transformants. The presence of STAAU_R9_35 and 96 ORF 78 in the same cell results in at least a 10-fold induction of the β-galactosidase activity compared to controls with non-interacting proteins.

FIG. 11 shows the list of the oligonucleotide primers (SEQ ID NOS 8-21 and 7, respectively in order of appearance) used for amplification by PCR and cloning of the *S. aureus* STAAU_R9-related sequences in vectors for the yeast two-hybrid analysis. A) Sequence of each primer with the restriction site used for cloning identified; B) pairs of primers used to clone the full-length STAAU_R9 and the thirteen STAAU_R9-related fragments.

Figure 3:
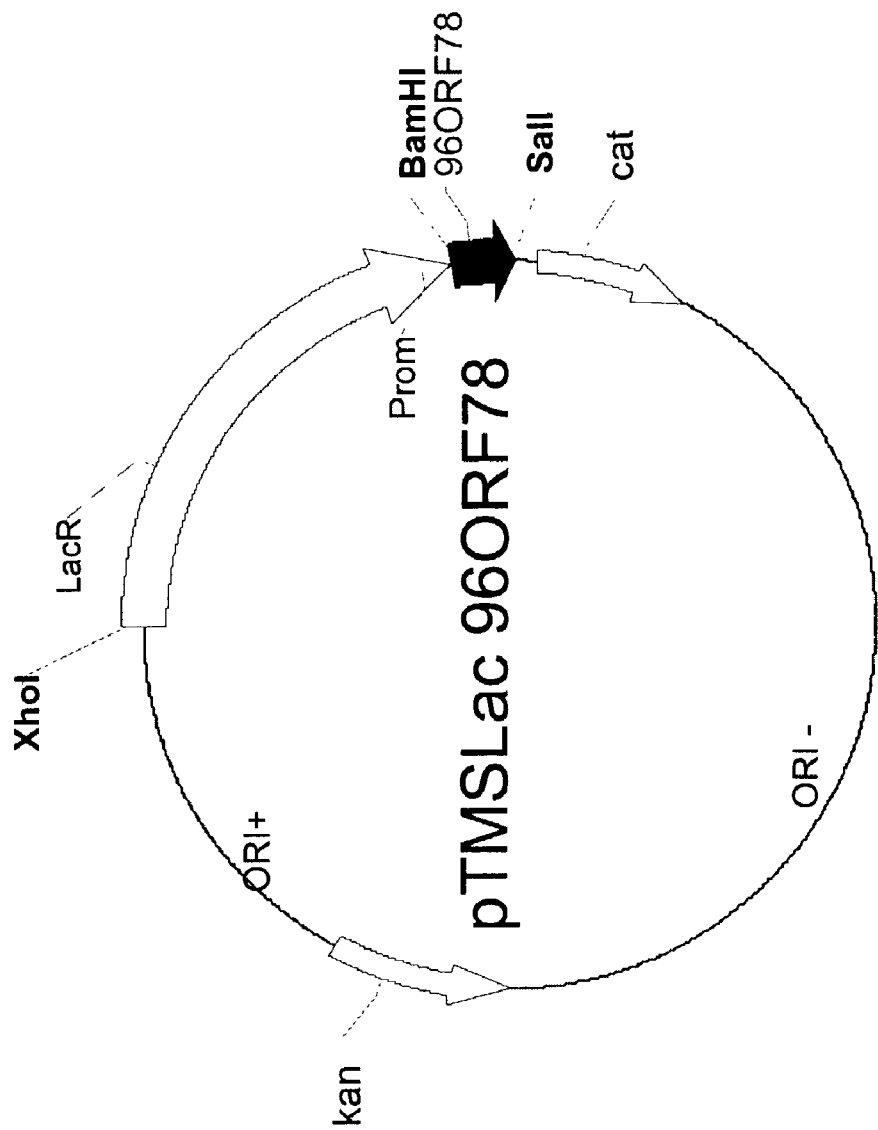
FIG. 3 shows the bacterial inhibitory potential of bacteriophage 96 ORF 78 and the expression vector used to induce its expression in *S. aureus*. A) Schematic diagram of expression vector pTMSMLac/ORF used to induce expression of 96 ORF 78 in *S. aureus* cells; B) and D) results of a colony forming unit (CFU) assay for inhibitory potential of 96 ORF 78 when expressed in *S. aureus* grown in liquid medum followed by plating on semi-solid medium either containing (B) or not containing (D) the antibiotic necessary to maintain the selective pressure for the plasmid; C) growth of *S. aureus* cells in liquid medium in the presence and absence of inducer for the expression of 96 ORF 78.
Figure 3:
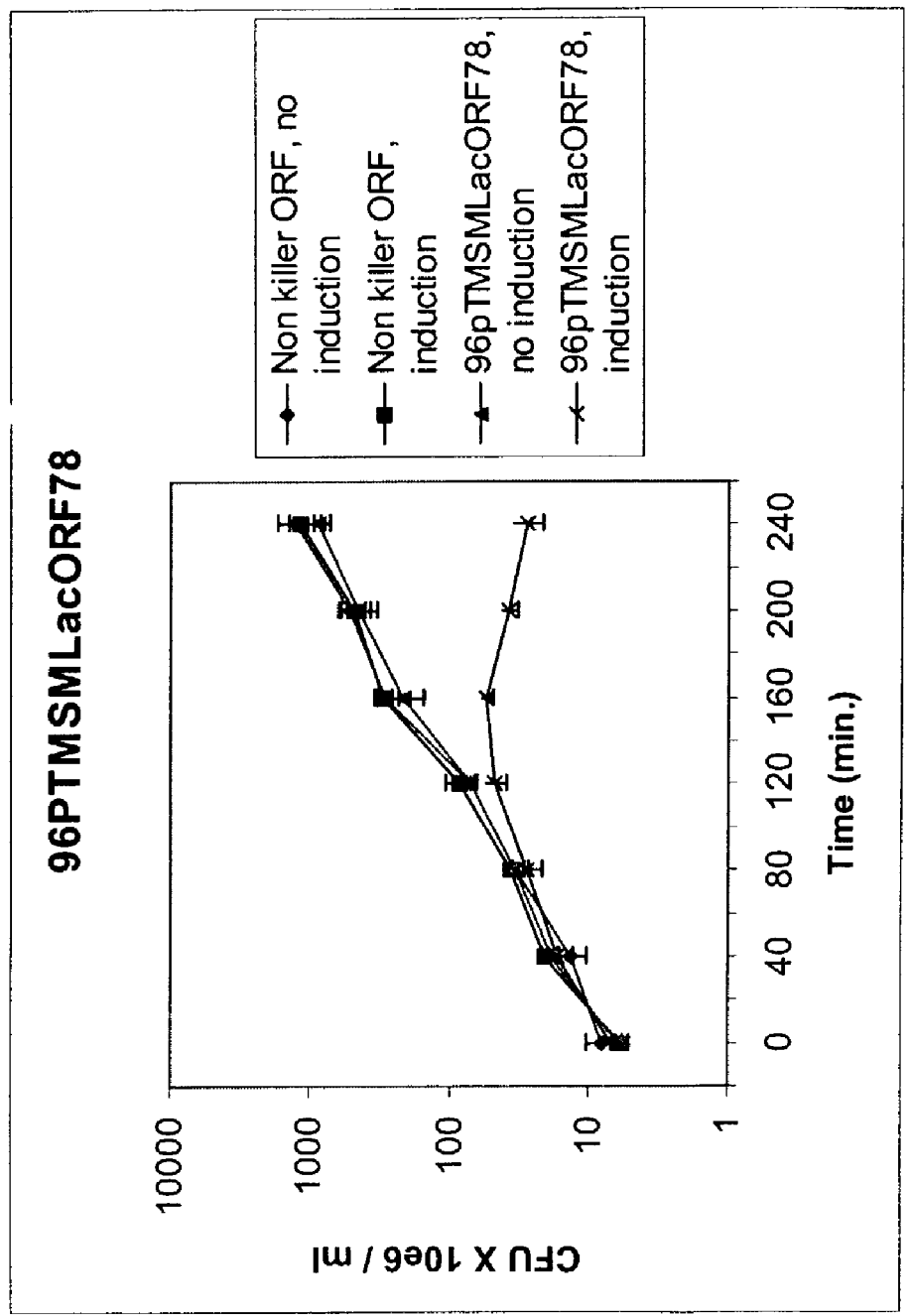

Other objects, advantages and features of the present invention will become more apparent upon reading of the following non-restrictive description of preferred embodiments with reference to the accompanying drawing which is exemplary and should not be interpreted as limiting the scope of the present invention.

DESCRIPTION OF THE PREFERRED EMBODIMENT

The invention relates to the discovery of an essential gene and its encoded polypeptide in *S. aureus* and portions thereof useful for example in screening, diagnostics, and therapeutics. More specifically, the invention also relates to *S. aureus* STAAU_R9 polypeptides and polynucleotides as described in greater detail below, and to a pair of polynucleotides encoding a pair of interacting polypeptides, to the pair of polypeptides themselves, or interacting domains thereof. In a particular embodiment, the pair includes a *S. aureus* STAAU_R9 polypeptide or interacting domain thereof (e.g. SEQ ID NO: 6) and a 96 ORF 78 or interacting domain thereof. In one embodiment, the invention relates to STAAU_R9 having the nucleotide or amino acid sequence disclosed as SEQ ID NO: 1 or SEQ ID NO: 2, respectively. The sequences presented as SEQ ID NOs: 1 and 2 represent an exemplification of the invention, since those of ordinary skill will recognize that such sequences can be usefully employed in polynucleotides in general, including ribopolynucleotides. 96 ORF 78 was described in U.S. patent application Ser. No. 09/676,519.

The methodology of two previous inventions (U.S. Provisional Patent Application 60/110,992, filed Dec. 3, 1998, and PCT International Application WO1999/IB99/02040, filed Dec. 3, 1999) has been used to identify and characterize essential polynucleotide and polypeptide sequences from *S. aureus*.

Thus, in a particular embodiment of the present invention, there is provided polynucleotide and polypeptide sequences isolated from *S. aureus* that can be used in a drug screening assay to identify compounds with anti-microbial activity. The polynucleotide and polypeptide sequences can be isolated using a method similar to those described herein, or using another method. In addition, such polynucleotide and polypeptide sequences can be chemically synthesized. The identification of the *S. aureus* STAAU_R9 sequence as a target for a bacteriophage validates the approach of the present invention to identify bacterial targets and also validates STAAU_R9 as a key target for antibacterial drug development as well as diagnosis and treatment methods based thereon.

DEFINITIONS

In order to provide a clear and consistent understanding of terms used in the present description, a number of definitions are provided hereinbelow.

The terminology "active on", with reference to a particular cellular target, such as the product of a particular gene, means that the target is an important part of a cellular pathway which includes that target and that an agent or compound acts on that pathway. Thus, in some cases the agent or compound may act on a component upstream or downstream of the stated target (i.e. indirectly on the target), including a regulator of that pathway or a component of that pathway. In general, an antibacterial agent is active on an essential cellular function, often on a product of an essential gene (i.e. directly on the target).

The terminology "active on" also refers to a measurable effect of the compound on the target it is active on (as compared to the activity of the target in the absence of the compound). The activity referred thereto is any one of a biological activity of one of the polypeptides of the present invention.

As used herein, the terms "inhibit", "inhibition", "inhibitor", and "inhibitor" all refer to a function of reducing a biological activity or function. Such reduction in activity or function can, for example, be in connection with a cellular component (e.g., an enzyme), or in connection with a cellular process (e.g., synthesis of a particular protein), or in connection with an overall process of a cell (e.g., cell growth). In reference to cell growth, the inhibitory effects may be bacteriocidal (killing of bacterial cells) or bacteriostatic (i.e.—stopping or at least slowing bacterial cell growth). The latter slows or prevents cell growth such that fewer cells of the strain are produced relative to uninhibited cells over a given time period. From a molecular standpoint, such inhibition may equate with a reduction in the level of, or elimination of, the transcription and/or translation and/or stability of a specific bacterial target(s), and/or reduction or elimination of activity of a particular target biomolecule.

As used herein, the terminology "STAAU_R9 polypeptide" or "dnaG polypeptide" refers to a polypeptide encompassing *S. aureus* STMU_R9-derived polypeptides, variant thereof or an active domain of *S. aureus* STAAU_R9. Non-limiting examples of STAAU_R9 polypeptides include polypeptides comprising the amino acid sequence as set forth in SEQ ID NO: 6, SEQ ID NO: 2, variants or fragments thereof. As used herein, the term "active domain of *S. aureus* STAAU_R9", "biologically active polypeptide of STAAU_R9" or the like refers to a polypeptide fragment or portion of *S. aureus* STAAU_R9 that retains an activity of *S. aureus* STAAU_R9. The term "STAAU_R9 polypeptide" is also meant to encompass *S. aureus* STAAU_R9 or an active domain of *S. aureus* STAAU_R9 that is fused to another polypetide, such as a non-STAAU_R9 polypeptide sequence.

These include, but are not limited to, nucleotide sequences comprising all or portions of the STAAU_R9 nucleic acid depicted in SEQ ID NO:1 which are altered by the substitution, deletion or mutation of different codons that encode a functionally equivalent amino acid residue within the sequence.

In a particular embodiment of the present invention, and as shown in Example 3, the nucleic acid sequence can comprise a nucleotide sequence which results from deletion of at least one nucleotide at the 3' end and/or at the 5' end, and preferably at the 5' end of the nucleic acid sequence in SEQ ID NO:1 or a derivative thereof. Thus, as well-known in the art, SEQ ID NO:1 (and its encoded polypeptide [SEQ ID NO:2]) can be used to generate deletion mutants. Thus, for example, the present invention provides deletion mutants of SEQ ID NO:2 (amino acids 1-599), spanning amino acids 35-599, 229-599, 380-599, 449-599, 490-599 and 561-599 (SEQ ID NO:6) of SEQ ID NO:2 which retain at least one of their biological activities. It should be understood that the deletions of a few amino acids of SEQ ID NO:6, which do not affect the biological activity of SEQ ID NO:6, are also covered by the present invention. It should be understood that the nucleic acid sequences encoding such deletion mutants are also within the scope of the present invention.

"STAAU_R9 activity" "polypeptide comprising the amino acid sequence SEQ ID NO: 2 activity" "polypeptide comprising the amino acid sequence SEQ ID NO: 6 activity" "dnaG polypeptide activity" or "biological activity" of STAAU_R9 or other polypeptides of the present invention is defined as a detectable biological activity of a gene, nucleic acid sequence, protein or polypeptide of the present invention. This includes any physiological function attributable to the specific biological activity of STAAU_R9, or phage ORF of the present invention. This includes measurement of the DNA synthesis activities of STAAU_R9 in cells or in vitro. Non-limiting examples of the biological activities may be made directly or indirectly. STAAU_R9 biological activity, for example, is not limited, however, to its function in DNA synthesis. Biological activities may also include simple binding to other factors (polypeptides or otherwise), including compounds, substrates, and of course interacting proteins. Thus, for STAAU_R9, biological activity includes any standard biochemical measurement of STMU_R9 such as conformational changes, phosphorylation status or any other feature of the protein that can be measured with techniques known in the art. STAAU_R9 biological activity also includes activities related to STAAU_R9 gene transcription or translation, or any biological activities of such transcripts or translation products. The instant invention is also concerned with STAAU_R9 interaction with an inhibitory polypeptide of the present invention, biological activity of STAAU_R9 and fragment thereof also includes assays which monitor binding and other biochemical measurements of these polypeptides. Furthermore, for certainty, the terminology "biological activity" also includes measurements based on the interaction of domains of interacting proteins of the present invention (i.e. the phage ORFs or domains thereof). Non-limiting examples of "biological activity" include one or more of the following:

i) Binding to a Bacterial Growth Inhibitory ORF Derived from a Bacteriophage Including a 96 ORF 78 Polypeptide or Part Thereof.

Determining the binding between polypeptides of the present invention can be accomplished by one of the methods described below or known in the art for determining direct binding. While it might be advantageous in certain embodiments of the present invention to provide a binding assay which is amenable to automation and more particularly to high-throughput, the present invention is not so limited. The binding or physical interaction between a polypeptide comprising the amino acid sequence of SEQ ID NO: 2, provided herein, or fragment thereof (e.g. SEQ ID NO: 6) and a bacteriophage protein 96 ORF 78 or portion thereof may be between isolated polypeptides consisting essentially of the sequence necessary for binding, or, alternatively, the respective polypeptide sequence may be comprised within a larger polypeptide.

A number of non-limiting methods, useful in the invention, to measure the binding of bacteriophage 96 ORF 78 to a polypeptide comprising the amino acid sequence of SEQ ID NO: 2, or fragment thereof (e.g. SEQ ID NO: 6) are described below. Binding can be measured by coupling one molecule to a surface or support such as a membrane, a microtiter plate well, or a microarray chip, and monitoring binding of a second molecule by any number of means including but not limited to optical spectroscopy, fluorometry, and radioactive label detection.

For example, Time-Resolved Fluorescence Resonance Energy Transfer (TR-FRET), in which the close proximity of two fluorophores, whether intrinsic to, as in the case of a naturally-fluorescent amino acid residue such as tryptophan, or either covalently or non-covalently bound to a separate molecule, causes the emission spectrum of one fluorophore to overlap with the excitation spectrum of the second, and thus dual fluorescence following excitation of only one fluorophore is indicative of binding. An additional assay useful in the present invention is fluorescence polarization, in which the quantifiable polarization value for a given fluorescently-tagged molecule is altered upon binding to a second molecule. Surface plasmon resonance assays can be used as a quantitative method to measure binding between two molecules by the change in mass near an immobilized sensor caused by the binding of one protein from the aqueous phase to a second immobilized on the sensor. A scintillation proximity assay can also be used to measure binding of a polypeptide comprising the amino acid sequence of SEQ ID NO: 2, and fragment thereof and a bacteriophage ORF or fragment thereof in which binding in the proximity to a scintillant converts radioactive particles into a photon signal that is detected by a scintillation counter or other detector. Additionally, binding can be evaluated by a Bio Sensor assay, which is based on the ability of the sensor to register changes in admittance induced by ion-channel modulation following binding. Phage display is also a powerful quantitative assay to measure protein:protein interaction using colourimetric ELISA (enzyme-linked immunosorbent assay).

ii) The Stimulation of the DNA Synthesis

The terminology "biological activity" also relates to DNA synthesis stimulation by a polypeptide having the S. aureus STAAU_R9 sequence provided herein, a fragment or variant thereof, or a protein comprising a S. aureus STAAU_R9 polypeptide fragment or variant thereof, that directly interacts with bacteriophage protein 96 ORF 78, or a STAAU_R9-binding fragment of the 96 ORF 78 proteins or variant thereof.

A number of methods, useful in the invention, to measure the stimulation of DNA synthesis by a polypeptide comprising the amino acid sequence of STAAU_R9 are described below. The level of DNA synthesis can be evaluated by, for example, the measurement of incorporation of radioactively- or fluorescently-labeled nucleotides into DNA of S. aureus cells in an in vivo bacterial DNA replication assay, or by measuring the ratio of single-stranded (ss) to double-stranded (ds) plasmid DNA in a plasmid DNA replication assay.

Alternatively, the DNA synthesis could be measured by using soluble in vitro systems based on the use of a variety of different DNA substrates including ss DNA, either linear or circular. In one embodiment, the replication assay involves crude, enriched, or partially purified cellular protein extracts or recombinantly produced proteins. In another embodiment, the reconstituted protein assay involves partially purified or pure forms of native proteins or fusion proteins or fragments thereof.

In one cell-free in vitro assay, an extract prepared from S. aureus is supplied to a plasmid substrate, for example a circular M13 ssDNA substrate, in a reaction including exogenous radiolabeled deoxynucleotide triphosphates (dATP, dTTP, dGTP and dCTP), $MgCl_2$ and ATP. Another means to assay for STAAU_R9 activity is to measure the level of radiolabeled nucleotide incorporated into DNA in a reconstituted in vitro assay using ssDNA substrate and S. aureus purified proteins [Yuhakov et al. 1999, Cell 96: 153-163].

iii) The Activity of DNA-dependent RNA Polymerase (Primase; RNA Primer Synthesis)

The biological activity also encompasses a DNA-dependent RNA polymerase activity of a polypeptide having the S. aureus STAAU_R9 sequence provided herein, a fragment, or a variant thereof or a protein comprising a S. aureus STAAU_R9 polypeptide or a fragment thereof that directly interacts with bacteriophage 96 ORF 78 protein or a STAAU_R9-binding fragment of the 96 ORF 78 protein, fragment, or variant thereof. A number of methods, useful in the invention, to measure the primase activity of a polypeptide comprising the amino acid sequence of STAAU_R9 are described below.

To assay the RNA primer synthesis activity of STAAU_R9, for example, a solid-phase immunoassay can be used. In the assay, a DNA template for primase is immobilized onto a solid support and then contacted with a reaction mixture that comprises STAAU_R9 primase and ribonucleotide triphosphates. RNA primer synthesis activity present in the mixture results in the polymerization of ribonucleotide triphosphates on the template forming a DNA-RNA heteroduplex. Typically, the heteroduplex is detected either by an antibody that is specific for such DNA-RNA hybrid regions [Mohanram et al., U.S. Pat. No. 6,043,038], or by incorporation into the newly-synthesized RNA portion of the heteroduplex of a label, such as digoxygenin, which itself is readily detected by a label-specific antibody. Bound antibodies are typically detected by a second antibody that is coupled to a chromogenic enzyme or fluorescent label, allowing for rapid quantitation of the bound antibody and thus for quantitation of the original RNA primer synthesis activity within the assay mixture.

iv) The Stimulation of DNA Unwinding Activity by DNA Helicase.

The biological activity also relates to the activity of a polypeptide having the *S. aureus* sequence provided herein, or a protein comprising a *S. aureus* STAAU_R9 polypeptide, a fragment, or variant thereof, to stimulate *S. aureus* DnaC helicase (also referred to DnaB in *E. coli* and in *B. stearothermophilus*) activity in unwinding DNA (e.g. SEQ ID NO 6).

Helicases are capable of unwinding duplex DNA with a 5' to 3' unwinding polarity. The following helicase assay can be adapted from an in vitro assay with DnaB helicase and DnaG primase of *B. stearothermophilus* [Bird, L. E., Pan, H., Soultanas, P., and Wigley, D. B. (2000) Biochem. 39:171-182]. Under the conditions of the assay described below, helicase demonstrates weak DNA unwinding activity in the absence of DnaG primase. To determine the effect of *S. aureus* STAAU_R9 on the unwinding activity of *S. aureus* DnaC helicase, for example, a duplex DNA substrate with a 3' single-stranded (ss) DNA tail (preformed fork) is incubated with a fixed quantity of purified DnaC helicase and increasing amounts of purified STAAU_R9. The reaction mixture is subjected to conditions that support helicase activity.

The reaction contains 50 mM NaCl, 1 mM ATP, 50 μg/ml BSA and 0.24 nM [$^{32}$P]-labeled oligomer annealed to M13 ssDNA. The addition of increasing amounts of DnaG primase to DnaC helicase predictably results in the melting of the DNA duplex such that the radiolabel is separated from the M13mp18 DNA. The separation of the oligonucleotide from the M13mp18 DNA is readily detected by gel electrophoresis and exposure of the gels to autoradiography film. The migration of the unwound radiolabeled oligonucleotide away from the larger duplex DNA is indicative of the presence of helicase unwinding-stimulating activity in the assay mixture.

v) The Stimulation of the DNA Helicase ATPase Activity.

The biological activity also relates to stimulating the activity of a polypeptide derived from the *S. aureus* primase DNA sequence provided herein, or a protein comprising a *S. aureus* STAAU_R9 polypeptide, a fragment or a variant thereof, in stimulating the ATPase activity of DnaC helicase (e.g. SEQ ID NO 6). A number of methods, useful in the invention, to measure the DnaC ATPase stimulating activity of a polypeptide comprising the amino acid sequence of STAAU_R9 are described below.

The ability of DnaG primase to stimulate the ATPase activity of DnaC helicase can be determined in an ATPase assay in which, for example, ATP hydrolysis is measured under steady-state conditions. In the assay, ATP hydrolysis is linked to the oxidation of NADH, which provides for a convenient spectrophotometric determination of ATPase activity. Alternatively, ATPase activity is assayed indirectly by measuring the release of inorganic phosphate (Pi release assay) as a result of ATP hydrolysis by DnaC helicase. The Pi release assay mixture has a total volume of 100 μL and includes DnaC helicase enzyme, DnaG primase, 10 mM MgCl$_2$, 50 mM Hepes pH 7.5, and 1 mM substrate (ATP). After the required incubation time, an equal volume of ammonium molybdate-malachite green reagent is added and the absorbance at 630 nm is measured. The presence of a candidate modulator to the mixture of DnaC helicase and DnaG primase will result in an inhibition of Pi release and will be detected as a reduction in the absorbance at 630 nm of the reaction mixture after addition of ammonium molybdate-malachite green reagent relative to a sample without the candidate inhibitor.

As used herein, the term "polynucleotide encoding a polypeptide" or equivalent language encompasses polynucleotides that include a sequence encoding a polypeptide of the invention, particularly a bacterial polypeptide and more particularly a polypeptide of *S. aureus* STAAU_R9 protein having an amino acid sequence set out in FIG. 1, SEQ ID NO: 2. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or otherwise altered due to RNA editing or genomic DNA reorganization) together with additional regions that also may contain coding and/or non-coding sequences.

As used herein, the term "STAAU_R9 gene" "DnaG gene" is meant to encompass a polynucleotide encoding a *S. aureus* STAAU_R9 polypeptide. Any additional nucleotide sequences necessary to direct transcription of RNA encoding a *S. aureus* STAAU_R9 polypeptide, either in a cell or in vitro, will be termed "regulatory sequences", which include but are not limited to transcriptional promoters and enhancers, and transcription terminators.

As used herein, the term "ORF 78" or "phage 96 ORF 78" or "96 ORF 78" encompasses a polynucleotide represented by the sequence provided in FIG. 2 (SEQ ID NO: 3), which encodes a gene product known as the 96 ORF 78 gene product, and, unless clearly indicated to the contrary, variants thereof that encode products that retain specific binding to the *S. aureus* STAAU_R9 polypeptide. For example, naturally occurring variants of 96 ORF 78 that encode variants of the 96 ORF 78 gene product are included.

As used herein, the term "polynucleotide(s)" generally refers to any polyribonucleotide or poly-deoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s). Polynucleotides can also be DNA and RNA chimeras.

As used herein, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene-encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation, selenoylation, sulfation and transfer-RNA mediated addition of amino acids to proteins, such as arginylation, and ubiquitination. See, for instance: Proteins—Structure and Molecular Properties, 2nd Ed., T. E. Creighton, W.H. Freeman and Company, New York (1993); Wold, F., Posttranslational Protein Modifications: Perspectives and Prospects, pgs. 1-12 in Posttranslational Covalent Modification of Proteins, B. C. Johnson, Ed., Academic Press, New York (1983); Seifter et al., Meth. Enzymol. 182:626-646 (1990); and Rattan et al., Protein Synthesis: Posttranslational Modifications and Aging, Ann. N.Y. Acad. Sci. 663: 48-62(1992). Polypeptides may be branched or cyclic, with or without branching. Cyclic, branched and branched circular polypeptides may result from post-translational natural processes and may be made by entirely synthetic methods, as well.

As used herein, the term "variant(s)" refers to a polynucleotide or polypeptide that differs from a reference polynucleotide or polypeptide, respectively, but retains one or more of the biological activities of the initial (e.g. non-variant) polynucleotide or polypeptide of the present invention (e.g. STAAU_R9). A typical variant of a polynucleotide differs in nucleotide sequence from another reference polynucleotide. Changes in the nucleotide sequence of the variant may or may not alter the amino acid sequence of a polypeptide encoded by the reference polynucleotide. Nucleotide changes may result in amino acid substitutions, additions, deletions, and truncations in the polypeptide encoded by the reference sequence, or in the formation of fusion proteins, as discussed below. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. The present invention also includes variants of each of the polypeptides of the invention, that is polypeptides that vary from the referents by conservative amino acid substitutions whereby a residue is substituted by another with like characteristics. Typically, such substitutions are among Val, Leu and Ile; among Ser and Thr; among the acidic residues Asp and Glu; and among the basic residues Lys and Arg; or aromatic residues Phe and Tyr. Particularly preferred are variants in which 1-10, 1-5, 1-3, 2-3, or 1 amino acid or amino acids are substituted, deleted, or added in any combination. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans. In one embodiment of the present invention, a variant of STAAU_R9 is thus meant to refer to a sequence thereof which diverges in the sequence of SEQ ID NO:2 which is absent in SEQ ID NO:6.

As used herein, the term "fragment", when used in reference to a polypeptide, is a polypeptide having an amino acid sequence that is entirely the same as part but not all of the amino acid sequence of the polypeptide according to the invention from which it "derives". As with S. aureus STAAU_R9 polypeptides, fragments may be "free-standing" ("consisting of"), consisting essentially of, or comprised within a larger polypeptide of which they form a part or region, most preferably as a single continuous region in a single larger polypeptide.

The term "isolated", when used in reference to a nucleic acid means that a naturally occurring sequence has been removed from its normal cellular (e.g., chromosomal) environment or is synthesized in a non-natural environment (e.g., artificially synthesized). Thus, the sequence may be in a cell-free solution or placed in a different cellular environment. The term does not imply that the sequence is the only nucleotide chain present, but that it is essentially free (about 90-95% pure at least) of non-nucleotide material naturally associated with it, and thus is distinguished from isolated chromosomes.

The term "enriched", when used in reference to a polynucleotide means that the specific DNA or RNA sequence constitutes a significantly higher fraction (2-5 fold) of the total DNA or RNA present in the cells or solution of interest than in normal or diseased cells or in cells from which the sequence was originally taken. This could be caused by a person, by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased.

As used herein, the term "significantly higher fraction" indicates that the level of enrichment is useful to the person making such an enrichment and indicates an increase in enrichment relative to other nucleic acids of at least about 2-fold, or 5- to 10-fold or even more. The term also does not imply that there is no DNA or RNA from other sources. The other source of DNA may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

As used herein, the term "purified" in reference to nucleic acid does not require absolute purity (such as a homogeneous preparation). Instead, it represents an indication that the sequence is relatively more pure than in the natural environment (compared to the natural level, this level should be at least 2-5 fold greater, e.g., in terms of mg/mL). Individual clones isolated from a genomic or cDNA library may be purified to electrophoretic homogeneity. The claimed DNA molecules obtained from these clones could be obtained directly from total DNA or from total RNA. cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message over its proportion in naturally occurring cells. Thus, purification of at least one order of magnitude, preferably two or three orders, and more preferably four or five orders of magnitude is expressly contemplated. A genomic library can be used in the same way and yields the same approximate levels of purification.

The terms "isolated", "enriched", and "purified" used with respect to nucleic acids, above, may similarly be used to denote the relative purity and abundance of polypeptides. These, too, may be stored in, grown in, screened in, and selected from libraries using biochemical techniques familiar in the art. Such polypeptides may be natural, synthetic or chimeric and may be extracted using any of a variety of methods, such as antibody immunoprecipitation, other "tagging" techniques, conventional chromatography and/or electrophoretic methods. Some of the above utilize the corresponding nucleic acid sequence.

As used herein, the term "complement" when used in reference to a given polynucleotide sequence refers to a sequence of nucleotides which can form a double-stranded heteroduplex in which every nucleotide in the sequence of nucleotides is base-paired by hydrogen bonding to a nucleotide opposite it in the heteroduplex with the given polynucleotide sequence. The term may refer to a DNA or an RNA sequence that is the complement of another RNA or DNA sequence. As used herein, the term "hybridizes" refers to the formation of a hydrogen-bonded heteroduplex between two nucleic acid molecules. Generally, a given nucleic acid molecule will hybridize with its complement, or with a molecule that is sufficiently complementary to the given molecule to permit formation of a hydrogen-bonded heteroduplex between the two molecules.

As used herein, the term "probe" refers to a polynucleotide of at least 15 nucleotides (nt), 20 nt, 30 nt, 40 nt, 50 nt, 75 nt, 100 nt, 200 nt, 500 nt, 1000 nt, and even up to 5000 to 10,000 nt in length.

"Identity" and "similarity," as used herein and as known in the art, are relationships between two or more polypeptide sequences or two or more polynucleotide sequences, as the case may be, as determined by comparing the sequences.

Amino acid or nucleotide sequence "identity" and "similarity" are determined from an optimal global alignment between the two sequences being compared. A non-limiting example of optimal global alignment can be carried-out using the Needleman-Wunsch algorithm (Needleman and Wunsch, 1970, J. Mol. Biol. 48:443-453). "Identity" means that an amino acid or nucleotide at a particular position in a first polypeptide or polynucleotide is identical to a corresponding amino acid or nucleotide in a second polypeptide or polynucleotide that is in an optimal global alignment with the first polypeptide or polynucleotide. In contrast to identity, "similarity" encompasses amino acids that are conservative substitutions.

The term "conservative" substitution is well-known in the art and broadly refers to a substitution which does not significantly change the chemico-physical properties of the substituted amino acid. For example, a "conservative" substitution is any substitution that has a positive score in the blosum62 substitution matrix (Hentikoff and Hentikoff, 1992, Proc. Natl. Acad. Sci. USA 89: 10915-10919). By the statement "sequence A is n % similar to sequence B" is meant that n % of the positions of an optimal global alignment between sequences A and B consists of identical residues and conservative substitutions. By the statement "sequence A is n % identical to sequence B" is meant that n % of the positions of an optimal global alignment between sequences A and B consists of identical residues or nucleotides. Optimal global alignments in this disclosure used the following parameters in the Needleman-Wunsch alignment algorithm:

For Polypeptides:
  Substitution matrix: blosum62.
  Gap scoring function: $-A-B*LG$, where A=11 (the gap penalty), B=1 (the gap length penalty) and LG is the length of the gap.

For nucleotide sequences:
  Substitution matrix: 10 for matches, 0 for mismatches.
  Gap scoring function: $-A-B*LG$ where A=50 (the gap penalty), B=3 (the gap length penalty) and LG is the length of the gap.

The term 'identity' and 'similarity' between sequences can be extended to their fragments. An optimal local alignment between sequences A and B is the highest scoring alignment of fragments of A and B. By the statement "sequence A is n % similar locally to B" is meant that n % of the positions of an optimal local alignment between sequences A and B consists of conservative substitutions and identical residues. By the statement "sequence A is n % identical locally to B" is meant that n % of the position of an optimal local alignment between sequences A and B consists of identical residues or nucleotides. A non-limiting example of optimal local alignment can be carried-out using the Smith-Waterman algorithm [Smith, T. F and Waterman, M. S. 1981. Identification of common molecular subsequences. J. Mol. Biol. 147:195-197].

Of course, the above-listed parameters are but one specific example of alignment algorithm parameters. Numerous algorithms and parameters are available and known to the person of ordinary skill.

Typical conservative substitutions are among Met, Val, Leu and Ile; among Ser and Thr; among the residues Asp, Glu and Asn; among the residues Gin, Lys and Arg; or aromatic residues Phe and Tyr. In calculating the degree (most often as a percentage) of similarity between two polypeptide sequences, one considers the number of positions at which identity or similarity is observed between corresponding amino acid residues in the two polypeptide sequences in relation to the entire lengths of the two molecules being compared.

As used herein, the term "antibody" is meant to encompass constructions using the binding (variable) region of such an antibody, and other antibody modifications. Thus, an antibody useful in the invention may comprise a whole antibody, an antibody fragment, a polyfunctional antibody aggregate, or in general a substance comprising one or more specific binding sites from an antibody. The antibody fragment may be a fragment such as an Fv, Fab or F(ab')$_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate. Neutralizing antibodies are especially useful according to the invention for diagnostics, therapeutics and methods of drug screening and drug design.

As used herein, the term "specific for an epitope present on a S. aureus STAAU_R9 polypeptide", when used in reference to an antibody, means that the antibody recognizes and binds an antigenic determinant present on a S. aureus STAAU_R9 polypeptide or fragment thereof (e.g. SEQ ID NO: 6) according to the invention.

As used herein, the term "antigenically equivalent derivative(s)" encompasses a polypeptide, polynucleotide, or the equivalent of either which will be specifically recognized by certain antibodies which, when raised to the protein, polypeptide or polynucleotide according to the invention, interferes with the immediate physical interaction between pathogen and mammalian host.

As used herein, the term "essential", when used in connection with a gene or gene product, means that the host cannot survive without, or is significantly growth compromised, in the absence or depletion of functional product. An "essential gene" is thus one that encodes a product that is beneficial, or preferably necessary, for cellular growth in vitro in a medium appropriate for growth of a strain having a wild-type allele corresponding to the particular gene in question. Therefore, if an essential gene is inactivated or inhibited, that cell will grow significantly more slowly than a wild-type strain or even not at all. Preferably, growth of a strain in which such a gene has been inactivated will be less than 20%, more preferably less than 10%, most preferably less than 5% of the growth rate of the wild-type, or the rate will be zero, in the growth medium. Preferably, in the absence of activity provided by a product of the gene, the cell will not grow at all or will be non-viable, at least under culture conditions similar to normal in vivo growth conditions. For example, absence of the biological activity of certain enzymes involved in bacterial cell wall synthesis can result in the lysis of cells under normal osmotic conditions, even though protoplasts can be maintained under controlled osmotic conditions. Preferably, but not necessarily, if such a gene is inhibited, e.g., with an antibacterial agent or a phage product, the growth rate of the inhibited bacteria will be less than 50%, more preferably less than 30%, still more preferably less than 20%, and most preferably less than 10% of the growth rate of the uninhibited bacteria. As recognized by those skilled in the art, the degree of growth inhibition will generally depend upon the concentration of the inhibitory agent. In the context of the invention, essential genes are generally the preferred targets of antimicrobial agents. Essential genes can encode "target" molecules directly or can encode a product involved in the production, modification, or maintenance of a target molecule.

As used herein, "target" refers to a biomolecule or complex of biomolecules that can be acted on by an exogenous agent or compound, thereby modulating, preferably inhibiting, growth or viability of a bacterial cell. A target may be a nucleic acid sequence or molecule, or a polypeptide or a region of a polypeptide.

As used herein, the term "signal that is generated by interaction of a S. aureus polypeptide comprising the amino acid sequence of SEQ ID NO: 2, or fragments thereof to a 96 ORF 78 or fragment thereof" or the like refers to the measurable indicator of polypeptide interaction in a binding assay, wherein the interacting polypeptide comprises the amino acid sequence of SEQ ID NO: 2, fragment thereof or variant thereof and 96 ORF 78, fragment thereof or variant thereof. As used herein, the term "signal that is generated by activation or inhibition of a S. aureus polypeptide comprising the amino acid sequence of SEQ ID NO: 2, or fragments thereof" refers to the measurable indicator of polypeptide comprising the amino acid sequence of SEQ ID NO: 2, fragment or variant thereof, activity in an assay of STAAU_R9 activity. For example, the signal may include, but is not limited to (i) a signal resulting from binding of 96 ORF 78 to a STAAU_R9 polypeptide, including a fluorescence signal (time-resolved fluorescence resonance energy transfer assay; fluorescence polarization assay), spectrophotometer absorbance measurement of a colourimetric signal (phage display ELISA), mass change measurement (surface plasmon resonance analysis), or a viability measurement on selective medium (yeast two-hybrid analysis); or (ii) a reduction of a radiolabeled signal (DNA synthesis assay).

As used herein, the term "standard", used in reference to polypeptide activity, means the amount of activity observed or detected (directly or indirectly) in a given assay performed in the absence of a candidate compound. A "standard" serves as a reference to determine the effect, positive or negative, of a candidate compound on polypeptide activity.

As used herein, the term "increase in activity" refers to an enhanced level of measurable activity of a polypeptide in a given assay in the presence of a candidate compound relative to the measurable level of activity in the absence of a candidate compound. Activity is considered increased according to the invention if it is at least 10% greater, 20% greater, 50% greater, 75% greater, 100% greater or more, up to 2-fold, 5-fold, 10-fold, 20-fold, 50-fold, 100-fold or more than in the absence of a candidate compound.

As used herein, the term "decrease in activity" refers to a reduced level of measurable activity of a polypeptide in a given assay in the presence of a candidate compound relative to the measurable level of activity in the absence of a candidate compound. Activity is considered decreased according to the invention if it is at least 10% less, preferably 15% less, 20% less, 50% less, 75% less, or even 100% less (i.e., no activity) than that observed in the absence of a candidate compound.

As used herein, the term "conditions that permit their interaction", when used in reference to a S. aureus polypeptide comprising the amino acid sequence of SEQ ID NO: 2, or fragments thereof, and a candidate compound means that the two entities are placed together, whether both in solution or with one immobilized or restricted in some way and the other in solution, wherein the parameters (e.g., salt, detergent, protein or candidate compound concentration, temperature, and redox potential, among others) of the solution are such that the S. aureus polypeptide comprising the amino acid sequence of SEQ ID NO: 2, or fragments thereof, and the candidate compound may physically associate. Conditions that permit protein:candidate interaction include, for example, the conditions described herein for TR-FRET, fluorescent polarization, Surface Plasmon Resonance and Phage display assays.

As used herein, the term "detectable change in a measurable parameter of STAAU_R9" refers to an alteration in a quantifiable characteristic of a S. aureus STAAU_R9 polypeptide.

As used herein, the term "agonist" refers to an agent or compound that enhances or increases the activity of a S. aureus STAAU_R9 polypeptide or polynucleotide. An agonist may be directly active on a S. aureus STAAU_R9 polypeptide or polynucleotide, or it may be active on one or more constituents in a pathway that leads to enhanced or increased activity of a S. aureus STAAU_R9 polypeptide or polynucleotide.

As used herein, the term "antagonist" refers to an agent or compound that reduces or decreases the activity of a S. aureus STAAU_R9 polypeptide or polynucleotide. An antagonist may be directly active on a S. aureus STAAU_R9 polypeptide or polynucleotide, or it may be active on one or more constituents in a pathway that leads to reduced or decreased activity of a S. aureus STAAU_R9 polypeptide or polynucleotide.

As used herein, the term "antibacterial agent" or "antibacterial compound" refers to an agent or compound that has a bacteriocidal or bacteriostatic effect on one or more bacterial strains, preferably such an agent or compound is bacteriocidal or bacteriostatic on at least S. aureus.

As used herein, the term "synthesizing" refers to a process of chemically synthesizing a compound.

As used in the context of treating a bacterial infection a "therapeutically effective amount", "pharmaceutically effective amount" or "amount sufficient to provide a therapeutic effect" indicates an amount of an antibacterial agent which has a therapeutic effect. This generally refers to the inhibition, to some extent, of the normal cellular functioning of bacterial cells required for continued bacterial infection. Further, as used herein, a therapeutically effective amount means an amount of an antibacterial agent that produces the desired therapeutic effect as judged for example by clinical trial results and/or animal models. This amount can be routinely determined by one skilled in the art and will vary depending on several factors, such as the particular bacterial strain involved and the particular antibacterial agent used. In the same context, an "amount sufficient to reduce adhesion" of a bacterium to a tissue or tissue surface indicates an amount of an antibacterial agent that is effective for prophylactically preventing or reducing the extent of bacterial infection of the given tissue or tissue surface.

As used in the context of treating a bacterial infection, contacting or administering the antimicrobial agent 'in combination with existing antimicrobial agents' refer to a concurrent contacting or administration of the active compound with antibiotics to provide a bactericidal or growth inhibitory effects beyond the individual bactericidal or growth inhibitory effects of the active compound or the antibiotic. Existing antibiotic refers for example to the group consisting of penicillins, cephalosporins, imipenem, monobactams, aminoglycosides, tetracyclines, sulfonamides, trimethoprim/sulfonamide, fluoroquinolones, macrolides, vancomycin, polymyxins, chloramphenicol and lincosamides.

As used herein, a "tissue" refers to an aggregation of cells of one or more cell types which together perform one or more specific functions in an organism. As used herein, a "tissue surface" refers to that portion of a tissue that forms a boundary between a given tissue and other tissues or the surroundings of the tissue. A tissue surface may refer to an external surface of an animal, for example the skin or cornea, or, alternatively, the term may refer to a surface that is either internal, for example, the lining of the gut, or to a surface that is exposed to the outside surroundings of the animal only as the result of an injury or a surgical procedure.

As used herein, the term "measuring the binding of a candidate compound" refers to the use of an assay permitting the quantitation of the amount of a candidate compound physically associated with a S. aureus STAAU_R9 polypeptide, fragment or variant thereof.

A "candidate compound" as used herein, is any compound with a potential to modulate the expression or activity of a S. aureus STAAU_R9 polypeptide.

As used herein, the term "simultaneously" when used in connection with the assays of the present invention, refers to the fact that the specified components or actions at least overlap in time, and is thus not restricted to the fact that the initiation and termination points are identical. For certainty, a simultaneous contact of a STAAU_R9 polypeptide with a candidate compound and a bacteriophage polypeptide is an overlap in contact periods, which can but does not necessarily reflect the fact that the latter two are introduced into an assay mixture at the exact same time.

As used herein, the term "directly or indirectly detectably labeled" refers to the attachment of a moiety to a candidate compound that renders the candidate compound either directly detectable (e.g., an isotope or a fluorophore) or indirectly detectable (e.g., an enzyme activity, allowing detection in the presence of an appropriate substrate, or a specific antigen or other marker allowing detection by addition of an antibody or other specific indicator).

A "method of screening" refers to a method for evaluating a relevant activity or property of a large plurality of compounds, rather than just one or a few compounds. For example, a method of screening can be used to conveniently test at least 100, more preferably at least 1000, still more preferably at least 10,000, and most preferably at least 100,000 different compounds, or even more. In a particular embodiment, the method is amenable to automated, cost-effective high throughput screening on libraries of compounds for lead development.

In a related aspect or in preferred embodiments, the invention provides a method of screening for potential antibacterial agents by determining whether any of a plurality of compounds, preferably a plurality of small molecules, is active on STAAU_R9. Preferred embodiments include those described for the above aspect, including embodiments which involve determining whether one or more test compounds bind to or reduce the level of activity of a bacterial target, and embodiments which utilize a plurality of different targets as described above.

The term "compounds" includes, but is not limited to, small organic molecules, peptides, polypeptides and antibodies that bind to a polynucleotide and/or polypeptide of the invention, such as for example inhibitory ORF gene product or target thereof, and thereby inhibit, extinguish or enhance its activity or expression. Potential compounds may be small organic molecules, a peptide, a polypeptide such as a closely related protein or antibody that binds the same site(s) on a binding molecule, such as a bacteriophage gene product, thereby preventing bacteriophage gene product from binding to STAAU_R9 polypeptides.

The term "compounds" also potentially includes small molecules that bind to and occupy the binding site of a polypeptide, thereby preventing binding to cellular binding molecules, such that normal biological activity is prevented. Examples of small molecules include but are not limited to small organic molecules, peptides or peptide-like molecules. Preferred potential compounds include compounds related to and variants of inhibitory ORF products encoded by a bacteriophage and of STAAU_R9 and any homologues and/or peptido-mimetics and/or fragments thereof. Other examples of potential polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented. Other potential compounds include antisense molecules (see Okano, 1991 J. Neurochem. 56, 560; see also "Oligodeoxynucleotides as Antisense Inhibitors of Gene Expression", CRC Press, Boca Raton, Fla. (1988), for a description of these molecules).

As used herein, the term "library" refers to a collection of at least 100 compounds, preferably at least 1000, still more preferably at least 5000, still more preferably 10,000 or more, and most preferably of 50,000 or more compounds.

As used herein, the term "small molecule" refers to compounds having molecular mass of less than 3000 Daltons, preferably less than 2000 or 1500, still more preferably less than 1000, and most preferably less than 600 Daltons. Preferably but not necessarily, a small molecule is not an oligopeptide.

As used herein, the term "mimetic" refers to a compound that can be natural, synthetic, or chimeric and is structurally and functionally related to a reference compound. In terms of the present invention, a "peptidomimetic," for example, is a non-peptide compound that mimics the activity-related aspects of the 3-dimensional structure of a peptide or polypeptide, for example a compound that mimics the structure of a peptide or active portion of a phage- or bacterial ORF-encoded polypeptide.

As used herein, the term "bacteriophage inhibitor protein" refers to a protein encoded by a bacteriophage nucleic acid sequence, which inhibits bacterial function in a host bacterium. Thus, it is a bacteria-inhibiting phage product. The term "bacteriophage inhibitor protein" encompasses a fragment, derivative, or active portion of a bacteriophage inhibitor protein.

In more than one embodiment of the above assay methods of the present invention, it may be desirable to immobilize either STAAU_R9 or its target molecule or ligand to facilitate separation of complexed from uncomplexed forms of one or both of the proteins or polypeptides, as well as to accommodate automation of the assay. Binding of a test compound to a STAAU_R9 protein (or fragment, or variant thereof) or interaction of a STAAU_R9 protein with a target molecule or ligand in the presence and absence of a candidate compound, can be accomplished in any vessel suitable for containing the reactants.

Examples of such vessels include microtitre plates, test tubes and micro-centrifuge tubes.

In one embodiment a fusion protein can be provided which adds a domain that allows one or both of the proteins to be bound to a matrix. For example, glutathione-S-transferase/STAAU_R9 fusion proteins or glutathione-S-transferase/target fusion proteins (e.g. glutathione-S-transferase/ 96 ORF 78) can be adsorbed onto glutathione sepharose beads (Sigma Chemical, St. Louis, Mo.) or glutathione derivatized microtitre plates, which are then combined with the test compound or the test compound and either the non-adsorbed target protein or STAAU_R9 protein and the mixture incubated under conditions conducive to complex formation (e.g. at physiological conditions for salt and pH). Following incubation the beads or microtitre plate wells are washed to remove any unbound components, the matrix immobilized in the case of beads, complex determined either directly or indirectly, for example, as described above. Alternatively, the complexes can be dissociated from the matrix, and the level of STAAU_R9 binding or activity determined using standard techniques.

Other techniques for immobilizing proteins on matrices (and well-known in the art) can also be used in the screening assays of the invention. For example, either a STAAU_R9 protein or a STAAU_R9 target molecule or ligand can be immobilized utilizing conjugation of biotin and streptavidin. Biotinylated STAAU_R9 protein or target molecules or ligand can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with target molecules or ligand but which do not interfere with binding of the STAAU_R9 protein (or part thereof to its target molecule or ligand can be derivatized to the wells of the plate, and unbound target or STAAU_R9 protein trapped in the wells by antibody conjugation. Methods for detecting such complexes, in addition to those described above for the GST-immobilized complexes, include immunodetection of complexes using antibodies reactive with the STAAU_R9 protein or target molecule, as well as enzyme-linked assays which rely on detecting an enzymatic activity associated with the STAAU_R9 protein.

As used herein, the term "active portion", when refering to a bacteriophage-derived sequence, relates to an epitope, a catalytic or regulatory domain, or a fragment of a bacteriophage inhibitor protein that is responsible for, or a significant factor in, bacterial target inhibition. The active portion preferably may be removed from its contiguous sequences and, in isolation, still effect inhibition.

As used herein, the term "treating a bacterial infection" refers to a process whereby the growth and/or metabolic activity of a bacterium or bacterial population in a host, preferably a mammal, more preferably a human, is inhibited or ablated.

As used herein, the term "bacterium" refers to a single bacterial strain and includes a single cell and a plurality or population of cells of that strain unless clearly indicated to the contrary. In reference to bacteria or bacteriophage, the term "strain" refers to bacteria or phage having a particular genetic content. The genetic content includes genomic content as well as recombinant vectors. Thus, for example, two otherwise identical bacterial cells would represent different strains if each contained a vector, e.g., a plasmid, with different inserts.

As used herein, the term "diagnosing" refers to the identification of an organism or strain of an organism responsible for a bacterial infection.

As used herein, the term "infection with *Staphylococcus aureus*" refers to the presence, growth or proliferation of cells of a *S. aureus* strain within, or on a surface of, an animal, such as a mammal, preferably a human.

As used herein, the term "bacteriophage 96 ORF 78-encoded polypeptide" refers to a polypeptide encoded by SEQ ID NO: 3 or to a fragment or derivative thereof encompassing an active portion of a bacteriophage 96 ORF 78-encoded polypeptide of sequence disclosed in SEQ ID NO: 4.

As used herein, the term "polypeptide complex" refers to a combination of two or more polypeptides in a physical association with each other. It is preferred that such a physical association be required for some aspect of the activity of one or more of the polypeptides in such a polypeptide complex.

As used herein, the term "physical association" refers to an interaction between two moieties involving contact between the two moieties.

As used herein, the term "bodily material(s)" means any material derived from an individual or from an organism infecting, infesting or inhabiting an individual, including but not limited to, cells, tissues and waste, such as, bone, blood, serum, cerebrospinal fluid, semen, saliva, muscle, cartilage, organ tissue, skin, urine, stool or autopsy materials.

As used herein, the term "disease(s)" means any disease caused by or related to infection by a bacterium, including, for example, otitis media, conjunctivitis, pneumonia, bacteremia, meningitis, sinusitis, pleural empyema and endocarditis, and most particularly meningitis, such as for example infection of cerebrospinal fluid.

As used herein, the term "fusion protein(s)" refers to a protein encoded by a gene comprising amino acid coding sequences from two or more separate proteins fused in frame such that the protein comprises fused amino acid sequences from the separate proteins.

As used herein, the term "host cell(s)" is a cell which has been transformed or transfected, or is capable of transformation or transfection by an exogenous polynucleotide sequence.

As used herein, the term "immunologically equivalent derivative(s)" encompasses a polypeptide, polynucleotide, or the equivalent of either which when used in a suitable formulation to raise antibodies in a vertebrate, results in antibodies that act to interfere with the immediate physical interaction between pathogen and mammalian host.

As used herein, the term "immunospecific" means that characteristic of an antibody whereby it possesses substantially greater affinity for the polypeptides of the invention or the polynucleotides of the invention than its affinity for other related polypeptides or polynucleotides respectively, particularly those polypeptides and polynucleotides in the prior art.

As used herein, the term "individual(s)" means a multi-cellular eukaryote, including, but not limited to a metazoan, a mammal, an ovid, a bovid, a simian, a primate, and a human.

As used herein, the term "Organism(s)" means a (i) prokaryote, including but not limited to, a member of the genus *Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia* and *Mycoplasma*, and further including, but not limited to, a member of the species or group, Group A *Streptococcus*, Group B *Streptococcus*, Group C *Streptococcus*, Group D *Streptococcus*, Group G *Streptococcus, Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi, Bordetella, Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium perfringens, Clostridium tetani, Clostridium botulinum, Treponema pallidum, Rickettsia rickettsii* and *Chlamydia trachomitis*, (ii) an archaeon, including but not limited to *Archaebacter*, and (iii) a unicellular or filamenous eukaryote, including but not limited to, a protozoan, a fungus, a member of the genus *Saccharomyces, Kluveromyces,* or *Candida*, and a member of the species *Saccharomyces ceriviseae, Kluveromyces lactis*, or *Candida albicans*.

As used herein, the term "recombinant expression system(s)" refers to a system in which vectors comprising sequences encoding polypeptides of the invention or portions thereof, or polynucleotides of the invention are introduced or transformed into a host cell or host cell lysate for the production of the polynucleotides and polypeptides of the invention.

As used herein, the term "artificially synthesized" when used in reference to a peptide, polypeptide or polynucleotide means that the amino acid or nucleotide subunits were chemically joined in vitro without the use of cells or polymerizing enzymes. The chemistry of polynucleotide and peptide synthesis is well known in the art.

In addition to the standard single and triple letter representations for amino acids, the term "X" or "Xaa" may also be used in describing certain polypeptides of the invention. "X" and "Xaa" mean that any of the twenty naturally occurring amino acids may appear at such a designated position in the polypeptide sequence.

As used herein, the term "specifically binding" in the context of the interaction of two polypeptides means that the two polypeptides physically interact via discrete regions or domains on the polypeptides, wherein the interaction is dependent upon the amino acid sequences of the interacting domains or on interacting residues within such regions or domains. Generally, the equilibrium binding concentration of a polypeptide that specifically binds another is in the range of about 1 mM or lower, more preferably 1 uM or lower, preferably 100 nM or lower, 10 nM or lower, 1 nM or lower, 100 pM or lower, and even 10 pM or lower.

As used herein, the term "decrease in the binding" refers to a drop in the signal that is generated by the physical association between two polypeptides under one set of conditions relative to the signal under another set of reference conditions. The signal is decreased if it is at least 10% lower than the level under reference conditions, and preferably 20%, 40%, 50%, 75%, 90%, 95% or even as much as 100% lower (i.e., no detectable interaction).

As used herein, the term "detectable marker", when used in the context of a yeast two-hybrid assay, refers to a polypeptide that confers a trait upon a cell expressing that polypeptide that signals the presence or amount of that polypeptide expressed. Detectable markers are encoded on plasmids that may exist episomally or may be integrated into the genome of a host cell. Detectable markers include, but are not limited to, polypeptides encoding enzymes allowing calorimetric or fluorescent detection (e.g., *E. coli* LacZ, which catalyzes the conversion of the substrate analog X-gal to generate a blue color), polypeptides encoding enzymes conferring antibiotic resistance, and polypeptides encoding enzymes conferring the ability of a yeast strain to grow on medium lacking a given component (i.e., critical for the relief of auxotrophy).

As used herein, the term "results in the expression of a detectable marker" means that the interaction of factors necessary to permit the expression of a detectable marker (e.g., two-hybrid transactivation domain and DNA binding domain fusion proteins) causes the transactivation and translation of detectable levels of a detectable marker. A "detectable level" is that level of expression that can be differentiated from background expression occurring in the substantial absence of one or more factors or conditions necessary for marker expression. Detectable levels will vary depending upon the nature of the detectable marker, but will generally consist of levels at least about 10% or more greater than the background level of a given marker.

As used herein, the term "decrease in the expression" refers to a drop in the expression of a detectable marker under one set of conditions relative to the expression under another set of reference conditions. The expression of a detectable marker is decreased if it is at least 10% lower than the level under reference conditions, and preferably 20%, 40%, 50%, 75%, 90%, 95% or even as much as 100% lower (i.e., not expressed).

Identification of the *S. aureus* STAAU R9 Sequence

The methodology used to identify the STAAU_R9 polypeptide is described in detail in U.S. Provisional Patent Application No. 60/110,992, filed Dec. 3, 1998, and PCT International Application W01999/IB99/02040, filed Dec. 3, 1999. Briefly, this PCT application concerns bacteriophages that can infect a selected bacterium. The sequencing and characterization of the phage genetic information allow the identification of all open reading frames (ORFs) encoded by the phage, including those that are essential or instrumental in inhibiting their host. Each ORF is identified using computer softwares and individually expressed in the host. The effect of this expression on host viability is then measured. Identification of ORFs from the phage genome which inhibit the host bacterium both provides a compound that could be used as a bacterial inhibitor compound per se (or derivatized or modified to obtain further inhibitors) and as a tool for the identification of the bacterial target affected by the phage-encoded inhibitor.

Using methodology described in detail in Example 1 and 2, a *S. aureus* polypeptide that specifically bound the bacterial growth inhibitory 96 phage ORF 78 protein was isolated. Briefly, the 96 ORF 78 protein was used as a ligand in an affinity chromatography binding step with *S. aureus* protein extract. The selected *S. aureus* interacting polypeptide was purified and further analyzed by tryptic digestion and mass spectrometry using MALDI-ToF technology [Qin, J., et al. (1997) *Anal. Chem.* 69:3995-4001]. Computational analysis (http://prowl.rockfeller.edu/cgi-bin/ProFound) of the mass spectrum obtained identifies the corresponding ORF in the *S. aureus* nucleotide sequence in the University of Oklahoma *S. aureus* genomic database at http://www-.genome.ou.edu/staph.html. The interaction between 96 ORF 78 and the candidate target protein, herein referred as STAAU_R9 or fragment thereof, was also confirmed in a yeast two-hybrid assay. The interactions between bacterial STAAU_R9 or fragment thereof and 96 ORF 78 were further characterized using affinity blotting and surface plasmon resonance assays.

The sequence similarity between individual members of evolutionarily distant members of a protein family is usually not randomly distributed along the entire length of the sequence but is often clustered into "domains". These correspond to conserved three-dimensional folds that form catalytic and/or regulatory structures that perform the important biochemical function of the group of proteins. Commercially and publicly available computer software programs can identify such motifs and domains in a new query sequence, providing additional functional information for the query sequence. Such motifs and folds are themselves deposited in public databases which can be directly accessed (for example, SwissProt database; 3D-ALI at EMBL, Heidelberg; Pfam; Blocks: PROSITE).

The *S. aureus* STAAU_R9 identified in the phage 96 ORF 78 binding studies was compared with all other sequences in the public domain databases. As shown in FIG. 7B, results revealed that STAAU_R9 is related to a large number of bacterial DNA primases, including those of *B. stearothermophilus* (34% identity), *B. subtilis* (36% identity) and *E. coli* (27% identity). More specifically, STAAU_R9 is highly related to the *S. aureus* strain 912 DNA primase (gi|2494147|sp|O05338|PRIM_STAAU DNA PRIMASE) with a 92% amino acid identity and 93% similarity at the amino acid level across the entire sequence.

The results of a Hidden Markov Model searching analysis of the STAAU_R9 amino acid sequence revealed the presence of two highly related Pfam motifs in the STAAU_R9 region spanning amino acids 1 to 339 (FIG. 7A). A N-terminal CHC2 zinc finger domain extends from the amino acids position 3 to 100, and the Toprim domain, located centrally (amino acid position 260 to 339), corresponds to a conserved catalytic domain in bacterial DnaG-type primases.

Function of DNA Primase

Nucleic acid metabolism is essential for all cells. The DNA synthesis machinery includes a number of proteins that act in concert to achieve rapid and highly processive replication of the chromosome in bacteria [reviewed in Kornberg, A., and Baker, T. A. 1992, *DNA Replication*, Second edition, New York: W.H. Freeman and Company, pp. 165-194]. Coordinated interactions among proteins of the bacterial primosome and replisome are essential to its efficiency. DNA primases play an essential role in chromosome replication because in addition to initiating leading-strand synthesis, they synthesize short RNA primers on the lagging strand and thus allow for replication of the lagging strand during chromosomal replication. The primase genes of both *B. subtilis* and *E. coli*, dnaG, were isolated in studies with conditionally-lethal temperature-sensitive DNA replication mutants [Rowen, L. and Kornberg, A. 1978, J. Biol. Chem. 253:758-64; Alonso, J. C. et al. 1988, Mol. Gen. Genet. 214: 482-489].

*E. coli* DnaG interacts with the replicative DNA helicase, DnaB, within the primosome to achieve regulated synthesis of RNA primers used to prime DNA synthesis of the lagging strand. DNA helicase is thought to unwind duplex DNA progressively and allow for binding of the DNA polymerase III holoenzyme necessary for DNA synthesis. The DnaG primase of *E. coli* comprises two functional domains: a N-terminal 49 kDa domain that retains template recognition- and primase activities in replication assays; and a C-terminal 16 kDa domain that is required for functional interaction with DnaB [Tougu, K., et al. 1994, J. Biol. Chem. 269:4675-4682; Lu, Y.-B., et al. 1996, Proc. Natl. Acad. Sci. U.S.A. 93:12902-12907]. Further delimitation of the DnaB helicase-binding region of DnaG primase revealed that only the C-terminal 16 amino acids of DnaG are required for functional interaction with *E. coli* DnaB [Tougu, K., and Marians, K. J. 1996, J. Biol. Chem. 271:21398-21405].

Extensive characterization of the interactions between DnaG primase and DnaB helicase of *B. stearothermophilus* [Bird, L. E., et al. 2000, Biochem. 39:171-182] stemmed from the observation that the two proteins form a stable complex in vitro. Systematic truncation of *B. stearothermophilus* primase and helicase, using limited proteolysis and PCR mutagenesis, followed by gel filtration and biochemical assays revealed that the C-terminal domain of primase is sufficient to interact with DnaB and to stimulate the ATPase and helicase activities of DnaB helicase. Although it has not been tested directly, the N-terminus of *B. stearothermophilus* primase contains signature primase domains and thus the organization of *B. stearothermophilus* primase is likely to match that of *E. coli* primase.

In addition to its interactions with helicase, primase also undergoes physical interactions with the *E. coli* DNA polymerase III holoenzyme (DNA Pol III HE) [Wu, C. A., et al. 1992, J. Biol. Chem. 267:4074-4083]. The association of primase with the DNA Pol III HE during primer synthesis regulates its catalytic activity and this regulatory interaction occurs independently of formation of a preinitiation complex of the DNA Pol III HE on the primer terminus.

*E. coli* DnaG primase also binds to the single-stranded DNA binding protein SSB within the replication fork. The primase-SSB interaction is essential for tight association between primase and the nascent RNA primer. However, in order for the DNA polymerase III β subunit, the sliding clamp, to be assembled onto the primed site, primase must first be displaced from its RNA primer. This displacement function is mediated by a single subunit of the DNA Pol III HE, chi, in conjunction with SSB [Yuzhakov, A., et al. 1999, Cell 96:153-163].

In summary, *E. coli* primase has been shown to interact with several members of the DNA replication machinery, namely helicase, the DNA Pol III HE, and SSB. Binding sites on DnaG for its interaction with the DNA Pol III HE and with SSB are poorly understood at present. In Gram-positive bacteria such as *B. stearothermophilus*, DnaG primase was shown to contain three domains: a) a 12 kDa N-terminal zinc-binding domain which is central for its ability to recognize template DNA; b) a 36 kDa catalytic core domain essential to polymerize ribonucleotides on a DNA template; and c) a C-terminal 15 kDa DnaB-binding domain which allows interaction with helicase.

The cellular functions and the binding partners of *S. aureus* STAAU_R9 are still unclear and could at best be suggested from polypeptide similarities with the other bacterial primases. Based on sequence analysis, *S. aureus* STAAU_R9 likely contains a) an N-terminal zinc-binding domain that could be involved in template DNA recognition; and b) a central catalytic core domain. As shown from the optimal global alignment analysis of amino acid sequence of STAAU_R9-related proteins, the C-terminal region of STAAU_R9 is only weakly conserved amongst bacterial DNA primases (FIG. 7B).

Homologues of DnaG have been identified in all prokaryotes studied to date and in several bacteriophages. Based on comparative sequence analyses, these primases appear structurally distinct from the primases that are essential to archaeal and eukaryotic chromosome replication. It is therefore difficult to predict a priori which of the *S. aureus* DnaG interactions, if any, could be targeted by a compound that would inhibit primase activity, namely ribonucleotide polymerization on a DNA template, stimulation of helicase unwinding activity, stimulation of helicase ATPase activity, or binding to other cellular components.

Surprisingly, despite the demonstration of protein-protein interactions of primase with helicase, with DNA Pol III HE, and with SSB in vitro, and despite evidence that these interactions within the primosome are critical to obtaining efficient primase activities and chromosome replication in vivo [Lu, Y.,et al. 1996, Proc. Natl. Acad. Sci. U.S.A. 93:12902-12907], there are currently no available drugs directed against primase.

The demonstration that bacteriophage have adapted to inhibiting a host bacterium by acting on a particular cellular component or target provides a strong indication that this component is an appropriate target for developing and using antibacterial agents, e.g. in therapeutic treatments. The present invention provides additional guidance over mere identification of bacterial essential genes, as the present invention also provides an indication of accessibility of the target to an inhibitor, and an indication that the target is sufficiently stable over time (e.g., not subject to high rates of mutation) as phage acting on that target were able to develop and persist. Thus the present invention identifies STAAU_R9, and more particularly, a polypeptide comprising the amino acid sequence of SEQ ID NO: 6, as an appropriate target for development of antibacterial agents.

Identification of the Surface of Interaction on STAAU_R9

This invention relates, in part, to a specific interaction between a growth-inhibitory protein encoded by the *S. aureus* bacteriophage genome and an essential *S. aureus* protein. In one embodiment, this interaction forms the basis for drug screening assays. More specifically, the invention relates to the interacting domains of the protein encoded by the *S. aureus* STAAU_R9 and the *S. aureus* bacteriophage 96 ORF 78 proteins, forming the basis for screening assays. The invention provides a method for the identification of 96

ORF 78 and, more preferably, STAAU_R9 polypeptide fragments which are involved in the interaction between STAAU_R9 and 96 ORF 78.

Several approaches and techniques known to those skilled in the art can be used to identify and to characterize interacting fragments of STAAU_R9 and 96 ORF 78. These fragments may include, for example, truncation polypeptides having a portion of an amino acid sequence of any of the two proteins, or variants thereof, such as a continuous series of residues that includes an amino- and/or carboxyl-terminal amino acid sequence.

Fragments of STAAU_R9 and 96 ORF 78 can be cloned by genetic recombinant technology and tested for interaction using a yeast two-hybrid assay as exemplified below.

Partial proteolysis of proteins in solution is one method to delineate the domain boundaries in multi-domain proteins. By subjecting proteins to limited digestion, the most accessible cleavage sites are preferentially hydrolyzed. These cleavage sites preferentially reside in less structured regions which include loops and highly mobile areas typical of the joining amino acids between highly structured domains. Purified STAAU_R9 and 96 ORF 78 proteins can be subjected to partial proteolysis. The proteolysis can be performed with low concentrations of proteases (trypsin, chymotrypsin, endoproteinase Glu-C, and Asp-N) with STAAU_R9 or 96 ORF 78 in solution, resulting in the generation of defined proteolytic products as observed by SDS-PAGE. An acceptable concentration and reaction time is defined by the near complete conversion of the full-length protein to stable proteolytic products. The proteolytic products are then subjected to affinity chromatography containing the appropriated partner of interaction (96 ORF 78_or STAAU_R9 purified proteins) to determine a protein sub-region able to interact. Interacting domains are identified by mass spectrometry to determine both the intact fragment mass and the completely digested with trypsin (by in-gel digestion) to better determine the amino acid residues contained within the partial proteolytic fragment. Using both sets of data, the amino acid sequence of the partial proteolytic fragment can be precisely determined.

Another approach is based on peptide screening using different portions of 96 ORF 78 or STAAU_R9 to identify minimal peptides from each polypeptide that are able to disrupt the interaction between the two proteins. It is assumed that fragments able to prevent interaction between STAAU_R9 and 96 ORF 78 correspond to domains of interaction located on either of the two interacting proteins. The different peptide fragments can be screened as competitors of interaction in protein: protein binding assays such as the ones described below. Fine mapping of interaction site(s) within a protein can be performed by an extensive screen of small overlapping fragments or peptides spanning the entire amino acid sequence of the protein.

Suitable STAAU_R9 and 96 ORF 78-derived amino acid fragments representative of the complete sequence of both proteins can be obtained by chemical synthesis. For instance, in the multipin approach, peptides are simultaneously synthesized by the assembly of small quantities of peptides (ca. 50 nmol) on plastic pins derivatized with an ester linker based on glycolate and 4-(hydroxymethyl) benzoate [Maeji 1991 Pept Res, 4:142-6].

*S. aureus* STAAU_R9 Polypeptides

In one aspect of the invention there are provided polypeptides of *S. aureus* referred to herein as "STAAU_R9" and "STAAU_R9 polypeptides" as well as biologically, diagnostically, prophylactically, clinically or therapeutically useful variants thereof, and compositions comprising the same.

Among the particularly preferred embodiments of the invention are variants of *S. aureus* STAAU_R9 polypeptides encoded by naturally occurring alleles of the STAAU_R9 gene. The present invention provides for an isolated polypeptide which comprises or consists of: (a) an amino acid sequence which has at least 40% identity, preferably at least 50% identity, preferably at least 80% identity, more preferably at least 90%, yet more preferably at least 95%, most preferably at least 97-99%, or exact identity, over the entire length of SEQ ID NO: 2; or b) an amino acid sequence that has at least 60% similarity, at least 70% similarity, at least 80% similarity, at least 90% similarity, at least 95% similarity, at least 97-99% similarity or even 100% similarity over the entire length of SEQ ID NO: 2.

The present invention provides for an isolated polypeptide which comprises or consists of: (a) an amino acid sequence which has at least 35% identity, preferably at least 40% identity, preferably at least 50% identity, more preferably at least 60%, more preferably at least 80%, yet more preferably at least 95%, most preferably at least 97-99%, or exact identity, over the entire length of SEQ ID NO: 6; or b) an amino acid sequence that has at least 60% similarity, at least 70% similarity, at least 80% similarity, at least 90% similarity, at least 95% similarity, at least 97-99% similarity or even 100% similarity over the entire length of SEQ ID NO: 6.

The polypeptides of the invention include a polypeptide of FIG. 1 (SEQ ID NO: 2) (in particular the mature polypeptide) as well as polypeptides and fragments, particularly those which have a biological activity of STAAU_R9, and also those which have at least 40% identity over 50 or more amino acids to a polypeptide of SEQ ID NO: 2 or the relevant portion, preferably at least 50%, 60%, 70%, or 80% identity over 50 or more amino acids to a polypeptide of SEQ ID NO: 2, more preferably at least 90% identity over 50 or more amino acids to a polypeptide of SEQ ID NO: 2 and still more preferably at least 95% identity over 50 or more amino acids to a polypeptide of SEQ ID NO: 2 and yet still more preferably at least 99% identity or exact identity over 50 or more amino acids to a polypeptide of SEQ ID NO: 2.

The polypeptides of the invention also include a polypeptide or protein fragment that has at least 60%, 70%, 80%, 90%, 95%, or even 97-99% similarity over 50 or more contiguous amino acids to a polypeptide of SEQ ID NO: 2.

It is most preferred that a polypeptide of the invention is derived from *S. aureus*, however, it may be obtained from other organisms of the same taxonomic genus. A polypeptide of the invention may also be obtained, for example, from organisms of the same taxonomic family or order.

Fragments of STAAU_R9 also are included in the invention. These fragments may include, for example, truncation polypeptides having a portion of an amino acid sequence of FIG. 1 (SEQ ID NO: 2), a fragment or a variant thereof, such as a continuous series of residues that includes an amino- and/or carboxyl-terminal amino acid sequence. Degradation forms of the polypeptides of the invention produced by or in a host cell, particularly *S. aureus*, are also preferred. Further preferred are fragments characterized by structural or functional attributes such as fragments that comprise alpha-helix and alpha-helix-forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Fragments of STAAU_R9 may be expressed as fusion proteins with other proteins or protein fragments.

Preferred fragments also include an isolated polypeptide comprising an amino acid sequence having at least 10, 15, 20, 30, 39, 50, 100, or 200 or more contiguous amino acids from the amino acid sequence of SEQ ID NO: 2, or comprising an amino acid sequence having at least 10, 15, 20, 25 or more contiguous amino acids from the amino acid sequence of SEQ ID NO: 6, wherein such preferred fragments retain at least one biological activity of a STAAU_R9 polypeptide. Preferably the fragment retains specific interaction (e.g., binding) to 96 ORF 78 or a specific binding fragment thereof. In preferred embodiments the polypeptide is a fragment of full-length STAAU_R9 polypeptide (or variant thereof that includes the sequence of SEQ ID NO. 6 (or a variant). Preferably the fragment includes up to 50%, 40%, 30%, 20%, 10%, or 5% of the full-length sequence. Such fragments include for example, fragments in which 50% or more, 60% or more, 70% or more, 80% or more, or 90% or more of the amino acids from the N-terminal end of the full-length polypeptide are deleted. Additional embodiments include fragments of SEQ ID NO. 6, e.g., fragments represented by deleting 1, 2, 3, 4, or 5 amino acids from one or both ends of SEQ ID NO. 6, but highly preferably the fragment retains specific interaction (e.g., binding) to 96 ORF 78.

Also preferred are biologically "active" fragments which are those fragments that mediate activities of *S. aureus* STAAU_R9, including those with a similar activity or an improved activity, or with a decreased undesirable activity. Also included are those fragments that are antigenic or immunogenic in an animal, especially in a human. Particularly preferred are fragments comprising domains that confer a function essential for viability of *S. aureus*.

Fragments of the polypeptides of the invention may be employed for producing the corresponding full-length polypeptide by peptide synthesis; therefore, these variants may be employed as intermediates for producing the full-length polypeptides of the invention.

*S. aureus* Polynucleotides

The invention likewise provides polynucleotides that encode STAAU_R9 polypeptides, particularly polynucleotides that encode the polypeptide herein designated *S. aureus* STAAU_R9, or other STAAU_R9 polypeptides described herein.

In one aspect of the invention, a polynucleotide, highly preferably isolated, enriched, or purified, is provided that comprises a region encoding a *S. aureus* STAAU_R9 polypeptide, the polynucleotide comprising a sequence set out in SEQ ID NO: 1. Such a polynucleotide encodes a full length STAAU_R9 gene, a fragment or a variant thereof (e.g. SEQ ID NO: 6). It is contemplated that this full-length gene is essential to the growth and/or survival of an organism which possesses it, such as *S. aureus*.

As a further aspect of the invention there are provided isolated nucleic acid molecules encoding and/or expressing a fragment of a full-length STAAU_R9 polypeptide, particularly a *S. aureus* STAAU_R9 polypeptide, a fragment or a variant thereof (e.g. SEQ ID NO: 6). Further embodiments of the invention include biologically, diagnostically, prophylactically, clinically or therapeutically useful polynucleotides, polypeptides, variants thereof, and compositions comprising same.

A polynucleotide of the invention can be obtained using *S. aureus* cells as starting material, the nucleotide sequence information disclosed in SEQ ID NO: 1, and standard cloning and screening methods, such as those for cloning and sequencing chromosomal DNA fragments from bacteria. For example, to obtain a polynucleotide sequence of the invention, such as the polynucleotide sequence disclosed as in SEQ ID NO: 1, a library of clones of chromosomal DNA of *S. aureus* in *E. coli* or another suitable host is probed with a radiolabeled oligonucleotide, preferably a 17-mer or longer, derived from a partial sequence. Clones carrying DNA identical to that of the probe can be distinguished using stringent hybridization conditions. As herein used, the terms "stringent conditions" and "stringent hybridization conditions" mean hybridization occurring only if there is at least 95% and preferably at least 97% identity between the sequences. A specific example of stringent hybridization conditions is of an overnight incubation of a hybridization support (e.g., a nylon or nitrocellulose membrane) at 42° C. in a solution comprising: $1 \times 10^6$ cpm/ml labeled probe, 50% formamide, 5×SSC (150 mM NaCl, 15 mM trisodium citrate), 50 mM sodium phosphate (pH 7.6), 5×Denhardt's solution, 10% dextran sulfate, and 20 micrograms/ml of denatured, sheared salmon sperm DNA, followed by washing the hybridization support in 0.1×SSC at 65° C. Hybridization and wash conditions are well known to those skilled in the art and are exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention. By sequencing the individual clones thus identified by hybridization, it is possible to confirm the identity of the clone.

Alternatively, an amplification process can be utilized to isolate the polynucleotide. In this approach, the sequence disclosed as SEQ ID NO: 1 is targeted by two oligonucleotides, one identical to a sequence on the coding DNA strand at or upstream of the ATG initiation codon and the other which anneals to the opposite strand at or downstream of the stop codon. Priming from these oligonucleotides in a polymerase chain reaction (PCR) yields a full-length gene coding sequence. Such suitable techniques are described by Sambrook et al., Molecular Cloning: A Laboratory Manual, $2^{nd}$ Edition, Cold Spring Harbor Laboratory Press, Cold Spring Harbor, N.Y. (1989). Many variations of the basic technique are well-known to those familiar with PCR.

In a further aspect, the present invention provides for an isolated polynucleotide comprising, consisting essentially of, or consisting of: (a) a polynucleotide sequence which has at least 60% identity, preferably at least 70% identity, more preferably at least 80% identity, more preferably at least 90% identity, yet more preferably at least 95%, most preferably at least 97-99%, or exact identity, to that of SEQ ID NO: 1; (b) a polynucleotide sequence encoding a polypeptide which has at least 40% identity, preferably at least 50% identity, preferably at least 60% identity, more preferably at least 70% identity, more preferably at least 80% identity, more preferably at least 90%, yet more preferably at least 95%, most preferably at least 97-99% or exact identity to SEQ ID NO: 2 over the entire length of SEQ ID NO: 2; or the complement of a sequence of (a) or (b) above.

In another embodiment, the present invention provides for an isolated polynucleotide comprising or consisting of: (a) a polynucleotide sequence which has at least 60% identity, preferably at least 70% identity, more preferably at least 80% identity, more preferably at least 90% identity, yet more preferably at least 95%, most preferably at least 97-99% or exact identity, to that of SEQ ID NO: 5; (b) a polynucleotide sequence encoding a polypeptide which has at least 35% identity, preferably at least 40% identity, preferably at least 50% identity, preferably at least 60% identity, more preferably at least 70% identity, more preferably at least 80% identity, more preferably at least 90%, yet more preferably at least 95%, most preferably at least 97-99% or exact identity to SEQ ID NO: 6; or the complement of a sequence of (a) or (b).

The invention provides a polynucleotide sequence identical over its entire length to the coding sequence of SEQ ID NO: 1. Also provided by the invention is a coding sequence for a mature polypeptide or a fragment thereof by itself as well as a coding sequence for a mature polypeptide or a fragment in reading frame with another coding sequence, such as a sequence encoding a leader or secretory sequence, a pre-, or pro-, or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize or destabilize mRNAs, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., Proc. Natl. Acad. Sci. 86: 821-824 (1989), or an HA peptide tag [Wilson et al., Cell 37: 767 (1984)], both of which may be useful in purifying polypeptide sequences fused to them. Polynucleotides of the invention also include, but are not limited to, polynucleotides comprising a structural gene and its naturally associated sequences that control gene expression.

While it is most preferred that a polynucleotide of the invention be derived from *S. aureus*, it may also be obtained from other organisms of the same taxonomic genus. A polynucleotide of the invention may also be obtained, for example, from organisms of the same taxonomic family or order.

Further preferred embodiments are polynucleotides encoding *S. aureus* STAAU_R9 variants that have the amino acid sequence of *S. aureus* STAAU_R9 polypeptide of SEQ ID NO: 2 in which several, a few, 5 to 10, 1 to 5, 1 to 3, 2, 1 or no amino acid residues are substituted, modified, deleted and/or added, in any combination. Further preferred embodiments are polynucleotides encoding *S. aureus* STAAU_R9 variants that have the amino acid sequence of *S. aureus* STAAU_R9 polypeptide of SEQ ID NO: 6 in which several, a few, 5 to 10, 1 to 5, 1 to 3, 2, 1 or no amino acid residues are substituted, modified, deleted and/or added, in any combination. Especially preferred among these polynucleotides are those encoding silent nucleotide alterations that do not alter the coding sequence or activities of *S. aureus* STAAU_R9 polypeptides they encode.

In another preferred embodiment, the polynucleotide encodes a STAAU_R9 polypeptide having the sequence set forth in SEQ ID NO:6 and in which several, a few, 5 to 10, 1 to 5, 1 to 3, 2 or 1 amino acid residues are substituted, modified, deleted and/or added, in any combination, in the sequence or sequences surrounding the sequence encoding SEQ ID NO:6.

Preferred embodiments are polynucleotides encoding polypeptides that retain substantially the same biological function or activity as the mature polypeptide encoded by a DNA of SEQ ID NO: 1.

In accordance with certain preferred embodiments of this invention there are provided polynucleotides that hybridize, particularly under stringent conditions, to *S. aureus* STAAU_R9 polynucleotide sequences, such as those polynucleotides in FIG. 1.

The polynucleotides of the invention are useful as hybridization probes for RNA, cDNA and genomic DNA to isolate full-length cDNAs and genomic clones encoding genes that have a high degree of sequence identity to the STAAU_R9 gene. Such probes generally will comprise at least 15 to about 100 residues or base pairs, although such probes will preferably have about 20 to 50 nucleotide residues or base pairs. Particularly preferred probes are about 20 to about 30 nucleotide residues or base pairs in length.

A coding region of a related STAAU_R9 gene from a bacterial species other than *S. aureus* may be isolated by screening a library using a DNA sequence provided in SEQ ID NO: 1 to synthesize an oligonucleotide probe. A labeled oligonucleotide having a sequence complementary to that of a gene of the invention is then used to screen a library of cDNA, genomic DNA or mRNA to determine to which member(s) of the library the probe hybridizes.

There are several methods available and well known to those skilled in the art to obtain full-length DNAs, or extend short DNAs, for example those based on the method of Rapid Amplification of cDNA Ends (RACE) [see, for example, Frohman, et al., Proc. Natl. Acad. Sci. USA 85:8998-9002, 1988]. Recent modifications of the technique, exemplified by the MARATHON™ technology (Clontech Laboratories Inc.) for example, have significantly simplified the search for longer cDNAs. In the MARATHON technology, cDNAs are prepared from mRNA extracted from a chosen cell and an 'adaptor' sequence is ligated onto each end. Nucleic acid amplification by PCR is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor-specific primer that anneals further 3' in the adaptor sequence and a gene-specific primer that anneals further 5' in the selected gene sequence). The products of this reaction can then be analyzed by DNA sequencing and a full-length DNA constructed either by joining the product directly to the existing DNA to give a complete sequence, or by carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as further discussed herein relating to polynucleotide assays.

The polynucleotides of the invention that are oligonucleotides derived from a sequence of SEQ ID NO:1 are useful for the design of PCR primers in reactions to determine whether or not the polynucleotides identified herein in whole or in part are transcribed in bacteria in infected tissue. That is, the polynucleotides of the invention are useful for diagnosis of infection with a bacterial strain carrying those sequences. It is recognized that such sequences also have utility in diagnosis of the stage of infection and type of infection the pathogen has attained.

The invention also provides polynucleotides that encode a polypeptide that is the mature protein plus additional amino or carboxyl-terminal amino acids, or amino acids interior to the mature polypeptide. Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

A polynucleotide of the invention thus may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

In addition to the standard A, G, C, T/U representations for nucleotides, the term "N" may also be used in describing certain polynucleotides of the invention. "N" means that any of the four DNA or RNA nucleotides may appear at such a designated position in the DNA or RNA sequence, except it is preferred that N is not a nucleotide that when taken in combination with adjacent nucleotide positions, read in the correct reading frame, would have the effect of generating a premature termination codon in such reading frame.

For each and every polynucleotide of the invention there is also provided a polynucleotide complementary to it.

Vectors, Host Cells, and Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention Recombinant STAAU_R9 and bacteriophage polypeptides of the present invention may be prepared by processes well known to those skilled in the art from genetically engineered host cells comprising expression systems. Accordingly, in a further aspect, the present invention relates to expression systems that comprise a STAAU_R9 or bacteriophage polynucleotide or polynucleotides of the present invention, to host cells which are genetically engineered with such expression systems, and to the production of polypeptides of the invention by recombinant techniques.

For recombinant production of a STAAU_R9 polypeptide of the invention, host cells can be genetically engineered to incorporate expression systems or portions thereof or polynucleotides of the invention. Representative examples of appropriate hosts include bacterial cells (Gram positive and Gram negative), fungal cells, insect cells, animal cells and plant cells. Polynucleotides are introduced to bacteria by standard chemical treatment protocols, such as the induction of competence to take up DNA by treatment with calcium chloride (Sambrook et al., supra). Introduction of polynucleotides into fungal (e.g., yeast) host cells is effected, if desired, by standard chemical methods, such as lithium acetate—mediated transformation.

A great variety of expression systems are useful to produce polypeptides of the invention. Such vectors include among others, chromosomal-, episomal- and virus-derived vectors. For example, vectors derived from bacterial plasmids, from bacteriophages, from transposons, from yeast episomes, from insertion elements, from yeast chromosomal elements, from viruses, and from vectors derived from combinations thereof, are useful in the invention.

Polypeptides of the invention are recovered and purified from recombinant cell cultures by well-known methods including ammonium sulfate or ethanol precipitation, acid or urea extraction, anion or cation exchange chromatography, phosphocellulose chromatography, hydrophobic interaction chromatography, affinity chromatography, hydroxylapatite chromatography, and lectin chromatography. Well known techniques for refolding may be employed to regenerate an active conformation when the polypeptide is denatured during isolation and/or purification.

Diagnostic, Prognostic, Serotyping, and Mutation Assays

This invention is also related to the use of STAAU_R9 polynucleotides and polypeptides of the invention for use as diagnostic reagents. Detection of S. aureus STAAU_R9 polynucleotides and/or polypeptides in a eukaryote, particularly a mammal, and especially a human, will provide a diagnostic method for diagnosis of disease, staging of disease or response of an infectious organism to drugs. Eukaryotes, particularly mammals, and especially humans, particularly those infected or suspected to be infected with an organism comprising the S. aureus STAAU_R9 gene or protein, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species.

Point mutations can be identified by hybridizing amplified DNA to labeled STAAU_R9 polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al, (1985) Science 230, 1242. Sequence changes at specific locations also may be revealed by nuclease protection assays, such as RNase, V1 and S1 protection assay or a chemical cleavage method. See, for example, Cotton et al., (1985) Proc. Natl. Acad. Sci., USA 85, 4397-4401.

In another embodiment, an array of oligonucleotide probes comprising STAAU_R9 nucleotide sequence or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., (1996) Science 274, 610).

Thus in another aspect, the present invention relates to a diagnostic kit which comprises: (a) a polynucleotide of the present invention, preferably the nucleotide sequence of SEQ ID NO: 1, or a fragment thereof (e.g. SEQ ID NO: 5); (b) a nucleotide sequence complementary to that of (a); (c) a polypeptide of the present invention, preferably the polypeptide of SEQ ID NO: 2 or a fragment thereof (e.g. SEQ ID NO: 6); or (d) an antibody to a polypeptide of the present invention, preferably to the polypeptide of SEQ ID NO: 2 or fragment thereof (e.g. SEQ ID NO: 6).

It will be appreciated that in any such kit, (a), (b), (c) or (d) may comprise a substantial component. Such a kit will be of use in diagnosing a disease or susceptibility to a disease, among others.

This invention also relates to the use of STAAU_R9 polynucleotides of the present invention as diagnostic reagents. Detection of a mutated form of a polynucleotide of the invention, preferably, SEQ ID NO: 1, which is associated with a disease or pathogenicity will provide a diagnostic tool that can add to, or define, a diagnosis of a disease, a prognosis of a course of disease, a determination of a stage of disease, or a susceptibility to a disease, which results from under-expression, over-expression or altered expression of the polynucleotide. Organisms, particularly infectious organisms, carrying mutations in such polynucleotide may be detected at the polynucleotide level by a variety of techniques, such as those described elsewhere herein.

The STAAU_R9 nucleotide sequences of the present invention are also valuable for organism chromosome identification. The sequence is specifically targeted to, and can hybridize with, a particular location on an organism's chromosome, particularly to a *S. aureus* chromosome. The mapping of relevant sequences to chromosomes according to the present invention may be an important step in correlating those sequences with pathogenic potential and/or an ecological niche of an organism and/or drug resistance of an organism, as well as the essentiality of the gene to the organism. Once a sequence has been mapped to a precise chromosomal location, the physical position of the sequence on the chromosome can be correlated with genetic map data. Such data may be found on-line in a sequence database. The relationship between genes and diseases that have been mapped to the same chromosomal region are then identified through known genetic methods, for example, through linkage analysis (coinheritance of physically adjacent genes) or mating studies, such as by conjugation.

The differences in a polynucleotide and/or polypeptide sequence between organisms possessing a first phenotype and organisms possessing a different, second different phenotype can also be determined. If a mutation is observed in some or all organisms possessing the first phenotype but not in any organisms possessing the second phenotype, then the mutation is likely to be the causative agent of the first phenotype.

Polypeptides and polynucleotides for prognosis, diagnosis or other analysis may be obtained from a putatively infected and/or infected individual's bodily materials. Particularly DNA or polynucleotides, from any of these sources may be used directly for detection or may be amplified enzymatically using PCR or other amplification technique with oligonucleotide amplification primers derived from the polynucleotide sequence of *S. aureus* STAAU_R9. RNA, particularly mRNA, or RNA reverse transcribed to cDNA, is also useful for diagnostics. Following amplification of a *S. aureus* STAAU_R9related polynucleotide from a sample, characterization of the species and strain of infecting or resident organism is made by an analysis of the amplified polynucleotide relative to one or more reference polynucleotides or sequences relative to a standard from a related organism (i.e. a known strain of *S. aureus*).

The invention further provides a process for diagnosing bacterial infections such as those caused by *S. aureus*, the process comprising determining from a sample derived from an individual, such as a bodily material, an increased level of expression of a polynucleotide having a sequence disclosed in SEQ ID NO: 1 relative to a sample taken from a non-diseased individual. Increased or decreased expression of a STAAU_R9 polynucleotide can be measured using any one of the methods well known in the art for the quantitation of polynucleotides, such as, for example, PCR, RT-PCR, RNase protection, Northern blotting and other hybridization methods, and spectrometry.

In addition, a diagnostic assay in accordance with the invention for detecting over-expression of STAAU_R9 polypeptide compared to normal control tissue samples may be used to detect the presence of an infection, for example. Assay techniques that can be used to determine levels of a *S. aureus* STAAU_R9 polypeptide, in a sample derived from a host, such as a bodily material, are well-known to those of skill in the art. Such assay methods include radioimmunoassays, competitive-binding assays, Western Blot analysis, antibody sandwich assays, antibody detection and ELISA assays.

Gridding and Polynucleotide Subtraction of *S. aureus* Genomic Sequences

The STMU_R9 polynucleotides of the invention may be used as components of polynucleotide arrays, preferably high density arrays or grids. These high density arrays are particularly useful for diagnostic and prognostic purposes. For example, a set of spots each comprising a different gene, and further comprising a polynucleotide or polynucleotides of the invention, may be used for probing, such as hybridization or nucleic acid amplification, using a probe obtained or derived from a bodily sample, to determine the presence a particular polynucleotide sequence or related sequence in an individual.

Antibodies Specific for *S. aureus* Peptides or Polypeptides

The STAAU_R9 polypeptides and polynucleotides of the invention or variants thereof, or cells expressing them are useful as immunogens to produce antibodies immunospecific for such polypeptides or polynucleotides, respectively.

In certain preferred embodiments of the invention there are provided antibodies against *S. aureus* STAAU_R9 polypeptides or polynucleotides encoding them. Antibodies against STAAU_R9-polypeptide or STAAU_R9-polynucleotide are useful for treatment of infections, particularly bacterial infections.

Antibodies generated against the polypeptides or polynucleotides of the invention are obtained by administering the polypeptides and/or polynucleotides of the invention or epitope-bearing fragments of either or both, analogues of either or both, or cells expressing either or both, to an animal, preferably a nonhuman, using routine protocols. For preparation of monoclonal antibodies, any technique known in the art that provides antibodies produced by continuous cell line cultures is useful. Examples include various techniques, such as those in Kohler, G. and Milstein, C., Nature 256: 495-497 (1975); Kozbor et al., Immunology Today 4: 72 (1983); and Cole et al., pg. 96-96 in Monoclonal Anbitodies and Cancer Therapy, Alan R. Liss, Inc. (1985).

Techniques for the production of single chain antibodies (U.S. Pat. No. 4,946,968) can be adapted to produce single chain antibodies to polypeptides or polynucleotides of this invention. Also, transgenic mice, or other mammals, are useful to express humanized antibodies immunospecific to the polypeptides or polynucleotides of the invention.

When antibodies are administered therapeutically, the antibody or variant thereof is preferably modified to make it less immunogenic in the individual. For example, if the individual is human the antibody is most preferably "humanized," where the complementarity determining region or regions of the hybridoma-derived antibody has been transplanted into a human monoclonal antibody, for example as described in Jones et al. (1986), Nature 321, 522-525 or Tempest et al., (1991) Biotechnology 9, 266-273.

Alternatively, phage display technology is useful to select antibody genes with binding activities towards a STMU_R9 polypeptide of the invention. In one possible scheme, antibody fragments specific for S. aureus STAAU_R9 are selected from an immune library of antibody genes expressed as fusions with coat protein of filamentous phage. Alternatively, naive libraries are screened by phage display techniques to identify genes encoding antibodies specified for STAAU_R9 or from naive libraries [McCafferty, et al., (1990), Nature 348, 552-554; Marks, et al., (1992) Biotechnology 10, 969-783; a recent reference is de Haard et al. (1999) J. Biol. Chem. 274: 18218-18230]. The ability to recover, for various targets, antibodies with subnanomolar affinities obviates the need for immunization. The affinity of these antibodies can also be improved by, for example, chain shuffling [Clackson et al., (1991) Nature 352: 628].

The above-described antibodies may be employed to isolate or to identify clones expressing the polypeptides or polynucleotides of the invention, for example to purify the polypeptides or polynucleotides by immunoaffinity chromatography.

A variant polypeptide or polynucleotide of the invention, such as an antigenically or immunologically equivalent derivative or a fusion protein of the polypeptide is also useful as an antigen to immunize a mouse or other animal such as a rat or chicken. A fused protein provides stability to the polypeptide acting as a carrier, or acts as an adjuvant or both. Alternatively, the antigen is associated, for example by conjugation, with an immunogenic carrier protein, such as bovine serum albumin, keyhole limpet haemocyanin or tetanus toxoid. Alternatively, when antibodies are to be administered therapeutically, alternatively a multiple antigenic polypeptide comprising multiple copies of the polypeptide, or an antigenically or immunologically equivalent polypeptide thereof may be sufficiently antigenic to improve immunogenicity so as to obviate the use of a carrier.

In accordance with an aspect of the invention, there is provided the use of a STAAU_R9 polynucleotide of the invention for therapeutic or prophylactic purposes, in particular genetic immunization. The use of a STAAU_R9 polynucleotide of the invention in genetic immunization preferably employs a suitable delivery method such as direct injection of plasmid DNA into muscles [Wolff et al., Hum Mol Genet (1992) 1: 363, Manthorpe et al., Hum. Gene Ther. (1983) 4: 419], delivery of DNA complexed with specific protein carriers [Wu et at., JBiol Chem. (1989) 264: 16985], coprecipitation of DNA with calcium phosphate [Benvenisty and Reshef, Proc. Natl. Acad. Sci. USA, (1986) 83: 9551], encapsulation of DNA in various forms of liposomes [Kaneda et al., Science (1989) 243: 375], particle bombardment [Tang et al., Nature (1992) 356:152, Eisenbraun et al., DNA Cell Biol (1993) 12: 791] or in vivo infection using cloned retroviral vectors [Seeger et al., Proc. Natl, Acad. Sci. USA (1984) 81: 5849].

Antagonists and Agonists: Assays and Molecules

The invention is based in part on the discovery that STAAU_R9 is a target for the bacteriophage 96 ORF 78 inhibitory factor. The inventors have recognized the utility of the interaction in the development of antibacterial agents. Specifically, the inventors have recognized that 1) STAAU_R9 is a critical target for bacterial inhibition; 2) 96 ORF 78 or derivatives or functional mimetics thereof are useful for inhibiting bacterial growth; and 3) the interaction between STAAU_R9 or fragment thereof (e.g. SEQ ID NO: 6) of S. aureus and 96 ORF 78 may be used as a target for the screening and rational design of drugs or antibacterial agents. In addition to methods of directly inhibiting STAAU_R9 activity, methods of inhibiting STAAU_R9 expression are also attractive for antibacterial activity.

In several embodiments of the invention, there are provided methods for identifying compounds which bind to or otherwise interact with and inhibit or activate an activity or expression of a polypeptide and/or polynucleotide of the invention comprising: contacting a polypeptide and/or polynucleotide of the invention with a compound to be screened under conditions to permit binding to or other interaction between the compound and the polypeptide and/or polynucleotide to assess the binding to or other interaction with the compound, such binding or interaction preferably being associated with a second component capable of providing a detectable signal in response to the binding or interaction of the polypeptide and/or polynucleotide with the compound; and determining whether the compound binds to or otherwise interacts with and activates or inhibits an activity or expression of the polypeptide and/or polynucleotide by detecting the presence or absence of a signal generated from the binding or interaction of the compound with the polypeptide and/or polynucleotide.

Potential antagonists include, among others, small organic molecules, peptides, polypeptides and antibodies that bind to a polynucleotide and/or polypeptide of the invention and thereby inhibit or extinguish its activity or expression. Potential antagonists also may be small organic molecules, a peptide, a polypeptide such as a closely related protein or antibody that binds the same sites on a binding molecule, such as a binding molecule, without inducing STAAU_R9-induced activities, thereby preventing the action or expression of S. aureus STAAU_R9 polypeptides and/or polynucleotides by excluding S. aureus STAAU_R9 polypeptides and/or polynucleotides from binding.

Potential antagonists also include a small molecule that binds to and occupies the binding site of the polypeptide thereby preventing binding to cellular binding molecules, such that normal biological activity is prevented. Cellular binding molecules include but are not limited to proteins involved in DNA replication. Examples of cellular binding molecules include DNA helicase, DNA Pol III, and SSB.

Examples of small molecules include but are not limited to small organic molecules, peptides or peptide-like molecules. Other potential antagonists include antisense molecules [see Okano, (1991) J. Neurochem. 56, 560; see also Oligodeoxynucleotides As Antisense Inhibitors of Gene Expression, CRC Press, Boca Raton, Fla. (1988), for a description of these molecules]. Preferred potential antagonists include compounds related to and variants of 96 ORF 78 and of STAAU_R9. Other examples of potential polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

Compounds may be identified from a variety of sources, for example, cells, cell-free preparations, chemical libraries, and natural product mixtures. These substrates and ligands may be natural substrates and ligands or may be structural or functional mimetics. See, e.g., Coligan et al., Current Protocols in Immunology 1(2): Chapter 5 (1991). Peptide modulators can also be selected by screening large random libraries of all possible peptides of a certain length.

Compounds derived from the polypeptide sequence of 96 ORF 78 could represent fragments representing small overlapping peptides spanning the entire amino acid sequence of these ORFs. Fragments of 96 ORF 78 can be produced as described above.

Certain of the polypeptides of the invention are biomimetics, functional mimetics of the natural S. aureus STAAU_R9 polypeptide. These functional mimetics are useful for, among other things, antagonizing the activity of S. aureus STAAU_R9 polypeptide or as an antigen or immunogen in a manner described above. Functional mimetics of the polypeptides of the invention include but are not limited to truncated polypeptides. For example, preferred functional mimetics include a polypeptide comprising the polypeptide sequence set forth in SEQ ID NO: 6 lacking 5, 8, 10, 15, 20, 25amino- or carboxy-terminal amino acid residues, including fusion proteins comprising one or more of these truncated sequences. Polynucleotides encoding each of these functional mimetics may be used as expression cassettes to express each mimetic polypeptide. It is preferred that these cassettes comprise 5' and 3' restriction sites to allow for a convenient means to ligate the cassettes together when desired. It is further preferred that these cassettes comprise gene expression signals known in the art or described elsewhere herein.

Screening Assays According to the Invention

It is desirable to devise screening methods to identify compounds which stimulate or which inhibit the function of the STAAU_R9 polypeptide or polynucleotide of the invention. Accordingly, the present invention provides for a method of screening compounds to identify those that modulate the function of a polypeptide or polynucleotide of the invention. In general, antagonists may be employed for therapeutic and prophylactic purposes. It is contemplated that an agonist of STAAU_R9 may be useful, for example, to enhance the growth rate of bacteria in a sample being cultured for diagnostic or other purposes.

It has been determined that STAAU_R9 is a target for bacteriophage 96 ORF 78 product, which acts as an inhibitory factor. Applicants have recognized the utility of the interaction in the development of antibacterial agents. Polypeptide and/or polynucleotide targets such as STAAU_R9 are critical targets for bacterial inhibition. S. aureus bacteriophage 96 ORF 78 or derivatives or functional mimetics thereof are useful for inhibiting bacterial growth and the interaction, binding, inhibition and/or activation which occurs between polypeptides, such as for example STMU_R9 of S. aureus and 96 ORF 78 may be used for the screening and rational design of drugs or antibacterial agents. In addition to methods for directly inhibiting a target such as STAAU_R9 activity, methods of inhibiting a target such as STAAU_R9 expression are also attractive for antibacterial activity.

In preferred embodiments, the method involves the interaction of an inhibitory ORF product or fragment thereof with the corresponding bacterial target or fragment thereof that maintains the interaction with the ORF product or fragment. Interference with the interaction between the components can be monitored, and such interference is indicative of compounds that may inhibit, activate, or enhance the activity of the target molecule.

a. Binding Assays

There are a number of methods of examining binding of a candidate compound to a protein target such as STAAU_R9 and a polypeptide comprising amino acid sequence of SEQ ID NO: 2, or fragment thereof such as SEQ ID NO: 6. Screening methods that measure the binding of a candidate compound to a STAAU_R9 polypeptide or polynucleotide, or to cells or supports bearing the polypeptide or a fusion protein comprising the polypeptide, by means of a label directly or indirectly associated with the candidate compound, are useful in the invention.

The screening method may involve competition for binding of a labeled competitor such as 96 ORF 78 or a fragment that is competent to bind STAAU_R9 or fragment thereof.

Non-limiting examples of screening assays suitable for use in accordance with the present invention include the following [Reviewed in Sittampalam et al. 1997 Curr. Opin. Chem. Biol. 3:384-91]:

i.) Time-Resolved Fluorescence Resonance Energy Transfer (TR-FRET)

A method of measuring inhibition of binding of two proteins using fluorescence resonance energy transfer [FRET; de Angelis, 1999, Physiological Genomics]. FRET is a quantum mechanical phenomenon that occurs between a fluorescence donor (D) and a fluorescence acceptor (A) in close proximity (usually <100 A of separation.) if the emission spectrum of D overlaps with the excitation spectrum of A. Variants of the green fluorescent protein (GFP) from the jellyfish *Aequorea victoria* are fused to a polypeptide or protein and serve as D-A pairs in a FRET scheme to measure protein-protein interaction. Cyan (CFP: D) and yellow (YFP: A) fluorescence proteins are linked with STAAU_R9 polypeptide, or a fragment thereof and a 96 ORF 78 polypeptide respectively. Under optimal proximity, interaction between the STAAU_R9 polypeptide and a 96 ORF 78 polypeptide causes a decrease in intensity of CFP fluorescence concomitant with an increase in YFP fluorescence.

The addition of a candidate modulator to the mixture of appropriately labeled STAAU_R9 and 96 ORF 78 polypeptide, will result in an inhibition of energy transfer evidenced by, for example, a decrease in YFP fluorescence at a given concentration of 96 ORF 78 relative to a sample without the candidate inhibitor.

An extension of the FRET technology, termed time-resolved FRET (TR-FRET or HTRF [homogeneous time-resolved energy transfer]) lends itself particularly well to identification of protein-protein interactions in the context of high-throughput screening. In brief, TR-FRET constitutes a homogeneous assay method based on the long-lived fluorescence of rare earth cryptates such as Europium (Eu) and amplification by nonradiative energy transfer to a suitable acceptor such as allophycocyanin (APC). The TR-FRET principle allows double discrimination of the emitted signal through temporal and spectral selectivity. Since the lifetime of fluorescence emission from APC (acceptor) contains a contribution equal to the Eu (donor) lifetime in the presence of nonradiative energy transfer, a long-lived APC acceptor signal can be resolved from its natural prompt fluorescence in the absence of energy transfer. Eu and APC are brought into proximity via a pair of interacting molecules such as polypeptides. To demonstrate interaction between the STAAU_R9 polypeptide, or a fragment thereof, and a 96 ORF 78 polypeptide, the respective polypeptide is labeled by recombinant DNA methodology to contain an N- or C-terminal tag that is recognized by a binding molecule which itself is conjugated to either Eu or APC. A variety of binding molecules may be employed, including an antibody (directed against an epitope) or streptavidin (directed against biotin). Alternatively, one or both of the interacting proteins is conjugated directly to either Eu or APC.

In one of several possible assay formats, STAAU_R9, or a fragment thereof (e.g. SEQ ID NO: 6) is expressed as a fusion with a polyhistidine tag and is recognized by an anti-polyhistidine Eu antibody conjugate; 96 ORF 78 is expressed as a fusion with glutathione-S-transferase (GST) and is detected by an anti-GST APC antibody conjugate. Under optimal proximity and in the presence of the anti-polyhistidine and anti-GST antibody conjugates, interaction between STAAU_R9, or a fragment thereof (e.g. SEQ ID NO: 6), and 96 ORF 78 induces nonradiative, time-resolved energy transfer from Eu to APC, detected optimally at 665 nm.

The addition of a candidate modulator (i.e., a test compound) to the mixture of appropriately labeled STAAU_R9 and 96 ORF 78 polypeptide, will result in an inhibition of energy transfer evidenced by, for example, a decrease in APC fluorescence at a given concentration of 96 ORF 78 relative to a sample without the candidate inhibitor.

ii.) Fluorescence Polarization

Fluorescence polarization measurement is another useful method to quantitate protein-protein binding. The fluorescence polarization value for a fluorescently-tagged molecule depends on the rotational correlation time or tumbling rate. Protein complexes, such as those formed by a *S. aureus* STAAU_R9 polypeptide, or a fragment thereof associating with a fluorescently labeled polypeptide (e.g., 96 ORF 78 or a binding fragment thereof), have higher polarization values than does the fluorescently labeled polypeptide. Inclusion of a candidate inhibitor of the STAAU_R9 interaction results in a decrease in fluorescence polarization relative to a mixture without the candidate inhibitor if the candidate inhibitor disrupts or inhibits the interaction of STAAU_R9 with its polypeptide binding partner. It is preferred that this method be used to characterize small molecules that disrupt the formation of polypeptide or protein complexes.

iii.) Surface Plasmon Resonance

Another powerful assay to screen for inhibitors of a protein: protein interaction is surface plasmon resonance. Surface plasmon resonance is a quantitative method that measures binding between two (or more) molecules by the change in mass near a sensor surface caused by the binding of one protein or other biomolecule from the aqueous phase (analyte) to a second protein or biomolecule immobilized on the sensor(ligand). This change in mass is measured as resonance units versus time after injection or removal of the second protein or biomolecule (analyte) and is measured using a Biacore Biosensor (Biacore AB) or similar device. STAAU_R9, or a polypeptide comprising a fragment of STAAU_R9 (e.g. SEQ ID NO: 6), could be immobilized as a ligand on a sensor chip (for example, research grade CM5 chip; Biacore AB) using a covalent linkage method (e.g. amine coupling in 10 mM sodium acetate [pH 4.5]). A blank surface is prepared by activating and inactivating a sensor chip without protein immobilization. Alternatively, a ligand surface can be prepared by noncovalent capture of ligand on the surface of the sensor chip by means of a peptide affinity tag, an antibody, or biotinylation. The binding of 96 ORF 78 to STAAU_R9, or a fragment thereof, is measured by injecting purified 96 ORF 78 over the ligand chip surface. Measurements are performed at any desired temperature between 4° C. and 37° C. Conditions used for the assay (i.e., those permitting binding) are as follows: 25 mM HEPES-KOH (pH 7.6), 150 mM sodium chloride, 15% glycerol, 1 mM dithiothreitol, and 0.001% Tween 20 with a flow rate of 10 ul/min. Preincubation of the sensor chip with candidate inhibitors will predictably decrease the interaction between 96 ORF 78 and STAAU_R9. A decrease in 96 ORF 78 binding, detected as a reduced response on sensorgrams and measured in resonance units, is indicative of competitive binding by the candidate compound.

iv.) Scintillation Proximity Assay

A scintillation proximity assay (SPA) may be used to characterize the interaction between a *S. aureus* STAAU_R9 polypeptide, or a fragment thereof, for example comprising the amino acid sequence of SEQ ID NO: 2, or SEQ ID NO: 6, and another polypeptide. The SPA relies in a solid-phase substrate, such as beads or the plastic of a microtitre plate, into which a scintillant has been incorporated. For the assay, the target protein, for example a *S. aureus* STAAU_R9 polypeptide, is coupled to the beads or to the surface of the plate, either covalently through activated surface chemistries or non-covalently through a peptide affinity tag, an antibody, or biotinylation. Addition of a radiolabeled binding polypeptide, for example [$^{32}$P]-radiolabeled 96 ORF 78, results in close proximity of the radioactive source molecule to the scintillant. As a consequence, the radioactive decay excites the scintillant contained within the bead or within the plastic of the plate and detectable light is emitted. Compounds that prevent the association between immobilized *S. aureus* STAAU_R9 polypeptide and radiolabeled 96 ORF 78 will diminish the scintillation signal. The SPA thus represents an example of an ideal technology with which to screen for inhibitors of the STAAU_R9-96 ORF 78 interactions because it is readily adapted to high-throughput, automated format and because of its sensitivity for detection of protein-protein interactions with $K_D$ values in the micromolar to nanomolar ranges.

v.) Bio Sensor Assay

ICS biosensors have been described by AMBRI (Australian Membrane Biotechnology Research Institute; http//www.ambri.com.au/). In this technology, the self-association of macromolecules such as STAAU_R9, or fragment thereof, and bacteriophage 96 ORF 78 or fragment thereof, is coupled to the closing of gramacidin-facilitated ion channels in suspended membrane bilayers and hence to a measurable change in the admittance (similar to impedence) of the biosensor. This approach is linear over six order of magnitude of admittance change and is ideally suited for large scale, high through-put screening of small molecule combinatorial libraries.

vi.) Phage Display

Phage display is a powerful assay to measure protein: protein interaction. In this scheme, proteins or peptides are expressed as fusions with coat proteins or tail proteins of filamentous bacteriophage. A comprehensive monograph on this subject is *Phage Display of Peptides and Proteins. A Laboratory Manual* edited by Kay et al. (1996) Academic Press. For phages in the Ff family that include M13 and fd, gene III protein and gene VIII protein are the most commonly-used partners for fusion with foreign protein or peptides. Phagemids are vectors containing origins of replication both for plasmids and for bacteriophage. Phagemids encoding fusions to the gene III or gene VIII can be rescued from their bacterial hosts with helper phage, resulting in the display of the foreign sequences on the coat or at the tip of the recombinant phage.

In one example of a simple assay, purified recombinant STAAU_R9 protein, or fragment thereof, could be immobilized in the wells of a microtitre plate and incubated with phages displaying a 96 ORF 78 sequence in fusion with the gene III protein. Washing steps are performed to remove unbound phages and bound phages are detected with monoclonal antibodies directed against phage coat protein (gene VIII protein). An enzyme-linked secondary antibody allows quantitative detection of bound fusion protein by fluorescence, chemiluminescence, or colourimetric conversion. Screening for inhibitors is performed by the incubation of the compound with the immobilized target before the addition of phages. The presence of an inhibitor will specifically reduce the signal in a dose-dependent manner relative to controls without inhibitor.

It is important to note that in assays of protein-protein interaction, it is possible that a modulator of the interaction need not necessarily interact directly with the domain(s) of the proteins that physically interact. It is also possible that a modulator will interact at a location removed from the site of protein-protein interaction and cause, for example, a conformational change in the STAAU_R9 polypeptide. Modulators (inhibitors or agonists) that act in this manner can be termed allosteric effectors and are of interest since the change they induce may modify the activity of the STAAU_R9 polypeptide.

Testing for inhibitors is performed by the incubation of the compound with the reaction mixtures. The presence of an inhibitor will specifically reduce the signal in a dose-dependent manner relative to controls without inhibitor. Compounds selected for their ability to inhibit interactions between STAAU_R9-96 ORF 78 is further tested in functional activity assays.

b. Assays of STAAU_R9 Functional Activity

Non-limiting examples of assays to assess the functional enzymatic activity of STAAU_R9, or fragments thereof (e.g. SEQ ID NO: 6), variant or homolog thereof, include the measurement of stimulation of DNA replication. There are a number of well-known methods of measuring the DNA synthesis stimulation of a polypeptide comprising the amino acid sequence of STAAU_R9.

In vivo assay for DNA Replication, Plasmid Replication

One example of an assay for STAAU_R9 activity could involved the measurement of radiolabeled nucleotide incorporated into cellular DNA. Samples (0.5 ml) are withdrawn from cultures at appropriate time intervals and mixed with 4.5 µl of labeling solution (0.2 µCi/ml of $^3$H-thymidine [73 Ci/mmol, NEN Life Science Products, Inc.] and 70 pmol of unlabeled thymidine). After 15 minutes of reaction, incorporation is stopped by adding 5 µl of 0.2% NaN$_3$ and 5 µl of 30 µg/ml unlabeled thymidine. Samples are precipitated with 10% (w/v) trichloroacetic acid and filtered through glass fiber filters (GF-C, Whatman). The results are expressed as $^3$H-thymidine counts incorporated, normalized to the OD of the culture. Cultures of *S. aureus* are grown in the presence of varying concentrations of a candidate compound added directly to the medium. For compounds that correspond to polypeptides, the nucleotide sequence encoding the polypeptides can be cloned into a *S. aureus* expression vector containing an inducible promoter. The expression of the polypeptide can be induced following transfection of cells. In one assay, a plasmid containing a candidate inhibitor polypeptide (e.g. 96 ORF 78 or fragment or variant thereof) coding sequence under an inducible promoter is introduced into a *S aureus*. At least a 10-fold reduction in $^3$H-thymidine incorporation in the presence of 96 ORF 78 or other inhibitor indicates a reduction in STAAU_R9 activity.

The plasmid pC194 replicates in *S. aureus* by rolling circle mechanism. The single stranded origin, sso of the pC194 is involved in the synthesis of the lagging DNA strand. The plasmid pADG6406 is a derivative of pC194 lacking sso. The absence of sso leads the accumulation of plasmid single-stranded DNA. The single-stranded (ss) initiation site, ssiA, is located on the lagging strand of pAMβ1 and is a site for primosome assembly. ssiA was inserted into plasmid pADG6404. *S. aureus* harboring plasmids are grown to mid-log phase and their total DNA is extracted and analyzed by Southern hybridization, using $^{32}$P-labeled plasmid DNA as probe. The presence of pADG6406 with ssiA is associated with a decrease in the ratio of ss- to ds DNA compared to that of the plasmid without ssiA.

This system is used to measure the effect of a candidate inhibitor, for example, 96 ORF 78 on DNA synthesis. Cultures of *S. aureus* are grown in the presence of varying concentrations of a candidate compound added directly to the medium. For compounds that correspond to polypeptides, the nucleotide sequence encoding the polypeptides can be cloned into a *S. aureus* expression vector containing an inducible promoter. The expression of the polypeptide can be induced following transfection of cells. In one assay, a plasmid containing a candidate inhibitor polypeptide coding sequence under an inducible promoter is introduced into a *S aureus* strain harboring pADG6406. The ratio of ss to ds DNA of pADG6406 is measured in the presence or in the absence of sodium arsenite (5 uM). An increase in the ratio of ss to ds DNA (10% or more) indicates an effect of the candidate modulator.

In Vitro DNA Replication Assays

In one cell-free in vitro assay, an extract prepared from *S. aureus* is supplied to a plasmid substrate, for example a circular M13ssDNA substrate, in a reaction including exogenous radiolabeled deoxynucleotide triphosphates (dATP, dTTP, dGTP and dCTP), MgCl$_2$ and ATP. The reaction is stopped and the products precipitated with trichloroacetic acid, and then filtered. Scintillation counting of the dried filter gives the level of de novo DNA replication.

Another example of assay for STAAU_R9 activity is to measure the level of radiolabeled nucleotide incorporated into DNA in a reconstituted in vitro assay using ssDNA substrate [Yuhakov et al. 1999, Cell 96: 153-163]. The replication reactions typically contained Tris-HCl [pH 7.5], MgCl$_2$, BSA, DTT, ATP, dCTP, dGTP, and dATP, [$^{32}$P] dTTP, EDTA, glycerol, ssDNA, purified *S. aureus* SSB, DNA polymerase holoenzyme and an increasing amount of STAAU_R9 polypeptide. Reactions were incubated at 37° C. for 5 min and quenched by addition of SDS and EDTA at different time points. The reaction products are precipitated with trichloroacetic acid, and then filtered. Scintillation counting of the dried filter gives the level of de novo replication.

Alternatively, a rapid fluorometric assay that measures the activity of replication enzymes can be developed to measure STAAU_R9 activity. The fluorometric assay is based on the preferential binding of a fluorescent dye to double stranded DNA, for example, de novo synthesized DNA, vs. single stranded DNA [Seville et al., 1996. Biotechniques 21: 664-672]. A reconstituted in vitro assay similar to that described above can also be developed. Reactions are incubated at 37° C. for variable times then quenched. The quenched reaction is analyzed for total DNA synthesis by adding PicoGreen dye (Molecular Probes, Eugene, Oreg.), incubating 5 min at room temperature, and reading the intensity of fluorescence of PicoGreen ($\lambda_{Ex}$, 485 nm; $\lambda_{EM}$, 525 nm). The sensitivity of the dye and the homogeneous nature of the PicoGreen assay should allow rapid screening in a non-radiometric assay format.

Testing for inhibitors, for example 96 ORF 78, is performed by incubating the compound with the reaction mixtures. The presence of an inhibitor will specifically reduce the signal in a dose-dependent manner relative to controls without inhibitor.

Assay for RNA Primase Activity

To measure the DnaG activity, the level of primase activity can be measured in an in vitro assay [Sivaraja et al., U.S. Pat. No. 6,043,038]. In the assay, DnaG polymerizes ribonucleotide triphosphates on a template to form a nucleic acid comprising one or more DNA-RNA heterohybrid regions. The presence of the resulting DNA-RNA heterohybrid regions is quantitated either by contacting the nucleic acid with a detection reagent which binds specifically to the DNA-RNA heterohybrid regions, such as an antibody that specifically recognizes the indicated molecule, or by the incorporation into the reaction mixture of a ribonucleotide triphosphate that comprises a label, such as biotin or digoxygenin, which is detected by a reagent that binds specifically to the label. The label is a composition that is detectable, either directly or indirectly, by spectroscopic, photochemical, biochemical, immunochemical, or chemical means. Useful labels include fluorescent dyes, enzymes and their substrates, biotin-streptavidin, digoxygenin, or haptens and proteins for which antibodies are available.

Samples or assays that are treated with a potential inhibitor are compared to control samples without the test compound to examine the extent of inhibition of primase activity, namely the synthesis of an RNA oligonucleotide on a DNA template. Control samples (untreated with test inhibitors) are assigned a relative primase activity value of 100; inhibition of STAAU_R9 activity is achieved when the primase activity value of the test sample relative to the control is about 75, more preferably 50, most preferably 25.

Assay for Helicase Unwinding Activity

The DnaG primase and DnaB helicase proteins of both the Gram-negative bacterium *E. coli* [Lu, Y., et al.," *Proc. Natl. Acad. Sci. U.S.A.*, 93:12902-12907, (1996)] and the Gram-positive bacterium *B. stearothermophilus* [Bird, L. E., et al., 39:171-182, Biochem.(2000)] are known to associate to form protein-protein complexes. The formation of the primase-helicase complex has important functional consequences. While DnaG primase has no measurable helicase activity, it stimulates the helicase activity of DnaB helicase when added to helicase assays containing DnaB. As for *E. coli* and *B. stearothermophilus*, it is possible that the helicase activity of DnaC from *S. aureus* is similarly stimulated by interaction with *S. aureus* DnaG primase.

Helicases use the energy of ATP hydrolysis to unwind duplex DNA at a replication fork. In the assay for helicase activity, a DNA substrate for the helicase reactions is prepared by labeling an oligonucleotide of between 50-100 nucleotides at the 5'-end with T4 polynucleotide kinase in the presence of radiolabeled nucleotides. The radiolabeled oligonucleotide is annealed to single-stranded M13 mp18 DNA (7.2 kb), resulting in a radiolabeled DNA duplex substrate with both 5'- and 3'-tails. The addition of increasing amounts of DnaG primase to DnaC helicase predictably results in the melting of the DNA duplex such that the radiolabel is separated from the M13mp18 DNA. Resolution of the reaction mixture on nondenaturing 10% polyacrylamide gels results in the migration of the labeled oligonucleotide away from remaining duplex DNA, which migrates to a position corresponding to the lower relative mobility, owing to the significantly higher relative molecular mass, of the duplex.

The helicase activity screen is performed in the presence of increasing amounts of inhibitors, for example, 96 ORF 78, to establish the ability of the candidate inhibitor to inhibit the helicase-stimulating activity of DnaG primase. The lack of an increase in electrophoretic mobility of the labeled oligonucleotide in the presence of the candidate compound indicates that the compound has affected the ability of DnaG primase to stimulate the helicase activity of DnaC.

Assay for Helicase ATPase Activity

The unwinding activity of helicase is dependent upon the presence of ATP. However, in the absence of a DNA duplex substrate, helicase demonstrates ATPase activity. The presence of DnaG primase stimulates both the helicase activity and the ATPase activity of DnaB helicase in *Bacillus stearothermophilus* [Bird, L. E., et al. (2000), Biochem., 39:171-182]. The ability of DnaG primase to stimulate the ATPase activity of helicase is determined in an ATPase assay in which ATP hydrolysis is measured under steady-state conditions. In the assay, ATP hydrolysis is linked to the oxidation of NADH, which provides for a convenient spectrophotometric determination of ATPase activity. The ATPase activity profile, measured as rate of ATP hydrolysis vs. ATP concentration, changes markedly in assays including DnaG primase, attaining a 4- to 5-fold higher rate of ATPase activity.

The influence of an inhibitor, exemplified by 96 ORF 78, upon the ability of primase to stimulate the ATPase activity is measured in the ATP assay as described with the inclusion of increasing concentrations of inhibitors in the reaction mixture. A decrease in the ATPase activity of helicase, measured as a decrease in the oxidation of NADH or as a decrease in the absorbance at 630 nm in the malachite green Pi release assay, in the presence of both primase and a candidate compound indicates that the compound has affected the ability of DnaG primase to stimulate the ATPase activity of DnaC helicase.

c. Bacterial Growth Inhibition

Compounds selected for their ability to inhibit interactions between a STAAU_R9 polypeptide and 96 ORF 78 polypeptide or to inhibit the STAAU_R9 activity can be further tested in functional assays of bacterial growth. Cultures of S. aureus are grown in the presence of varying concentrations of a candidate compound added directly to the medium or using a vehicle which is appropriate for the delivery of the compound into the cell. For compounds that correspond to polypeptides, the nucleotide sequence encoding the polypeptides can be cloned into a S. aureus expression vector containing an inducible promotor. The expression of the polypeptide could be induced following transfection of cells. For example, the polypeptide may include, but is not limited to different 96 ORF 78-derived fragments.

Following the induction of expression or the addition of compound, the cultures are then incubated for an additional 4 h at 37° C. During that period of time, the effect of inhibitors on bacterial cell growth may be monitored at 40 min intervals, by measuring, for example, the $OD_{565}$ and the number of colony forming units (CFU) in the cultures. The number of CFU is evaluated as follows: cultures are serially diluted and aliquots from the different cultures are plated out on agar plates. Following incubation overnight at 37° C., the number of colonies is counted. Non-treated cultures of S. aureus are included as negative control.

In another aspect, the present invention relates to a screening kit for identifying agonists, antagonists, ligands, receptors, substrates, enzymes, etc. for a polypeptide and/or polynucleotide of the present invention; or compounds which decrease or enhance the production of such polypeptides and/or polynucleotides, which comprises: (a) a polypeptide and/or a polynucleotide of the present invention; (b) a recombinant cell expressing a polypeptide and/or polynucleotide of the present invention; (c) a cell membrane associated with a polypeptide and/or polynucleotide of the present invention; or (d) an antibody to a polypeptide and/or polynucleotide of the present invention; which polypeptide is preferably that of SEQ ID NO: 2, and for which the polynucleotide is preferably that of SEQ ID NO: 1.

It will be appreciated that in any such kit, (a), (b), (c) or (d) may comprise a substantial component.

It will be readily appreciated by the skilled artisan that a polypeptide and/or polynucleotide of the present invention may also be used in a method for the structure-based design of an agonist, antagonist or inhibitor of the polypeptide and/or polynucleotide, by: (a) determining in the first instance the three-dimensional structure of the polypeptide and/or polynucleotide, or complexes thereof; (b) deducing the three-dimensional structure for the likely reactive site(s), binding site(s) or motif(s) of an agonist, antagonist or inhibitor; (c) synthesizing candidate compounds that are predicted to bind to or react with the deduced binding site(s), reactive site(s), and/or motif(s); and (d) testing whether the candidate compounds are indeed agonists, antagonists or inhibitors. It will be further appreciated that this will normally be an iterative process, and this iterative process may be performed using automated and computer-controlled steps.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Dalgarno or other sequence that facilitate translation of the respective mRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host that is responsible for sequelae of infection. In particular, the molecules of the invention may be used: in the prevention of adhesion of bacteria, in particular Gram positive and/or Gram negative bacteria, to eukaryotic, preferably mammalian, extracellular matrix proteins on in-dwelling devices or to extracellular matrix proteins in wounds; to block bacterial adhesion between eukaryotic, preferably mammalian, extracellular matrix proteins and bacterial STAAU_R9 proteins that mediate tissue damage and/or; to block the normal progression of pathogenesis in infections initiated other than by the implantation of in-dwelling devices or by other surgical techniques. In accordance with yet another aspect of the invention, there are provided STAAU_R9 antagonists, preferably bacteriostatic or bacteriocidal antagonists.

The antagonists of the invention may be employed, for instance, to prevent, inhibit and/or treat diseases.

Compositions, Kits and Administration

In a further aspect of the invention there are provided compositions comprising a STAAU_R9 polynucleotide and/or a S. aureus STAAU_R9 polypeptide for administration to a cell or to a multicellular organism.

The present invention provides for pharmaceutical compositions comprising a therapeutically effective amount of a polypeptide and/or polynucleotide, such as the soluble form of a polypeptide and/or polynucleotide of the present invention, antagonist peptide or small molecule compound, in combination with a pharmaceutically acceptable carrier or excipient. Such carriers include, but are not limited to, saline, buffered saline, dextrose, water, glycerol, ethanol, and combinations thereof. The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

For administration to mammals, and particularly humans, it is expected that the daily dosage level of the active agent will be from 0.01 mg/kg to 10 mg/kg, typically around 1 mg/kg. The physician in any event will determine the actual dosage that will be most suitable for an individual and will vary with the age, weight and response of the particular individual. The above dosages are exemplary of the average case. There can, of course, be individual instances where higher or lower dosage ranges are merited, and such are within the scope of this invention.

As used herein, the term "in-dwelling device" refers to surgical implants, prosthetic devices and catheters, i.e., devices that are introduced to the body of an individual and remain in position for an extended time. Such devices include, but are not limited to, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially *S. aureus* wound infections.

Many orthopedic surgeons consider that humans with prosthetic joints should be considered for antibiotic prophylaxis before dental treatment that could produce a bacteremia. Deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 mg/ml to 10 mg/ml for bathing of wounds or indwelling devices.

A vaccine composition is conveniently in injectable form. Conventional adjuvants may be employed to enhance the immune response. A suitable unit dose for vaccination is 0.5-5 microgram of antigen/kg, and such dose is preferably administered 1-3 times and with an interval of 1-3 weeks. With the indicated dose range, no adverse toxicological effects will be observed with the compounds of the invention that would preclude their administration to suitable individuals.

Sequence Databases, Sequences in a Tangible Medium, and Algorithms

Polynucleotide and polypeptide sequences form a valuable information resource with which to determine their 2- and 3-dimensional structures as well as to identify further sequences of homology. These approaches are most easily facilitated by storing the sequence in a computer readable medium and then using the stored data in a known macromolecular structure program or to search a sequence database using well-known searching tools, such as GCC.

The polynucleotide and polypeptide sequences of the invention are particularly useful as components in databases useful for search analyses as well as in sequence analysis algorithms. As used in this section entitled "Sequence Databases, Sequences in a Tangible Medium, and Algorithms," the terms "polynucleotide of the invention" and "polynucleotide sequence of the invention" mean any detectable chemical or physical characteristic of a polynucleotide of the invention that is or may be reduced to or stored in a tangible medium, preferably a computer readable form. For example, chromatographic scan data or peak data, photographic data or scan data therefrom, called bases, and mass spectrographic data. As used in this section entitled Databases and Algorithms, the terms "polypeptide of the invention" and "polypeptide sequence of the invention" mean any detectable chemical or physical characteristic of a polypeptide of the invention that is or may be reduced to or stored in a tangible medium, preferably a computer readable form. For example, chromatographic scan data or peak data, photographic data or scan data therefrom, and mass spectrographic data.

The invention provides a computer readable medium having stored thereon polypeptide sequences of the invention and/or polynucleotide sequences of the invention. The computer readable medium can be any composition of matter used to store information or data, including, for example, commercially available floppy disks, tapes, chips, hard drives, compact disks, and video disks.

In a preferred embodiment of the invention there is provided a computer readable medium having stored thereon a member selected from the group consisting of: a polynucleotide comprising the sequence of SEQ ID NO: 5; a polypeptide comprising the sequence of SEQ ID NO: 6; a set of polynucleotide sequences wherein at least one of the sequences comprises the sequence of SEQ ID NO: 5: a set of polypeptide sequences wherein at least one of the sequences comprises the sequence of SEQ ID NO: 6; a data set representing a polynucleotide sequence comprising the sequence of SEQ ID NO: 5; a data set representing a polynucleotide sequence encoding a polypeptide sequence comprising the sequence of SEQ ID NO: 6; a polynucleotide comprising the sequence of SEQ ID NO: 5; a polypeptide comprising the sequence of SEQ ID NO: 6; a set of polynucleotide sequences wherein at least one of the sequences comprises the sequence of SEQ ID NO: 5; a set of polypeptide sequences wherein at least one of the sequences comprises the sequence of SEQ ID NO: 6; a data set representing a polynucleotide sequence comprising the sequence of SEQ ID NO: 5; a data set representing a polynucleotide sequence encoding a polypeptide sequence comprising the sequence of SEQ ID NO: 6.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

The present invention is illustrated in further detail by the following non-limiting examples.

EXAMPLE 1

Identification of the Inhibitory ORF 78 from *Staphylococcus aureus* Bacteriophage 96

The *S. aureus* propagating strain 96 (PS 96 obtained from the Laboratory Center for Disease Control (CDC) Health Canada, Ottawa, Ontario) was used as a host to propagate its respective phage 96 also obtained from CDC. The phage was propagated using the agar layer method described by Swanstörm and Adams [Swanström et al. (1951) Proc. Soc. Exptl. Biol. & Med. 78: 372-375]. Phage DNA was prepared from the purified phages as described in Sambrook et al. (1989) *Molecular Cloning: A Laboratory Manual*, $2^{nd}$ Edition, Cold Spring Harbor Laboratory Press, Cold Spring Harbor, N.Y. The 96 ORF 78 (SEQ ID NO: 4) was amplified by polymerase chain reaction (PCR) from phage genomic DNA (FIG. 2). For PCR amplification, the sense strand primer starts at the initiation codon of SEQ ID NO: 3 and is preceded by a BamHI restriction site; the antisense strand starts at the last stop codon of SEQ ID NO: 3 and is preceded by a SalI restriction site. The PCR product was gel purified and digested with BamHI and SalI. The digested PCR product was then ligated into BamHI- and SalI-digested pTMSLac, a *S. aureus* vector containing kanamycin resistance selective marker, and used to transform *S. aureus* strain RN4220 [Kreiswirth et al. (1983) Nature 305:709-712]. The pTMSLac vector was constructed as followed: the arsenite-inducible promotor and the asrR gene from the pTOO21 vector [Tauriainen et al., 1997 Appl. Environ. Microbiol. 63:4456-4461] were replaced by a lactose-inducible promotor and the lacR gene from *Staphylococcus aureus*. Two oligonucleotides corresponding to a 2.18 kb-DNA region encompassing the lacR and the lac operon promotor region were synthesized. The sense strand sequence is (SEQ ID NO: 23) 5'-ccgctcgagCTCCAAATTC-CAAAACAG-3' (with a XhoI cloning site); the antisense strand sequence is: (SEQ ID NO: 24) 5'-cgggatccAATAA-GACTCCTTTTTAC-3' (with a BamHI cloning site). These two oligonucleotides were used for the PCR amplification of *Staphylococcus aureus* RN4220 DNA and to construct the pTMSLac vector.

Figure 3C:
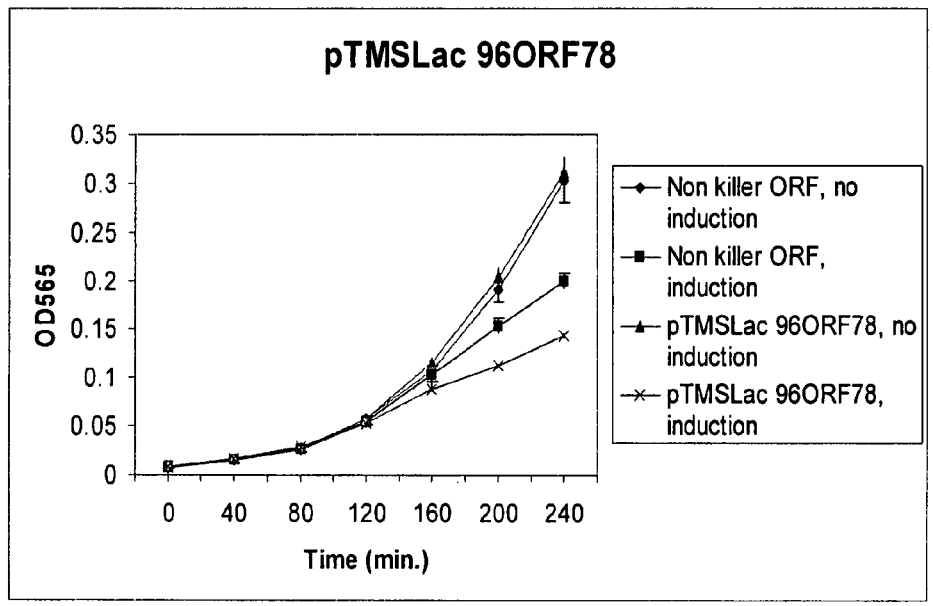
Figure 3D:
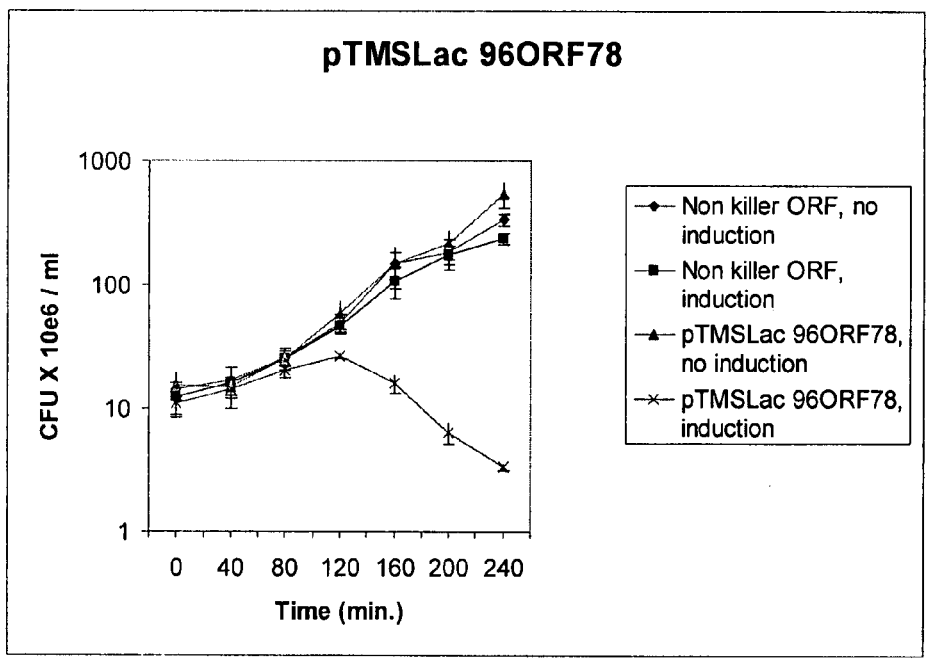

In the vector, pTMSMLac 960RF78 (FIG. 3A), phage ORF expression is under the control of the *S. aureus* lac operon promoter/operator. Selection of recombinant clones was performed on Luria-Bertani (LB) agar plates containing 30 μg/ml of kanamycin. The lactose (lac) genes of *Staphylococcus aureus* have been shown to be inducible with the addition of either lactose or galactose to the culture medium [Oskouian & Stewart, 1990, J. Bacteriol. 172: 3804-3812]. Galactose (2% w/v) was used to induce the gene expression from the lac promoter/operator in liquid assays. As shown in FIGS. 3B to D, the density of the culture, as assessed by $OD_{565}$ and colony forming units (CFU), for *S. aureus* clones harboring 96 ORF 78 increased over time under non-induced conditions. Similar growth rates were also observed with transformants harboring a non-inhibitory ORF (labeled as 'non killer' on the graphs) under both induced and non-induced conditions. Each graph represents the average obtained from three independent transformants of *S. aureus*. The expression of 96 ORF 78 inhibits the bacterial growth as observed by the reduction in CFU with time for induced cultures. At 4 h following induction, the expression of 96 ORF 78 is cytocidal resulting in a 1 log inhibition reduction in the number of CFU compared to the number of CFU initially present in the same culture (FIG. 3D). When colony plating was done in the absence of kanamycin, the antibiotic necessary to maintain the selective pressure for the plasmid encoding 96 ORF 78 (FIG. 3B), the extent of growth inhibition was reduced.

EXAMPLE 2

Identification of a *S. aureus* Protein Targeted by Bacteriophage 96 ORF 78

Figure 4:
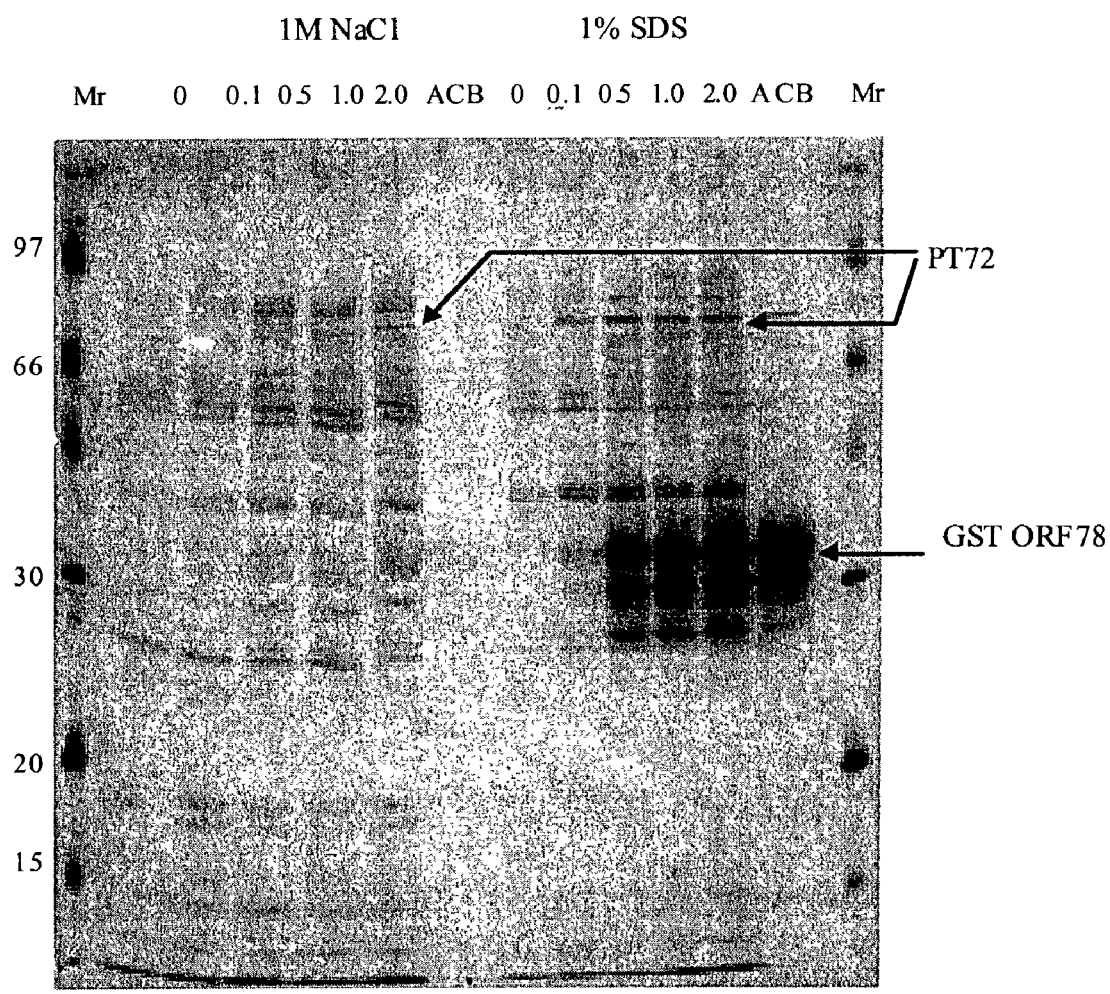
FIG. 4 shows affinity chromatography using A) GST/96 ORF 78 or B) GST as ligands with a 5.0 mg/ml *Staphylococcus aureus* extract. Eluates from affinity columns containing the ligands at 0, 0.1, 0.5, 1.0, and 2.0 mg/ml resin were resolved by 14% SDS-PAGE and the gel was stained with silver nitrate. Micro-columns were sequentially eluted with 100 mM ACB containing 0.1% Triton X-100 (SDS-PAGE not shown), 1 M NaCl ACB, and 1% SDS. Each molecular weight marker is approximately 200 ng. The lanes labeled ACB indicate eluates from a 2.0 mg/ml ligand column loaded only with ACB buffer containing 100 mM NaCl. The arrow designated PT72 indicate excised bands for protein identification.
Figure 4:
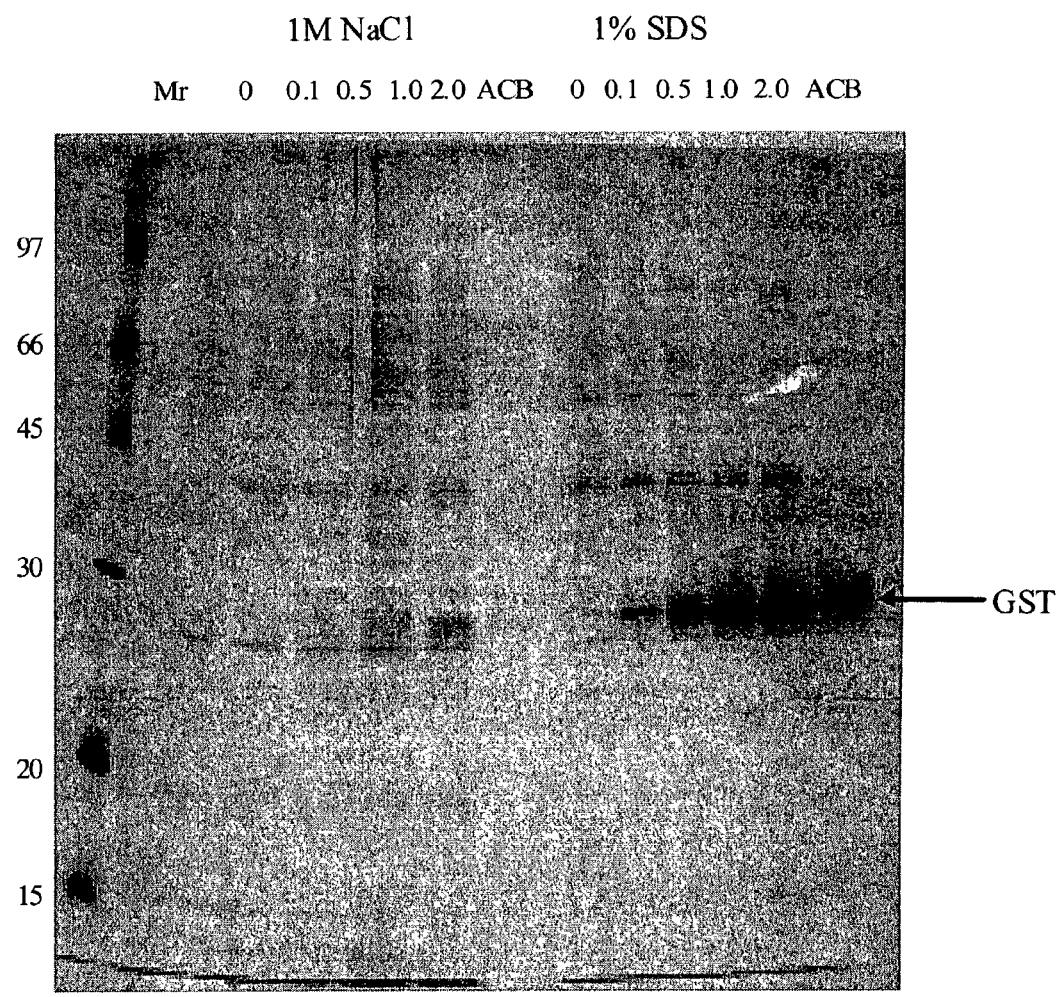

To identify the *S. aureus* protein(s) that interacts with inhibitory ORF 78 of *S. aureus* bacteriophage 96, a GST-fusion of 96 ORF 78 was generated. The recombinant protein was purified and utilized to make a GST/96ORF78 affinity column. Cellular extracts prepared from *S. aureus* cells were incubated with the affinity matrix and the matrix was washed with buffers containing increasing concentrations of salt and different detergents. The protein elution profile was assessed by SDS-polyacrylamide gel electrophoresis (SDS-PAGE). A protein of molecular mass ~72 kDa, identified as PT72, was specifically eluted from the affinity matrix (FIG. 4A) and was not detected in eluates from the GST negative control column (FIG. 4B). Eluted proteins were further characterized to determine the identity of the interacting protein and to validate the interaction of the protein with 96 ORF 78 as described in detail below.

A. Generation of GST/ORF 78 Recombinant Protein.

Bacteriophage 96 ORF 78 was sub-cloned into pGEX 4T-1 (Pharmacia), an expression vector for in-frame translational fusions with Glutathione-S-transferase (GST). The gene encoding 96 ORF 78 was obtained by digestion of pTMSMLac 960RF78 (FIG. 3A) with BamHI and SalI. The DNA fragment containing ORF78 was gel purified by QiaQuick™ spin column (Qiagen) and ligated into pGEX 4T-1 (which had been previously digested with BamHI and SaiI) to generate pGEX 4T GST/ORF78. Recombinant expression vectors were identified by restriction enzyme analysis of plasmid minipreps. Large-scale DNA preparations were performed with Qiagen columns, and the resulting plasmid was sequenced. Test expression in *E. coli* cells containing the expression plasmids were performed to identify optimal protein expression conditions. *E. coli* DH5α cells containing the expression constructs were grown at 37° C. in 2 L Luria-Bertani broth to an $OD_{600}$ of 0.4 to 0.6 (1 cm pathlength) and induced with 1 mM isopropyl-1-thio-β-D-galactosidase (IPTG) for the optimized time (3 h) and at the optimized temperature (20° C.).

B. Fusion GST/ORF78 Protein Purification.

Cells containing GST/96 ORF 78 fusion protein were suspended in 10 ml GST lysis buffer/liter of cell culture (GST lysis buffer: 20 mM Hepes pH 7.2, 500 mM NaCl, 10% glycerol, 1 mM DTT, 1 mM EDTA, 1 mM benzamidine, and 1 PMSF) and lysed by French Pressure cell followed by three bursts of twenty seconds with an ultrasonicator at 4° C. The lysate was centrifuged at 4° C. for 30 minutes at 10 000 rpm in a Sorval SS34 rotor. The supernatant was applied to a 4 ml glutathione sepharose column pre-equilibrated with lysis buffer and allowed to flow by gravity. The column was washed with 10 column volumes of lysis buffer and eluted in 4 ml fractions with GST elution buffer (20 mM Hepes pH 8.0, 500 mM NaCl, 10% glycerol, 1 mM DTT, 0.1 mM EDTA, and 25 mM reduced glutathione). The fractions were analyzed by 15% SDS-PAGE (Laemmli) and visualized by staining with Coomassie Brilliant Blue R250 stain to assess the amount of eluted GST/96 ORF 78 protein.

C. Removal of GST from GST/96 ORF 78

GST/96 ORF 78 (2.5 ml at 1.0 mg/ml) was dialyzed against 20 mM Hepes pH 7.5,150 mM NaCl, 10% glycerol, 1 mM DTT, and 1 mM EDTA at 4° C. for 3 hours. The dialyzed protein was digested with 80 units bovine thrombin protease at room temperature in the presence of 2.5 mM $CaCl_2$ for 2 hours to cleave the GST domain from the ORF domain, and the extent of digestion was determined by SDS-PAGE and Coomassie staining. The GST/96 ORF 78 was subjected to an additional overnight digestion (18° C.) with a different preparation of thrombin and again the extent of digestion was determined by SDS-PAGE and Coomassie Brilliant Blue R-250 stain. The digestion was stopped by the addition of 1 mM PMSF, 1 mM benzamidine and NaCl to a 1 M final concentration. The digested GST/96 ORF 78 was applied to a 1.5 ml glutathione sepharose column to resolve the GST and undigested GST/96 ORF 78 from 96 ORF 78.

D. *S. aureus* Extract Preparation

A *S. aureus* extract was prepared from the cell pellets using lysostaphin digestion followed by sonication and nuclease digestion. The cell pellet (2.9 g) was suspended in 8 ml of 20 mM Hepes pH 7.5, 150 mM NaCl, 10% glycerol, 10 mM $MgSO_4$, 10 mM $CaCl_2$, 1 mM DTT, 1 mM PMSF, 1 mM benzamidine, 1000 units of lysostaphin, 0.5 mg RNase A, 750 units micrococcal nuclease, and 375 units DNase 1. The cell suspension was incubated at 37° C. for 30 minutes, cooled to 4° C., and made up to a final concentration of 1 mM EDTA and 500 mM NaCl. The lysate was sonicated on ice using three bursts of 20 seconds each. The lysate was centrifuged at 20 000 rpm for 1 hr in a Ti70 fixed angle Beckman rotor. The supernatant was removed and dialyzed overnight in a 10 000 $M_r$ dialysis membrane against Affinity Chromatography Buffer (ACB; 20 mM Hepes pH 7.5, 10% glycerol, 1 mM DTT, and 1 mM EDTA) containing 100 mM NaCl, 1 mM benzamidine, and 1 mM PMSF. The dialyzed protein extract was removed from the dialysis tubing and frozen in one ml aliquots at −70° C.

E. Affinity Column Preparation

GST and GST/96 ORF 78 were dialyzed overnight against ACB buffer containing 1 M NaCl. 96 ORF 78 protein obtained from thrombin digestion of GST/96 ORF 78 was used without dialysis. Protein concentrations were determined by Bio-Rad Protein Assay and proteins were crosslinked to Affigel 10 resin (Bio-Rad) at protein/resin concentrations of 0, 0.1, 0.5, 1.0, and 2.0 mg/ml. The crosslinked resin was sequentially incubated in the presence of ethanolamine and bovine serum albumin (BSA) prior to column packing and equilibration with ACB containing 100 mM NaCl. *S. aureus* extracts were centrifuged at 4° C. in a micro-centrifuge for 15 minutes and diluted to 5 mg/ml with ACB containing 100 mM NaCl. Aliquots of 400 μl of extract were applied to 40 μl columns containing 0, 0.1, 0.5, 1.0, and 2.0 mg/ml ligand and ACB containing 100 mM NaCl (400 ul) was applied to an additional column containing 2.0 mg/ml ligand. The columns were washed with ACB containing 100 mM NaCl (400 ul) and sequentially eluted with ACB containing 0.1% Triton X-100 and 100 mM NaCl (100 ul), ACB containing 1 M NaCl (160 ul), and 1% SDS (160 ul). For further analysis, 80 ul of each eluate was resolved by 16 cm 14% SDS-PAGE [Laemmli, U.K. (1970) Nature 227: 680-685] and the protein was visualized by silver stain.

F. Affinity Chromatography

Figure 5:
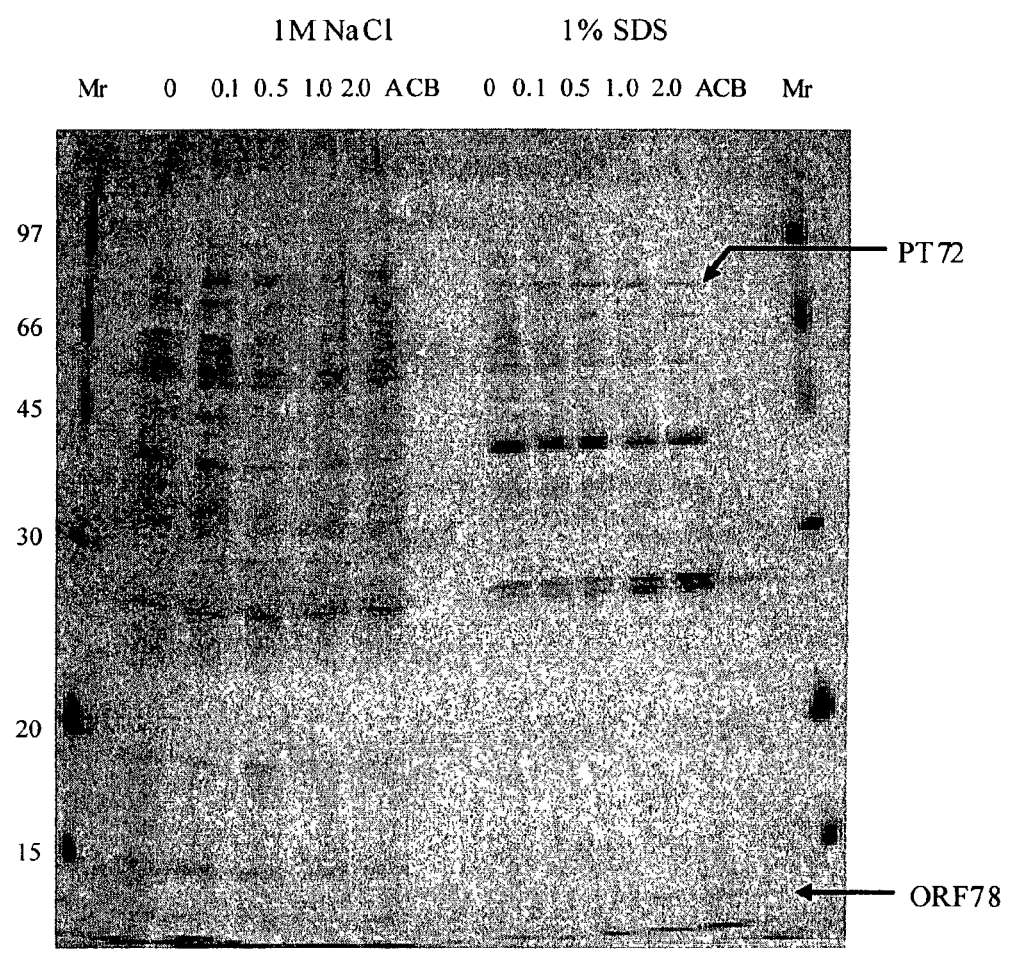
FIG. 5 shows affinity chromatography using 96 ORF 78 (GST removed) as ligand with a 5.0 mg/ml *Staphylococcus aureus* extract. Eluates from affinity columns containing the ligands at 0, 0.1, 0.5, 1.0, and 2.0 mg/ml resin were resolved by 14% SDS-PAGE and the gel was stained with silver nitrate. Micro-columns were sequentially eluted with 100 mM ACB containing 0.1% Triton X-100 (SDS-PAGE not shown), 1 M NaCl ACB, and 1% SDS. Each molecular weight marker is approximately 200 ng. The lanes labeled ACB indicate eluates from a 2.0 mg/ml ligand column loaded only with ACB buffer containing 100 mM NaCl. The arrow designated PT72 indicate excised bands for protein identification.

A candidate polypeptide of 72 kDa (PT72) was recovered from affinity columns containing either GST/96 ORF 78 (FIG. 4A) or 96 ORF 78 (FIG. 5). PT72 was recovered in the 1M NaCl eluates and in the 1% SDS eluates of the GST/96 ORF 78 chromatography experiment. PT72 was observed in the 1% SDS eluates of the 96 ORF 78 (GST removed) chromatography experiment. The PT72 polypeptide was not observed in the GST control affinity chromatography experiment. An estimation of the relative abundance of PT72 proteins in the *S. aureus* extract relies upon the assumption that nearly quantitative recovery of the candidate interacting protein has occurred during the affinity chromatography. Affinity chromatography experiments with the 5 mg/ml lysostaphin extract using ligands GST/ORF78 yielded approximately 50 ng of PT72 in the eluate of the 2.0 mg/ml column. Although protein quantitation from silver stained SDS-PAGE gels is only approximate, the estimated abundance of PT72 in the extracts is approximately 0.01% of the total cellular protein.

G. Identification of *S. aureus* STAAU_R9 as an 96 ORF 78 Interacting Protein

The candidate protein PT72 was excised from SDS-PAGE gels and prepared for tryptic peptide mass determination by MALDI-ToF mass spectrometry. [Qin, J., et al. (1997) *Anal. Chem.* 69, 3995-4001]. As exemplified in FIG. 6, high quality mass spectra were obtained. The PT72 proteins observed in the two affinity chromatography experiments (eluates presented in FIGS. 4 and 5) were identical as determined by the masses of the tryptic peptides. The gel slice containing PT72 was found to contain a single protein. The PT72 band was identified as an open reading frame (herein referred as 'STAAU_R9') found in Contig 286 of the University of Oklahoma genome sequencing project database. PT72 is highly similar, although not identical, to *S. aureus* DnaG (gi|2494147|sp|O05338|PRIM_STAAU DNA PRIMASE, gi|1943994|dbj|BAA19493.1| (AB001896).

Figure 6:
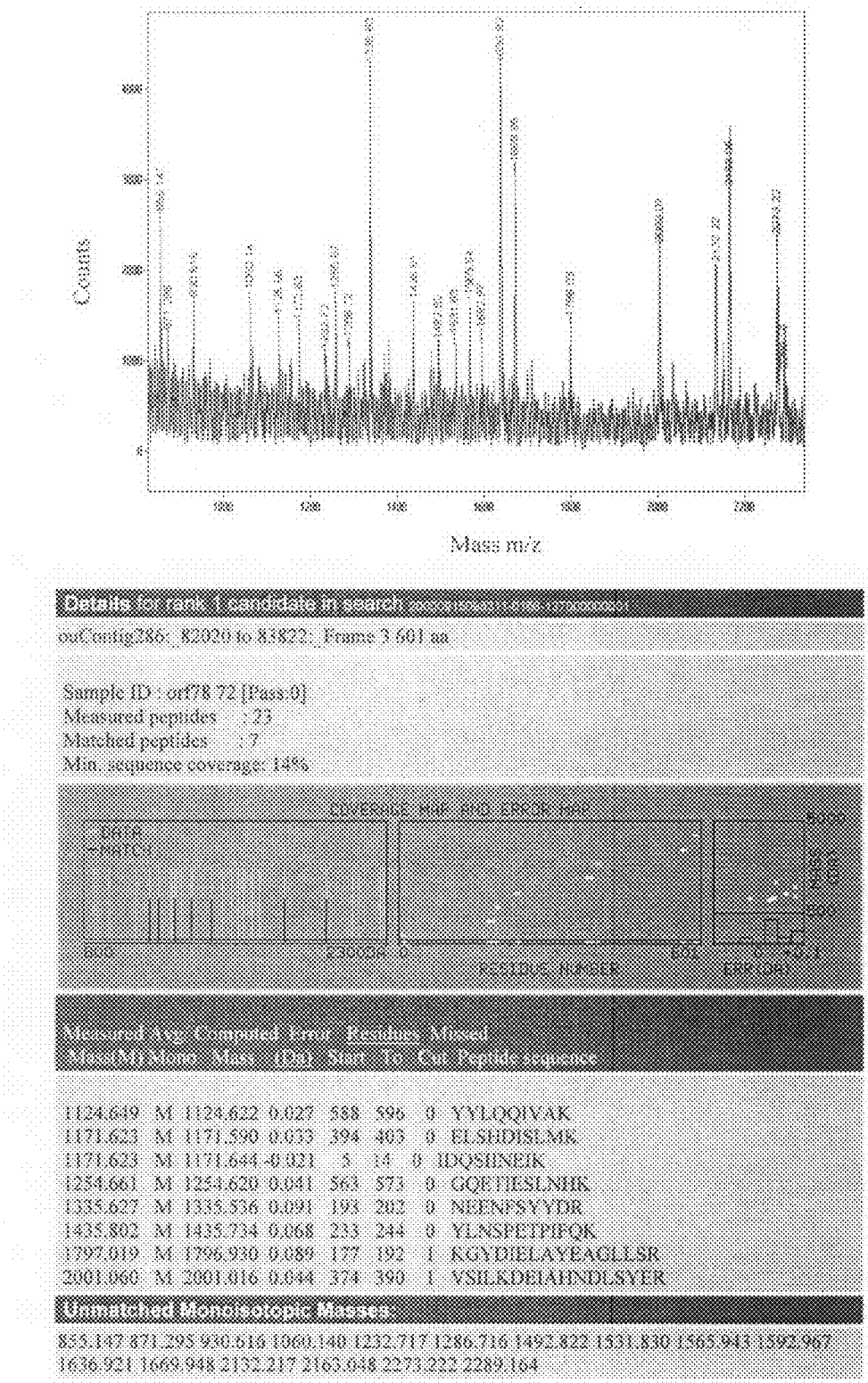
FIG. 6 shows the tryptic peptide mass spectrum analysis of the PT72 protein interacting with 96 ORF 78. The gel slice containing PT72 contained one protein. The PT72 band was identified as an open reading frame, herein referred as STAAU_R9, found in Contig 286 of the University of Oklahoma genome sequencing project database (Web site with the remainder of the address being genome.ou.edu/staph.html) (SEQ ID NOS 29-36).

As shown in FIG. 7B, the result of the optimal global amino acid sequence alignment of STAAU_R9 with the described *S. aureus* DnaG (Swissprot No: O05338) reveals a 92% identify between the two polypeptides. The discrepancies between the sequences of DNA primase from *S. aureus* as reported in Swissprot and as reported in the University of Oklahoma *S. aureus* genome sequencing project database is noteworthy. The N-terminal sequence of STAAU_R9 (SEQ ID NO: 2) was predicted based on the presence of a fragment of 1171.623 in the mass spectrum (FIG. 6). This tryptic-digested fragment corresponds to the mass predicted from the sequence (SEQ ID NO: 31: IDQSII-NEIK) extending from amino acid residue 5 to 14 of the deduced amino acid sequence of STAAU_R9. In addition, the 5' DNA sequence of STAAU_R9 on the genome of *S. aureus* strain RN4220 was confirmed by PCR and DNA sequence analyses with the following primer pair; (SEQ ID NO: 25) 5'-GCGCATCTGTAAAACCACG-3' AND (SEQ ID NO: 26) 5'-GCACGAATTCAAGAAGAATTG-3'. FIG. 7B also shows that STAAU_R9 is similar to several bacterial DNA primases including DnaG polypeptides of *B. stearothermophilus*, *B. subtilis* and *E. coil*, with identities of 34%, 36% and 27%, respectively. FIG. 7A shows the results of the STAAU_R9 Hidden Markov Model searching analysis of the publicly available Pfam database identifying two highly related Pfam motifs in the STAAU_R9 region spanning amino acid position 1 to 339. STAAU_R9 harbors a N-terminal zinc finger-binding domain that could be involved in template DNA recognition and a Toprim domain, located centrally, and which corresponds to a conserved catalytic domain in bacterial DnaG-type primases. The C-terminal region of STAAU_R9 is only weakly conserved amongst bacterial DNA primases as exemplified in the optimal global amino acid sequences alignment presented in FIG. 7B.

EXAMPLE 3

Confirmation of the Interaction Between STAAU_R9 and 96 ORF 78 by Yeast Two-Hybrid Analysis To validate the identification of S. aureus STAAU_R9 as an interacting partner of bacteriophage 96 ORF 78 and to identify the specific domains of interaction, we first determined the 96 ORF 78 interacting domain of S. aureus STAAU_R9. Recombinant STAAU_R9 protein was thus subjected to deletion analysis using the yeast two-hybrid system.

A. Generation of 96 ORF 78 and STAAU_R9 Recombinant Polypeptides for Yeast Two-hybrid Analysis.

The polynucleotide sequence of STAAU_R9 was obtained from S. aureus strain RN4220 genomic DNA by PCR utilizing oligonucleotide primers that targeted the predicted translation initiation and termination codons of the STAAU_R9 gene (SEQ ID NO: 1). The initiation codon used to amplified STAAU_R9 (TTG corresponding to a leucine) corresponds to the predicted start codon of STAAU_R9.

Figure 8:
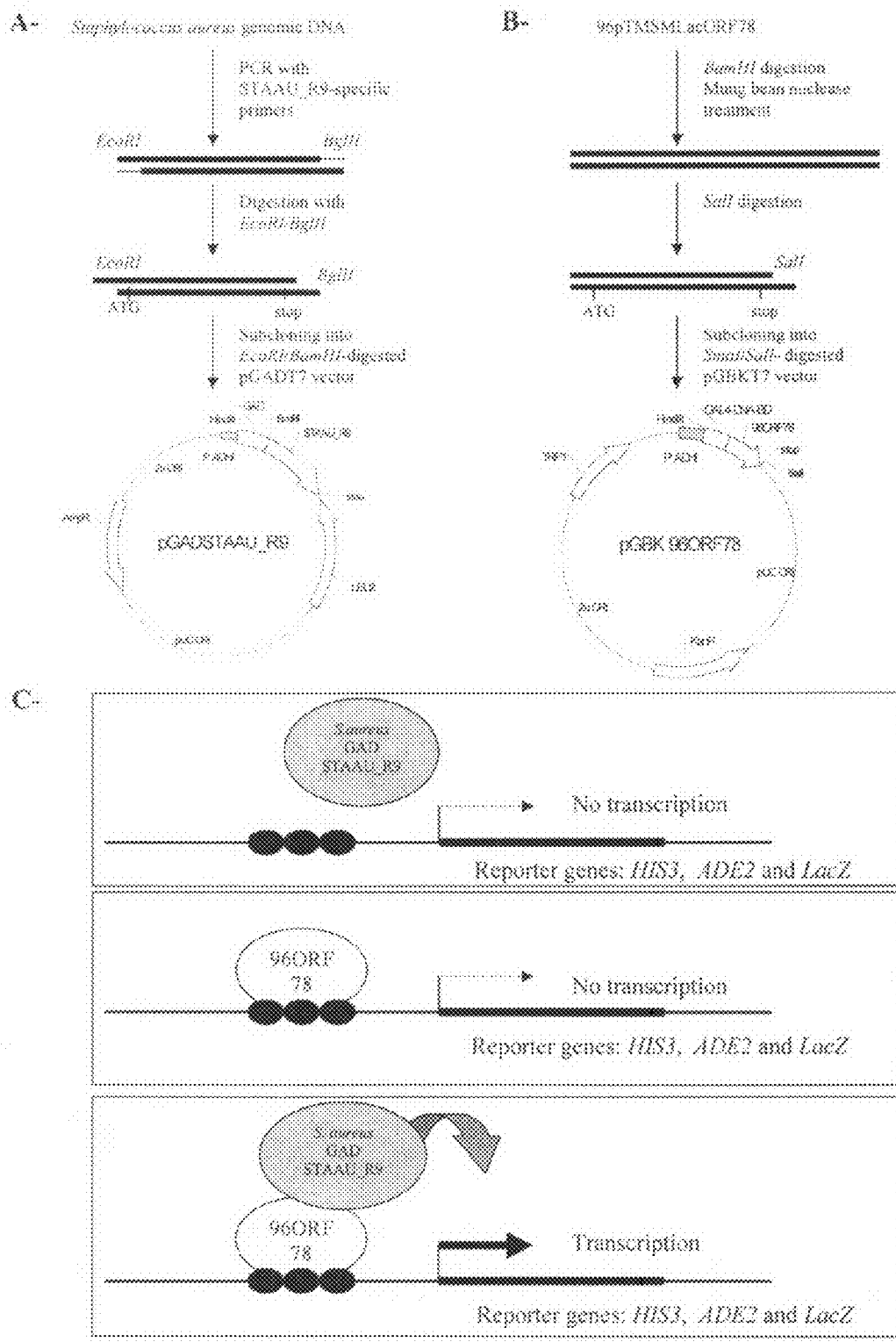
FIG. 8 shows schematic representations of A) the cloning procedure for *S. aureus* STAAU_R9 and STAAU_R9-related fragments in the yeast expression vector pGADT7 (pGADSTAAU_R9); B) the cloning procedure for phage 96 ORF 78 in the yeast expression vector pGBKT7 (pGBK 96ORF78); and C) the yeast two-hybrid system in three stylized cells expressing either GADSTAAU_R9 (top panel), 96 ORF 78 (middle panel), or both GADSTAAU_R9 and 96 ORF 78 (bottom panel).

As illustrated in FIG. 8A, the sense strand primer (FIG. 11A; SEQ ID NO: 8) targets the initiation codon and is preceded by a EcoRI restriction site; the antisense oligonucleotide (FIG. 11A; SEQ ID NO: 9) targets the stop codon and is preceded by a BglII restriction site. The PCR product was purified using the Qiagen PCR purification kit and digested with EcoRI and BglII. The digested PCR product was ligated to EcoRI- and BglII-digested pGADT7 vector (Clontech Laboratories), yielding pGADSTAAU_R9. A similar strategy was used for the cloning of STAAU_R9 into the pGBKT7 vector (Clontech Laboratories), yielding pGBKSTAAU_R9. Bacteriophage 96 ORF 78 (FIG. 2; SEQ ID NO: 4) was fused either to the carboxyl terminus of the yeast Gal4 DNA binding domain (encoded by the pGBKT7 vector) or to the yeast Gal4 activation domain (encoded by pGADT7). As shown in FIG. 8B, the 96 ORF 78 was obtained by digestion of pTMSMLac 960RF78 (described in FIG. 3A) with BamHI, followed by treatment with Mung bean nuclease and digestion with SalI. The DNA restriction product containing 96 ORF 78 was gel purified and ligated into the SmaI and SalI-digested pGBKT7 expression vector. The recombinant expression vector was identified by restriction enzyme analysis of plasmid DNA.

B. Cloning of STAAU_R9 Fragments into the Yeast Inducible Expression System

Figure 10:
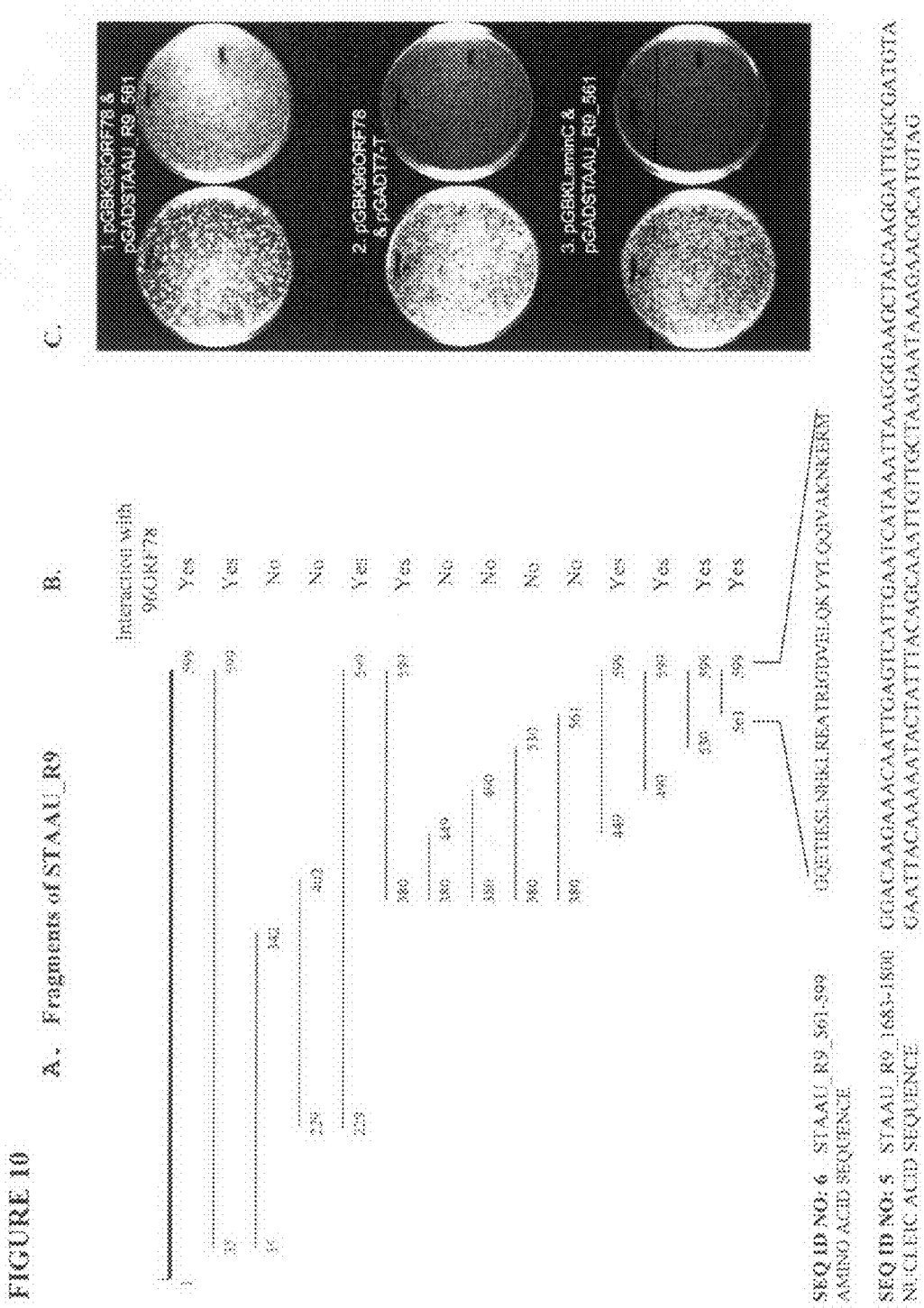
FIG. 10 shows the results of the yeast two-hybrid analysis that were designed to test the interaction between small fragments of STAAU_R9 and 96 ORF 78. A) Schematic representation of the different fragments of STAAU_R9 that were cloned in yeast pGAD and pGBK vectors. Yeasts were co-transformed with 96 ORF 78 and the different STAAU_R9 fragments, and co-transformants were plated in parallel on TL minus SD medium and on THAL minus SD medium. B) Summary of the results of growth on selective THAL minus SD medium of yeasts expressing the different STAAU_R9-related fragments in the presence of 96 ORF 78 (under the label: 'Interaction with 96 ORF 78'); C) Results of yeast two-hybrid analysis showing the interaction between the polypeptide of SEQ ID NO: 6, containing the amino acids 561-599 of STAAU_R9, and 96 ORF 78. This sequence represents the minimal domain of STAAU_R9 interacting with 96 ORF 78 as determined by yeast two-hybrid analysis.

As shown in FIG. 10A, thirteen truncated fragments of the polypeptide sequence of STAAU_R9 (FIG. 1; SEQ ID NO: 2) were also amplified by PCR from S. aureus genomic DNA by utilizing appropriate pairs of oligonucleotide primers (FIGS. 11A and B) and ligating the PCR products to the pGADT7 vector. FIG. 11B identifies primer pairs that were used during PCR. Numbers at the left and right end extremities of each fragment in FIG. 10A correspond to the N-terminal and C-terminal amino acid residues, respectively (according to the amino acid sequence of STAAU_R9 in SEQ ID NO: 2).

C. Yeast Two-hybrid Analysis.

As exemplified in FIG. 9A for the STAAU_R9 fragment extending from amino acid 35 to 599, the pGAD and pGBK plasmids bearing different combinations of constructs (as indicated above each pair of petri plates) were introduced into a yeast strain (AH109, Clontech Laboratories), previously engineered to contain chromosomally-integrated copies of E. coli lacZ and the selectable HIS3 and ADE2 genes. Co-transformants were plated in parallel on yeast synthetic medium (SD) supplemented with amino acid drop-out lacking tryptophan and leucine (TL minus) and on SD supplemented with amino acid drop-out lacking tryptophan, histidine, adenine and leucine (THAL minus). Co-transformants harbouring the 96 ORF 78 polypeptide only grew on selective SD THAL minus medium in the presence of STAAU_R9. Induction of the reporter HIS3 and ADE2 genes is dependent upon the interaction of STAAU_R9 with 96 ORF 78 since co-transformants with appropriate control plasmids (pGBKT7LaminC or pGADT7-T) are not viable on SD THAL minus medium. The only exception is the growth of yeast co-transformed with pGKB STAAU_R9 and the control pGADT7-T plasmids on SD THAL minus medium.

The interaction of STAAU_R9 and 96 ORF 78 is also clearly demonstrated by the observed 10-fold increase, over the background level, of the β-galactosidase activity in both 96 ORF 78-STAAU_R9 co-transformants (FIG. 9B, Sample ID 1 and 4). These results are consistent with the interpretation that the S. aureus STAAU_R9 identified herein is the host target of bacteriophage 96 ORF 78.

In parallel experiments, each pGAD vector harboring STAAU_R9 truncation fragments was introduced into AH 109 yeast cells with the pGBK vector containing 96 ORF 78 (FIG. 10A). The resulting co-transformants were analyzed for their ability to induce expression of reporter genes. FIG. 10B shows the results of interaction for each STAAU_R9-related fragment with 96 ORF 78. Portions of STAAU_R9 extending from amino acids residues 561 to 599 (herein referred to as SEQ ID NO: 6 or STAAU_R9 561 599) was found to interact with bacteriophage 96 ORF 78 since the introduction of appropriate plasmids into host yeast cells resulted in their growth on THAL minus SD medium (FIG. 10C; top pair of petri plates). This 39 amino acid sequence (SEQ ID NO: 6) represents the minimal domain of STAAU_R9, identified by yeast two hybrid assay, that maintains the interaction capacity with 96 ORF 78. Of note, this amino acid segment is poorly conserved amongst S. aureus, B. stearothermophilus, B. subtilis, and E. coli (FIG. 7B).

EXAMPLE 4

Characterization of the Interaction Between STAAU_R9 and 96 ORF 78 Purified Recombinant Proteins and Fragment Thereof by Affinity Blotting and Surface Plasmon Resonance Assays To characterize the interaction between STAAU_R9 and the inhibitory ORF 78 of S. aureus bacteriophage 96, STAAU_R9 (SEQ ID NO: 2) as well as fragment thereof (SEQ ID NO: 6) and 960RF078 (SEQ ID NO: 4), the recombinant proteins were expressed as GST-tagged fusion and purified proteins were used in affinity blotting (Far western) and surface plasmon resonance (Biacore) assays.

A. Bacterial Strains Plasmid Constructs:

E. coli BL21 (Amersham-Phramacia) was used as a host strain for cloning and expression of the recombinant proteins. The pGEX-6P1 (Pharmacia Amersham Biotech) that encodes an N-terminal GST tag and a PreScission protease cleavage was used to generate GST fusion constructs. The pGEX-6PK was obtained by cloning synthetic annealed oligonucleotides corresponding to the heart muscle kinase (HMK) phosphorylation site (SEQ ID NO: 27 5'-GATCTCGTCGTGCATCTGTTGGATC-CCCGGAATTCCCGGG-3' and SEQ ID NO: 28 5'-TC-GACCCGGGAATTCCGGGGATCCAACAGATG-CAC-GACGA-3') [Kaelin et al. 1992, Cell 70: 351-364], into pGEX-6P1 linearized with BamHI-SalI. Insertion of the DNA duplex was confirmed by sequencing and the plasmid is referred to as pGEX-6PK.

Construction of pGEX-6PK 96ORF078 was performed by the digestion of the pTMSLac 96ORF078 plasmid construct with BamHI-SalI and the insert corresponding to 96 ORF 78 was gel purified using the Qiagen DNA extraction kit and ligated into the unique BamHI-SalI sites pGEX-6PK. The presence of 96 ORF 78 insert was confirmed by PCR amplification and sequence analysis. DNA was made using Qiagen plasmid purification kit.

Construction of pGEX-6PK STAAU_R9 was done by digestion of the pGAD STAAU_R9 with EcoRI-XhoI and the insert corresponding to STAAU_R9 was gel purified and ligated into the EcoRI-SalI sites of pGEX-6PK. The presence of the insert was confirmed by PCR using STMU_R9 specific primers. A similar strategy was used to clone the DNA encoding the C-terminal portion of STAAU_R9 extending from amino acid position 561 to 599. The insert was obtained from the pGAD STAAU_R9_561_599 plasmid and cloned into pGEX-6PK to yield pGEX-6PK_STAAU_R9_561_599. The presence of the insert was confirmed by digestion with BamHI-NotI restriction enzymes.

B. Protein Expression and Purification.

The overexpression of GST fusion proteins was performed by inducing log-phase cultures with 1 mM of IPTG for 3h at 25° C. Unless specified, all the subsequent steps were performed at 4° C. Cells were harvested by centrifuging at 5,000 rpm on a JA-10 rotor (Beckman) for 15 min and the bacterial pellet was resuspended in 100 ml of ice-cold phosphate buffer saline (PBS), divided into 4 aliquots and centrifuged as above. Each aliquot was resuspended in 5 ml of STE (10 mM Tris pH 8.0, 1 mM EDTA, 150 mM NaCl and 0.1 mg/ml Lyzozyme). After incubation of 15 min on ice, 10 mM dithiothreithol (Gibco BRL) and 1.4% Sarkosyl (Sigma) were added and cell lysis was achieved by three cycles of sonication (20 seconds/cycle).

The cell lysate was centrifuged at 16,000 rpm on a JA-20 rotor (Beckman) for 20 min and the supernatant was treated with 2% Triton X-100 (Sigma) in a total volume of 20 ml for 30 min at room temperature with end-over-end rotation. The lysate was centrifuged at 16,000 rpm on an JA-20 rotor for 20 min and the supernatant was incubated with 1 ml bed volume of glutathione Sepharose-4B beads (Amersham-Pharmacia) for 60 min. Bound proteins were washed extensively with PBS, transferred to an eppendorf tube and proteins were either eluted as GST fusions with 10 mM reduced glutathione (Sigma) or cleaved from the GST portion by digestion with 40 Units of PreScission™ protease (Pharmacia-A) in 500 µl of 50 mM Tris pH 7.0, 150 mM NaCl, 1 mM EDTA and 1 mM DTT. After 5 h incubation with end-over-end rotation, samples were centrifuged for 5 min at 13,000 g in a microfuge and the supernatants were collected and the proteins were stored at −80° C.

Protein concentration was determined using the Biorad protein assay. Protein were analyzed by 12% SDS-PAGE and visualized by Coommassie Brilliant Blue R-250 staining.

C. Affinity Blotting Assay

Radiolabeling of the proteins was done through the heart muscle phosphate acceptor site with the heart muscle kinase enzyme (HMK). Each labeled probe was incubated with its respective, immobilized cognate protein, and the interaction is detected by exposure to X-ray film after extensive washes. For radiolabeling with [$^{32}$P]-ATP, 5-10 µg of GST-cleaved 96 ORF 78 polypeptide, STAAU_R9 or STAAU_R9_561_599 were incubated with 50 Units of catalytic sub-unit of cAMP dependent protein kinase "Heart Muscle Kinase" (Sigma) in a total volume of 100 µl containing 200 mM Tris pH 7.5, 1 M NaCl, 120 mM MgCl$_2$, 10 mM DTT and 50 µCi of [$\gamma^{32}$P]-ATP (3000 ci/mmoles) (NEN/Mandel) for 30 min at room temperature. To remove free nucleotides, the proteins were applied to Sephadex-G50 NICK columns (Amersham-Pharmacia) and eluted with Z-buffer (25 mM Hepes pH 7.7, 12.5 mM MgCl$_2$, 20% Glycerol, 100 mM KCl & 1 mM DTT) and the incorporation of $\gamma^{32}$P-ATP was determined by counting in a liquid scintillation counter.

Increasing amounts (from 50 ng to 4.5 ug of GST-cleaved proteins were resolved on a 10% sodium dodecyl sulfate-polyacrylamide gel electrophoresis (SDS-PAGE) and blotted onto nitrocellulose membrane (Millipore). Immobilized proteins were denatured by incubating the membrane with 6M urea in HBB buffer (25 mM Hepes-KOH pH 7.7, 25 mM NaCl, 5 mM MgCl$_2$, 1 mM DTT) for 20 min at 4° C. The proteins were renatured in situ by a progressive dilution of urea in HBB buffer. The membrane was blocked for at least 1 h with 5% milk in HBB supplemented with 0.05% NP-40 and for 45 min in 1% milk in HBB supplemented with 0.05% NP-40.

The hybridization was performed for overnight in hybridization buffer (20 mM Hepes-KOH pH 7.7, 75 mK KCl, 0.1 mM EDTA 2.5 mM MgCl$_2$, 0.05% NP-40 and 1% milk) containing ~250,000 cpm/ml of [$^{32}$P]-ATP labelled protein as a probe in a volume of 10 ml. The membranes were washed 3 times for 10 min with the hybridization buffer and exposed to x-ray film.

A specific signal was observed when using [$^{32}$P]-96 ORF 78, as a probe, against immobilized GST/STAAU_R9, GST-cleaved STAAU_R9, GST/STAAU_R9_561_599 or GST-cleaved STAAU_R9_561_599 compared to lane that contains purified GST protein as a negative control (results not shown). Similarly, a specific signal was observed when using [$^{32}$P]-STAAU_R9 or [$^{32}$P]-STAAU_R9_561_599, as a probe, against immobilized GST/96ORF78 or GST-cleaved 96 ORF 78 compared to lane that contains purified GST protein as a negative control (results not shown).

D. Surface Plasmon Resonance Assay

The identification of S. aureus STAAU_R9 as an interacting partner of bacteriophage 96 ORF 78 was also validated by surface plasmon resonance (Biacore 2000 Biosensor) using purified recombinant polypeptides. GST/STAAU_R9_561_599 was captured as ligand by an anti-GST antibody which had been covalently coupled to the surface of a CM5 sensor chip; a blank surface with anti-GST antibody and without captured ligand was used as a negative control. Injection of purified 96 ORF 78 protein over the two surfaces indicated specific capture of 96 ORF 78 by immobilized STAAU_R9_561_599 (results not shown). Similarly, STAAU_R9 was covalently coupled as ligand directly to the surface of a CM5 sensor chip; a blank surface without captured ligand was used as a negative control. Injection of purified 96 ORF 78 protein over the two surfaces indicated specific capture of 96 ORF 78 by immobilized STAAU_R9.

CONCLUSION

By virtue of the interaction between the inhibitory bacteriophage 96 ORF 78 and the STAAU_R9, the STAAU_R9 gene and its gene product have thus been identified as novel bacterial targets for the screening and identification of anti-bacterial agents and more particularly for anti *S. aureus* agents. The present invention also provides novel diagnosis, prognosis and therapeutic methods based on STAAU_R9, and/or bacteriophage 96 ORF 78 and/or a compound identified in accordance with the present invention.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, fragments of STAAU_R9 that specifically binds with 96 ORF 78 polypeptide are all within the scope of the present invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

Although the present invention has been described hereinabove by way of preferred embodiments thereof, it can be modified without departing from the spirit and nature of the subject invention as defined in the appended claims.

What is claimed is:

1. An isolated or purified first polypeptide which binds to a second polypeptide comprising SEQ ID NO:4, said first polypeptide comprising amino acids 380 to 599 of SEQ ID NO: 2, wherein said amino acids 380 to 599 are at the carboxy terminus of said first polypeptide.

2. An isolated or purified polypeptide consisting of the amino acid sequence of SEQ ID NO: 2.

3. An isolated or purified polypeptide which binds a polypeptide comprising SEQ ID NO:4, wherein said isolated or purified polypeptide has RNA primase activity and wherein said isolated or purified polypeptide comprises an amino acid sequence selected from the group consisting of:
   (a) a first amino acid sequence having at least 95% identity to amino acids 1-599 of SEQ ID NO: 2; and
   (b) a second amino acid sequence comprising amino acids 1-599 of SEQ ID NO: 2.

4. An isolated or purified polypeptide comprising the amino acid sequence of SEQ ID NO: 2.

5. An isolated or purified fragment of SEQ ID NO: 2, wherein said fragment binds a polypeptide comprising SEQ ID NO:4, and wherein said fragment is selected from the group consisting of amino acids 229 to 599 of SEQ ID NO:2 and amino acids 380 to 599 of SEQ ID NO:2.

6. A method for determining whether a candidate compound is an inhibitor of the polypeptide set forth in SEQ ID NO:2, comprising:
   (a) contacting a polypeptide of any one of claims 2, 4 and 5 with a candidate compound,
   (b) assaying for RNA primase activity of the polypeptide of (a), and
   (c) comparing the results from the assay of (b) with results of an assay performed using a polypeptide identical to the polypeptide of (a) that has not been contacted with the candidate compound, wherein when the RNA primase activity of the polypeptide of(a) is decreased in the presence of the candidate compound compared to in the absence of the candidate compound, the candidate compound is determined to be an inhibitor of the polypeptide set forth in SEQ ID NO:2.

7. A method for determining whether a candidate compound is an activator of the polypeptide set forth in SEQ ID NO:2, comprising:
   (a) contacting a polypeptide of any one of claims 2, 4 and 5 with a candidate compound,
   (b) assaying for RNA primase activity of the polypeptide of(a), and
   (c) comparing the results from the assay of (b) with results of an assay performed using a polypeptide identical to the polypeptide of (a) that has not been contacted with the candidate compound, wherein when the RNA primase activity of the polypeptide of (a) is increased in the presence of the candidate compound compared to in the absence of the candidate compound, the candidate compound is determined to be an activator of the polypeptide set forth in SEQ ID NO:2.

8. A method for determining whether a candidate compound binds the polypeptide set forth in SEQ ID NO:2, comprising:
   (a) contacting a polypeptide of any one of claims 2, 4 and 5 with a candidate compound, and
   (b) detecting binding of said candidate compound to the polypeptide of (a).

9. The method of claim 8, further comprising measuring the ability of the candidate compound to increase or decrease the RNA primase activity of the polypeptide set forth in SEQ ID NO:2.

10. The method of claim 8, wherein detection of said binding is performed by a technique selected from the group consisting of phage display, surface plasmon resonance, time-resolved fluorescence resonance energy transfer, fluorescence polarization, scintillation proximity assay, and biosensor assay.

11. The method of claim 6, wherein said candidate compound is selected from the group consisting of a small organic molecule, a peptide, a polypeptide and an antibody.

12. The method of claim 7, wherein said candidate compound is selected from the group consisting of a small organic molecule, a peptide, a polypeptide and an antibody.

13. The method of claim 8, wherein said candidate compound is selected from the group consisting of a small organic molecule, a peptide, a polypeptide and an antibody.

* * * * *